US008871900B2

(12) United States Patent
Okunieff et al.

(10) Patent No.: US 8,871,900 B2
(45) Date of Patent: Oct. 28, 2014

(54) FIBROBLAST GROWTH FACTOR (FGF) ANALOGS AND USES THEREOF

(75) Inventors: Paul Okunieff, Gainesville, FL (US); Lurong Zhang, Gainesville, FL (US)

(73) Assignee: University of Rochester, Rochester, NY (US)

( * ) Notice: Subject to any disclaimer, the term of this patent is extended or adjusted under 35 U.S.C. 154(b) by 396 days.

(21) Appl. No.: 12/999,540

(22) PCT Filed: Jun. 16, 2009

(86) PCT No.: PCT/US2009/047498
§ 371 (c)(1),
(2), (4) Date: May 11, 2011

(87) PCT Pub. No.: WO2009/158238
PCT Pub. Date: Dec. 30, 2009

(65) Prior Publication Data
US 2011/0207663 A1    Aug. 25, 2011

Related U.S. Application Data

(60) Provisional application No. 61/061,851, filed on Jun. 16, 2008.

(51) Int. Cl.
| | | |
|---|---|---|
| *C07K 4/12* | (2006.01) | |
| *A61K 38/10* | (2006.01) | |
| *A61K 38/18* | (2006.01) | |
| *A61L 29/04* | (2006.01) | |
| *A61B 17/12* | (2006.01) | |
| *A61L 27/54* | (2006.01) | |
| *A61L 31/16* | (2006.01) | |
| *C07K 14/50* | (2006.01) | |
| *A61L 27/22* | (2006.01) | |
| *A61L 29/16* | (2006.01) | |
| *A61L 31/04* | (2006.01) | |

(52) U.S. Cl.
CPC ........... *A61K 38/1825* (2013.01); *A61L 29/048* (2013.01); *A61B 17/1215* (2013.01); *A61L 27/54* (2013.01); *A61L 31/16* (2013.01); *C07K 14/503* (2013.01); *A61L 27/227* (2013.01); *A61B 17/1214* (2013.01); *A61L 2300/25* (2013.01); *A61L 29/16* (2013.01); *A61L 31/047* (2013.01)
USPC .............. 530/326; 514/5.1; 514/9.1; 514/9.4; 514/18.6

(58) Field of Classification Search
None
See application file for complete search history.

(56) References Cited

FOREIGN PATENT DOCUMENTS

| CN | 1757738 | 4/2006 |
|---|---|---|
| EP | 1 600 109 | 11/2005 |
| WO | WO 2004/018499 | 3/2004 |

OTHER PUBLICATIONS

Kanazawa et al., Am J Gastroenterology, 96(3): 822-828, 2001.*
Ohyama et al., J Neurosurg., 102:109-115, 2005.*
Takakura et al., Cell, 102:199-209, 2000.*
Sommer et al., Biochem. Biophys. Res. Comm., 160:1267-1274, published as Genbank Accession # A32484 on Oct. 20, 1989.*
International Preliminary Report on Patentability mailed by the International Bureau on Dec. 30, 2009 for PCT/US2009/047498 filed on Jun. 16, 2008 and published as WO 2009/158238 (Applicant—University of Rochester // Inventor—Okunieff et al.) (4 pages).
Written Opinion mailed by the International Bureau on Dec. 30, 2009 for PCT/US2009/047498 filed on Jun. 16, 2008 and published as WO 2009/158238 (Applicant—University of Rochester // Inventor—Okunieff et al.) (3 pages).
International Serach Report mailed by the International Bureau on Dec. 30, 2009 for PCT/US2009/047498 filed on Jun. 16, 2008 and published as WO 2009/158238 (Applicant—University of Rochester // Inventor—Okunieff et al.) (3 pages).
Allouche M, et al. (1995) The role of fibroblast growth factor-2 (FGF-2) in hematopoiesis. Prog Growth Factor Res. 1995;6(1):35-48.
Ballmaier M, et al. (1998) Defective c-Mpl signaling in the syndrome of thrombocytopenia with absent radii. Stem Cells. 16 Suppl 2:177-184.
Bartley TD, et al. (1994) Identification and cloning of a megakaryocyte growth and development factor that is a ligand for the cytokine receptor Mpl. Cell. 77(7):1117-1124.
Burgess WH, et al. (1989) The heparin-binding (fibroblast) growth factor family of proteins. Annu Rev Biochem. 58:575-606.
Chen J, et al. (1995) Regulation of platelet activation in vitro by the c-Mpl ligand, thrombopoietin. Blood. 86(11):4054-4062.
de Sauvage FJ, et al. (1994) Stimulation of megakaryocytopoiesis and thrombopoiesis by the c-Mpl ligand. Nature. 369(6481):533-538.
Debili N. (1995) The Mpl-ligand or thrombopoietin or megakaryocyte growth and differentiative factor has both direct proliferative and differentiative activities on human megakaryocyte progenitors. Blood. 86: 2516-2525.
Ding I, et al. (1997) Radioprotection of hematopoietic tissue by fibroblast growth factors in fractionated radiation experiments. Acta Oncol 36(3):337-340.
Drucker DJ. (2007) The role of gut hormones in glucose homeostasis. J Clin Invest. 117(1):24-32.
Ezumi Y, et al. (1995) Thrombopoietin, c-Mpl ligand, induces tyrosine phosphorylation of Tyk2, JAK2, and STAT3, and enhances agonists-induced aggregation in platelets in vitro. FEBS Lett. 374(1):48-52.

(Continued)

*Primary Examiner* — Daniel E Kolker
*Assistant Examiner* — Stacey N MacFarlane
(74) *Attorney, Agent, or Firm* — Smith Gambrell & Russell LLP

(57) ABSTRACT

The invention relates to novel peptide comprising FGF-P and methods of use thereof.

45 Claims, 25 Drawing Sheets

(56) References Cited

OTHER PUBLICATIONS

Feese MD, et al. (2004) Structure of the receptor-binding domain of human thrombopoietin determined by complexation with a neutralizing antibody fragment. Proc Natl Acad Sci USA. 101(7):1816-1821.

Friesel RE, et al. (1995) Molecular mechanisms of angiogenesis: fibroblast growth factor signal transduction. FASEB J. 9(10):919-925.

Gu X, et al. (1996) Fibroblast growth factor 2 uses distinct signaling pathways for cell proliferation and cell shape changes in corneal endothelial cells. Invest Ophthalmol Vis Sci. 37(11):2326-2334.

Hormones of the Gut. (Jun. 25, 2012). Available at http://users.rcn.com/jkimball.ma.ultranet/Biology-Pages/G/GutHormones.html#secretin.

Ibrahimi OA, et al. (2004) Kinetic model for FGF, FGFR, and proteoglycan signal transduction complex assembly. Biochemistry. 43(16):4724-4730.

Jiang ZS, et al. (2002) Acute protection of ischemic heart by FGF-2: involvement of FGF-2 receptors and protein kinase C. Am J Physiol Heart Circ Physiol. 282(3):1071-1080.

Kardami E, et al. (2007) Fibroblast growth factor-2 and cardioprotection. Heart Fail Rev. 2007 12(3-4):267-277.

Kashiwakura I, et al. (2005) Fibroblast growth factor and ex vivo expansion of hematopoietic progenitor cells. Leuk Lymphoma 46(3): 329-333.

Kato T, et al. (1995) Purification and characterization of thrombopoietin. J Biochem. 118(1):229-236.

Kaushansky K, et al. (1994) Promotion of megakaryocyte progenitor expansion and differentiation by the c-Mpl ligand thrombopoietin. Nature. 369(6481):568-571.

Kaushansky K. (2005) The molecular mechanisms that control thrombopoiesis. J Clin Invest. 115(12):3339-3347.

Kinkl N, et al. (2002) Fibroblast growth factor receptor (FGFR) and candidate signaling molecule distribution within rat and human retina. Mol Vis. 8:149-160.

Klint P, et al. (1999) Contribution of Src and Ras pathways in FGF-2 induced endothelial cell differentiation. Oncogene. 18(22):3354-3364.

Koga C, et al. (1999) Characterization of a novel member of the FGF family, XFGF-20, in *Xenopus laevis*. Biochem Biophys Res Commun. 261(3):756-765.

Langley RE, et al. (1997) Radiation-induced apoptosis in microvascular endothelial cells. Br J Cancer. 75(5):666-672.

Lee HT, et al. (2003) FGF-2 induced reorganization and disruption of actin cytoskeleton through PI 3-kinase, Rho, and Cdc42 in corneal endothelial cells. Mol Vis. 9:624-634.

Lin X, et al. (2006) Synthetic peptide F2A4-K-NS mimics fibroblast growth factor-2 in vitro and is angiogenic in vivo. Int J Mol Med. 17(5):833-839.

Luoh SM, et al. (2000) Role of the distal half of the c-Mpl intracellular domain in control of platelet production by thrombopoietin in vivo. Mol Cell Biol. 20(2):507-515.

Maclachlan T, et al. (2005) Human fibroblast growth factor 20 (FGF-20; CG53135-05): a novel cytoprotectant with radioprotective potential. Int J Radiat Biol. 81(8):567-79.

Maj JG, et al. (2003) Microvascular function regulates intestinal crypt response to radiation. Cancer Res. 63(15):4338-4341.

Nichol JL, et al. (1995) Megakaryocyte growth and development factor. Analyses of in vitro effects on human megakaryopoiesis and endogenous serum levels during chemotherapy-induced thrombocytopenia. J Clin Invest. 95(6):2973-2978.

Okunieff P, et al. (1996) Differential radioprotection of three mouse strains by basic or acidic fibroblast growth factor. Br J Cancer Suppl. 27:S105-108.

Okunieff P, et al. (1998) In vivo radioprotective effects of angiogenic growth factors on the small bowel of C3H mice. Radiat Res. 150(2):204-211.

Okunieff P, et al. (1999) Circulating basic fibroblast growth factor declines during Cy/TBI bone marrow transplantation. Bone Marrow Transplant. 23(11):1117-11121.

Okunieff P, et al. (2001) Keratinocyte growth factors radioprotect bowel and bone marrow but not KHT sarcoma. Am J Clin Oncol. 24(5):491-495.

Peña LA, et al. (2000) Radiation-induced apoptosis of endothelial cells in the murine central nervous system: protection by fibroblast growth factor and sphingomyelinase deficiency. Cancer Res. Jan. 15, 2000;60(2):321-7.

RFA-AI-07-013—Medical Countermeasures to Restore Gastrointestinal Function after Radiation Exposure: Project Bioshield (RC1). (Dec. 26, 2006). *Available at http://grants.nih.gov/grants/guide/rfa-files/RFA-AI-07-013.html*.

Waselenko JK, et al. (2004) Medical management of the acute radiation syndrome: recommendations of the Strategic National Stockpile Radiation Working Group. Ann Intern Med. 140(12):1037-1051.

Zeigler FC, et al. (1994) In vitro megakaryocytopoietic and thrombopoietic activity of c-mpl ligand (TPO) on purified murine hematopoietic stem cells. Blood. 84(12):4045-4052.

Zhang L, et al. (1998) Both autocrine and paracrine effects of transfected acidic fibroblast growth factor are involved in the estrogen-independent and antiestrogen-resistant growth of MCF-7 breast cancer cells. Cancer Res.

Zhang, Kunzhong, et al. "T1847 FGF Ameliorates Radiation Injury in the Small Bowel." Gastroenterology 134.4 (2008): A-575.

* cited by examiner

SEQUENCE LISTING

<160> NUMBER OF SEQ ID NOS: 4

<210> SEQ ID NO 1
<211> LENGTH: 17
<212> TYPE: PRT
<213> ORGANISM: Artificial Sequence
<220> FEATURE:
<223> OTHER INFORMATION: Synthetic Construct

<400> SEQUENCE: 1

Cys Tyr Arg Ser Arg Lys Tyr Ser Ser Trp Tyr Val Ala Leu Lys Arg
1               5                   10                  15

Cys

<210> SEQ ID NO 2
<211> LENGTH: 27
<212> TYPE: PRT
<213> ORGANISM: Artificial Sequence
<220> FEATURE:
<223> OTHER INFORMATION: Synthetic Construct

<400> SEQUENCE: 2

Arg Phe His Ser Trp Asp Cys Ile Lys Thr Trp Ala Ser Asp Thr Phe
1               5                   10                  15

Val Leu Val Cys Tyr Asp Asp Gly Ser Glu Ala
            20                  25

<210> SEQ ID NO 3
<211> LENGTH: 15
<212> TYPE: PRT
<213> ORGANISM: Artificial Sequence
<220> FEATURE:
<223> OTHER INFORMATION: Synthetic Construct

<400> SEQUENCE: 3

Tyr Arg Ser Arg Lys Tyr Ser Ser Trp Tyr Val Ala Leu Lys Arg
1               5                   10                  15

<210> SEQ ID NO 4
<211> LENGTH: 27
<212> TYPE: PRT
<213> ORGANISM: Artificial Sequence
<220> FEATURE:
<223> OTHER INFORMATION: Synthetic Construct

<400> SEQUENCE: 4

His Ser Asp Gly Thr Phe Thr Ser Glu Leu Ser Arg Leu Gln Asp Ser
1               5                   10                  15

Ala Arg Leu Gln Arg Leu Leu Gln Gly Leu Val
            20                  25

FIBROBLAST GROWTH FACTOR (FGF) ANALOGS AND USES THEREOF

CROSS-REFERENCE TO RELATED APPLICATIONS

This application is a National Phase Application of International Application No. PCT/US2009/047498, filed Jun. 16, 2009, which claims priority to U.S. Patent Application No. 61/061,851, filed Jun. 16, 2008, which applications are incorporated herein fully by this reference.

STATEMENT REGARDING FEDERALLY SPONSORED RESEARCH

This invention is made with Government support under Grant No. AI078519 awarded by National Institute of Health. The United States Government has certain rights in this invention.

BACKGROUND OF THE INVENTION

Background Art

In the recorded human exposures tabulated in Europe and the USA, acute gastrointestinal syndrome (AGS) was a component in over 90% of cases of whole body radiation exposure (refs. 1-4). Unlike the bone marrow syndrome wherein shielding of even a portion of the marrow is greatly protective, AGS occurs even if the abdomen is sub-totally exposed. Many aspects of the mechanism and physiology of the AGS injury are well understood and therefore amenable to intervention both in a preventive mode (before exposure) and in a mitigative mode (after exposure but before symptoms). The potential of various growth factors as preventive agents and mitigators of gastroinstinal toxicity have been studied. Importantly it has been shown that 1) FGFs can protect the small bowel and reduce deaths from AGS in mice; 2) that circulating levels of FGF inversely correlate with toxicity in human ARS (bone marrow transplants); and 3) FGF's are associated with tissue repair late after radiation (humans and non-human primates). Armed with this trans-species response, FGF analogs have been explored for development as radiation protectors and mitigators.

What is needed in the art are FGF analogs with more desirable properties than native FGFs.

SUMMARY OF THE INVENTION

In accordance with the purposes of this invention, as embodied and broadly described herein, this invention, in one aspect, relates to novel polypeptide analogs of FGF.

Disclosed herein is an isolated peptide comprising the amino acid sequence

```
CYRSRKYSSWYVALKRC    (SEQ ID NO: 1).
```

Also disclosed is an isolated peptide comprising a dimer, wherein the dimer comprises SEQ ID NO: 1.

Further disclosed is a method of preventing or treating a disorder affecting rapidly proliferating tissue comprising administering to a subject an effective amount of a composition comprising SEQ ID NO: 1, thereby preventing or treating a disorder affecting rapidly proliferating tissue or one or more symptoms thereof.

Also disclosed is a method of promoting angiogenesis in a subject in need thereof, the method comprising administering to the subject an effective amount of a composition comprising SEQ ID NO: 1, thereby promoting angiogenesis in the subject.

Disclosed is a method of stimulating hematopoietic stem cell proliferation comprising administering to a subject a composition comprising the SEQ ID NO: 1, thereby stimulating hematopoietic stem cell proliferation.

Further disclosed is a method of optimizing hematopoietic stem cell engraftment comprising administering to a subject a composition comprising SEQ ID NO: 1, thereby optimizing hematopoietic stem cell engraftment.

Also disclosed is a method of stimulating gastrointestinal stem cell proliferation comprising administering to a subject a composition comprising SEQ ID NO: 1, thereby stimulating gastrointestinal stem cell proliferation Disclosed is a method to stimulate growth and proliferation of cells in a vertebrate animal comprising administering to a vertebrate subject in need of such treatment an effective amount of a composition comprising SEQ ID NO: 1, thereby stimulating growth and proliferation of cells in a vertebrate animal.

Further disclosed is a method for treating an aneurysm in a vertebrate animal comprising introducing an embolus generating vaso-occlusive device into the aneurysm, wherein the vaso-occlusive device comprises an effective amount of a composition comprising SEQ ID NO: 1, thereby treating an aneurysm in a vertebrate animal.

Also disclosed is a vaso-occlusive device, comprising an effective amount of a composition that augments fibroblast growth factor activity, which composition comprises SEQ ID NO: 1.

Disclosed is a method to treat ulcerative colitis in a vertebrate animal comprising administering to a vertebrate subject in need of such treatment an effective amount of a composition comprising SEQ ID NO: 1, thereby treating ulcerative colitis in a vertebrate animal.

Disclosed is a defined, isotonic culture medium comprising the peptide of SEQ ID NO: 1, sufficient to support growth of substantially undifferentiated mammalian stem cells.

Additional advantages of the invention will be set forth in part in the description which follows, and in part will be obvious from the description, or may be learned by practice of the invention. The advantages of the invention will be realized and attained by means of the elements and combinations particularly pointed out in the appended claims. It is to be understood that both the foregoing general description and the following detailed description are exemplary and explanatory only and are not restrictive of the invention, as claimed.

BRIEF DESCRIPTION OF THE DRAWINGS

The accompanying drawings, which are incorporated in and constitute a part of this specification, illustrate (one) several embodiment(s) of the invention and together with the description, serve to explain the principles of the invention.

FIG. 6D shows crypt numbers counted 3.5 days after 12 Gy in the ileum of Balb/c mice.

FIGS. 7B and 7C show the irradiated bowel in controls compared with FGF-P-treated Balb/c mice. The FGF-P was given at a dose of 2 mg/kg im for three daily doses beginning 15 min after irradiation. Animals were sacrificed 3.5 days after 10.5 Gy sub-TBI. 3) The plasma endotoxin level of Balb/c mice that had been exposed to 10.5 Gy sub-TBI was elevated significantly in vehicle treated groups compared to normal mice (mean 0.45 vs. 3.32 EU/mi), while the irradiated mice treated with FGF-P had a reduced endotoxin (mean 2.12 EU/ml, FIG. 7D). Amifostine (as positive control, 24) that was delivered by iv injection 30 min before 10.5 Gy IR resulted in a reduction of endotoxemia (mean 0.93 EU/ml), but it had no effect when given after irradiation (2.87 EU/ml). Similar results were obtained in C57BL/6 mice that were exposed to up to 16 Gy sub-TBI (FIG. 7E). The consistent data from two strains of mouse confirms that FGF-P can reduce endotoxemia. These data show that FGF-P is capable of partially restoring GI function following radiation exposure, which accounts for the ability of FGF-P to rescue mice from ARS.

DESCRIPTION OF THE PREFERRED EMBODIMENTS

Figure 1A:
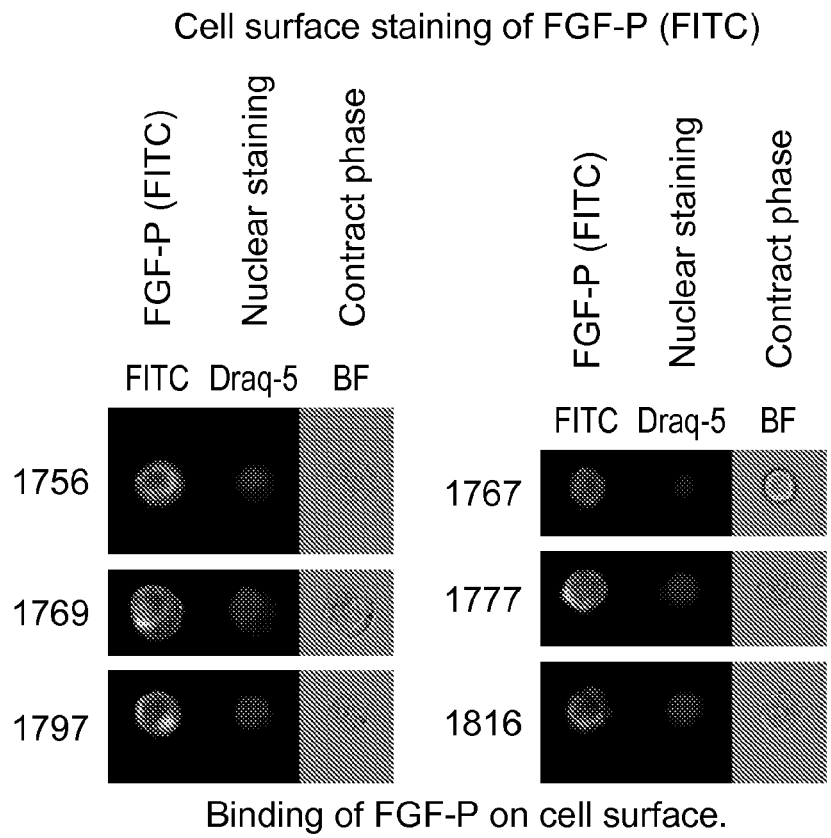
FIG. 1 shows that FGF-P is bound to the cell surface and causes the aggregation of FGFR (cluster spots) consistent with the known FGF signaling mechanism (FIG. 1A). These clusters can be counted thus allowing for measurement of relative binding coefficients. To test the feasibility of binding coefficient measurement, competition experiments were performed. Free FGF-P (30 ug/ml) was added to cells for 20 min and then the biotin-FGF-P (1 µg/mL) was added. One hour later, the streptavidin-FITC was added and analyzed by flow cytometry. The free FGF-P competed with biotin-FGF-P for cell surface binding (FIG. 1B), consistent with the specific binding. In a third test, a bioassay was performed. FGF-P was added to culture media of two types of cells: endothelial cells (adult bovine aorta endothelium) and epithelial cells (SW480, a cell line from colon). The result (FIG. 1C) showed that the FGF-P stimulated the growth of both endothelium and epithelium, a characteristic biological effect of FGF.

The present invention may be understood more readily by reference to the following detailed description of preferred embodiments of the invention and the Examples included therein and to the Figures and their previous and following description.

Before the present compounds, compositions, articles, devices, and/or methods are disclosed and described, it is to be understood that this invention is not limited to specific synthetic methods, specific treatment regimens, or to particular purification procedures, as such may, of course, vary. It is also to be understood that the terminology used herein is for the purpose of describing particular embodiments only and is not intended to be limiting.

DEFINITIONS

As used in the specification and the appended claims, the singular forms "a," "an" and "the" include plural referents unless the context clearly dictates otherwise. Thus, for example, reference to "a polypeptide" includes mixtures of polypeptides, reference to "a pharmaceutical carrier" includes mixtures of two or more such carriers, and the like.

Ranges may be expressed herein as from "about" one particular value, and/or to "about" another particular value. When such a range is expressed, another embodiment includes from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint. As used herein, "about" refers to the given value±10%.

In this specification and in the claims which follow, reference will be made to a number of terms which shall be defined to have the following meanings:

"Optional" or "optionally" means that the subsequently described event or circumstance may or may not occur, and that the description includes instances where said event or circumstance occurs and instances where it does not.

As used throughout, by "subject" is meant an individual. Preferably, the subject is a mammal such as a primate, and, more preferably, a human. Thus, the "subject" can include domesticated animals, such as cats, dogs, etc., livestock (e.g., cattle, horses, pigs, sheep, goats, etc.), and laboratory animals (e.g., mouse, rabbit, rat, guinea pig, etc.).

The term "polypeptide" is used synonymously herein with the term "peptide." Both "polypeptide" and "peptide" include a series of naturally occurring or non-naturally occurring amino acids connected by peptide bonds.

By "isolated polypeptide" or "purified polypeptide" is meant a polypeptide that is substantially free from the materials with which the polypeptide is normally associated in nature or in culture. The polypeptides of the invention can be obtained, for example, by extraction from a natural source if available (for example, a mammalian cell), by expression of a recombinant nucleic acid encoding the polypeptide (for example, in a cell or in a cell-free translation system), or by chemically synthesizing the polypeptide. In addition, polypeptide may be obtained by cleaving full length polypeptides. When the polypeptide is a fragment of a larger naturally occurring polypeptide, the isolated polypeptide is shorter than and excludes the full-length, naturally-occurring polypeptide of which it is a fragment.

The term "fragments" or "truncations" as used herein regarding FGF-P polypeptides having amino acid sequences substantially homologous thereto means a polypeptide sequence of at least 5 contiguous amino acids of FGF-P, or polypeptides having amino acid sequences substantially homologous thereto.

As used herein, the term "in combination" refers to the use of more than one therapy. The use of the term "in combination" does not restrict the order in which therapies are administered to a subject in need thereof. A first therapy can be administered prior to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks before), concomitantly with, or subsequent to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks after) the administration of a second therapy to a subject in need thereof.

As used herein, the terms "prevent," "preventing," and "prevention" refer to the prevention of the recurrence, onset, or development of a disorder associated with an insult affecting a rapidly proliferating tissue or one or more symptoms thereof in a subject resulting from the administration of a therapy, or the administration of a combination of therapies.

As used herein, the term "prophylactically effective amount" refers to the amount of a therapy which is sufficient to result in the prevention of the development, recurrence, or onset of a disease or disorder associated with an insult to rapidly proliferating tissues (such as radiation, chemotherapy, and chemical/biological warfare agents) or one or more symptoms thereof, or to enhance or improve the prophylactic effect(s) of another therapy.

As used herein, the terms "subject" and "subjects" refer to an animal, preferably a mammal, including a non-primate (e.g., a cow, pig, horse, cat, or dog), a primate (e.g., a monkey, chimpanzee, or human), and more preferably a human. In a certain embodiment, the subject is a mammal, preferably a human, who has been exposed to or is going to be exposed to an insult affecting rapidly proliferating tissues (such as radiation, chemotherapy, or chemical/biological warfare agents). In another embodiment, the subject is a farm animal (e.g., a horse, pig, or cow) or a pet (e.g., a dog or cat) which has been exposed to or is going to be exposed to a similar insult. The term "subject" is used interchangeably with "patient" in the present invention.

As used herein, the terms "treat," "treatment," and "treating" refer to the reduction of the progression, severity, and/or duration of a disorder associated with an insult affecting a rapidly proliferating tissue or amelioration of one or more symptoms thereof, wherein such reduction and/or amelioration result from the administration of one or more therapies.

As used herein, the term "therapeutically effective amount" refers to the amount of a therapy that is sufficient to reduce the severity of a disease or disorder characterized by an insult to rapidly proliferating tissues (such as radiation, chemotherapy, and chemical/biological warfare agents), reduce the duration of such a disease or disorder, prevent the advancement of such a disease or disorder, cause regression of such a disease or disorder, ameliorate one or more symptoms associated with an insult to rapidly proliferating tissues (such as radiation, chemotherapy, and chemical/biological warfare agents), or enhance or improve the therapeutic effect(s) of another therapy.

General

An FGF-2 analog named FGF-P (also referred to herein as CYRSRKYSSWYVALKRC, SEQ ID NO: 1) has been studied. This 17 amino acid peptide features the FGF receptor binding domain and a linking element to allow for receptor dimerization. The advantages of FGF-P over native FGF-2 are: 1) it is stable under severe conditions, for example to boiling; 2) it is enzyme-resistant as a dry powder and has a stable shelf-life compared to most protein drugs; 3) it can be used by victim himself via intramuscular (i.m.) injection; and 4) as a small peptide, it can be synthesized in a large quantity with high purity.

Mechanistically, many benefits of FGF-P have been shown in AGS: 1) greater proliferation of stem cells in the crypt regions; 2) improved recovery of bone marrow cellularity after TBI leading reduced endotoxemia; 3) improved day 7 and overall survival; 4) reduction of several physiologically responses including bleeding, fluid loss, diarrhea, and weight loss; and 5) beneficial changes in cytokine expression. Based on this data, it appears that FGF-P can be used as a mitigation agent for AGS. To date there are few experimental agents that satisfactorily mitigate acute radiation toxicity, and none are approved for human use. In the event of a nuclear weapon detonation at air or ground level, some radiation exposure will be due to the direct blast but more will be due to fallout or ground shine, and the vast majority who do not succumb to burns will suffer AGS as a major component of ARS (refs 5, 6). Similar estimates are reasonable from accidental or industrial exposures. This dismal picture in part arises from the early time at which complications of AGS appear compared with bone marrow syndrome. An agent that produces a dose modification factor of 1.2 or greater could potentially increase the population that survive by a 1 mile radius in case of a 2 kiloton improvised nuclear device (IND) if it is assumed 6 to 10 is the lethal dose level of GI injury (refs 5-8).

Furthermore an agent that increases the survival time can allow for successful evacuation and rescue at a distant medical facility. Thus there is need for agents that either increase the duration of survival or that modify the lethal AGS dose by 20% or more. The components of AGS include some apoptosis of the endothelial and epithelial cells of the small bowel villus (refs 5-7). It appears that the process begins within a few hours of radiation exposure, has a peak at approximately 4 to 8 hours, and returns to near baseline within 24 hours. Increased apoptotic frequency can be seen for several days after exposure. This initial apoptosis is followed by accelerated sloughing of the villus, a process that may be dominated by necrosis (refs 5, 6). The brush boarder is involved in fluid re-absorption while the crypts are involved with secretion, thus this process leads to fluid loss. Additionally, there are changes in the mucous that occur along with the change in villus structure that lead to increased bacterial translocation and can precipitate sepsis. At higher radiation doses, a decrease in crypt number per circumference can be seen, a process that is usually at maximum within 3.5 days. The decrease in crypt number begins at approximately 8 to 10 Gy and occurs in a log-linear manner at doses above this threshold. The dose response of crypts has been used for several decades as a method for measuring both the number of stem cells per crypt and the intrinsic sensitivity of the stem cells in the crypt. Death of crypt stem cells is likely a mitotic death.

There are many other factors that influence AGS, one of the most important being strain differences in tolerance. The sensitivity of the strain of mice to endotoxin, for example, likely leads to the relative sensitivity of the Balb/c mouse compared to the C57BL/6 mouse. Other events that contribute to AGS include damage to other organs such as the pancreas, stomach, and esophagus.

Insights into the processes that result in AGS elucidate opportunities for mitigation such as development of: (1) a therapy that is given in the first hours after exposure that prevents apoptosis; (2) an agent that allows survival of crypt stem cells and prevents their mitotic death or premature maturation within 3.5 days; (3) an agent that prevents the accelerated loss of brush boarder or the changes in the mucous that precipitates bacterial translocation during the first 7 days; and (4) an agent that allows for more rapid regeneration of the mucosa to reduce the impact of lymphopenia at 10 to 14 days. It is shown herein that FGF-P has many of these properties and has several logistical advantages over the native protein.

Compositions

Disclosed herein is an isolated peptide comprising the amino acid sequence CYRSRKYSSWYVALKRC (SEQ ID NO: 1). Also disclosed is an isolated nucleic acid encoding the peptide of SEQ ID NO: 1. It is understood that one way to define any known variants and derivatives or those that might arise, of the disclosed genes and proteins herein is through defining the variants and derivatives in terms of homology to specific known sequences. Specifically disclosed are variants of these and other genes and proteins herein disclosed which have at least, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99 percent homology to the stated sequence. Those of skill in the art readily understand how to determine the homology of two proteins or nucleic acids, such as genes. For example, the homology can be calculated after aligning the two sequences so that the homology is at its highest level.

Another way of calculating homology can be performed by published algorithms. Optimal alignment of sequences for comparison may be conducted by the local homology algorithm of Smith and Waterman Adv. Appl. Math. 2: 482 (1981), by the homology alignment algorithm of Needleman and Wunsch, J. MoL Biol. 48: 443 (1970), by the search for similarity method of Pearson and Lipman, Proc. Natl. Acad. Sci. U.S.A. 85: 2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by inspection.

The same types of homology can be obtained for nucleic acids by for example the algorithms disclosed in Zuker, M. *Science* 244:48-52, 1989, Jaeger et al. *Proc. Natl. Acad. Sci. USA* 86:7706-7710, 1989, Jaeger et al. *Methods Enzymol.* 183:281-306, 1989 which are herein incorporated by reference for at least material related to nucleic acid alignment.

There are a variety of sequences related to, for example, FGF-2 as well as any other protein disclosed herein that are disclosed on Genbank, and these sequences and others are herein incorporated by reference in their entireties as well as for individual subsequences contained therein.

A variety of sequences are provided herein and these and others can be found in Genbank. Those of skill in the art understand how to resolve sequence discrepancies and differences and to adjust the compositions and methods relating to a particular sequence to other related sequences. Primers and/or probes can be designed for any sequence given the information disclosed herein and known in the art.

Protein variants and derivatives are well understood to those of skill in the art and in can involve amino acid sequence modifications. For example, amino acid sequence modifications typically fall into one or more of three classes: substitutional, insertional or deletional variants. Insertions include amino and/or carboxyl terminal fusions as well as intrasequence insertions of single or multiple amino acid residues. Insertions ordinarily will be smaller insertions than those of amino or carboxyl terminal fusions, for example, on the order of one to four residues. Immunogenic fusion protein derivatives, such as those described in the examples, are made by fusing a polypeptide sufficiently large to confer immunogenicity to the target sequence by cross-linking in vitro or by recombinant cell culture transformed with DNA encoding the fusion. Deletions are characterized by the removal of one or more amino acid residues from the protein sequence. Typically, no more than about from 2 to 6 residues are deleted at any one site within the protein molecule. These variants ordinarily are prepared by site specific mutagenesis of nucleotides in the DNA encoding the protein, thereby producing DNA encoding the variant, and thereafter expressing the DNA in recombinant cell culture. Techniques for making substitution mutations at predetermined sites in DNA having a known sequence are well known, for example M13 primer mutagenesis and PCR mutagenesis. Amino acid substitutions are typically of single residues, but can occur at a number of different locations at once; insertions usually will be on the order of about from 1 to 10 amino acid residues; and deletions will range about from 1 to 30 residues. Deletions or insertions preferably are made in adjacent pairs, i.e. a deletion of 2 residues or insertion of 2 residues. Substitutions, deletions, insertions or any combination thereof may be combined to arrive at a final construct. The mutations must not place the sequence out of reading frame and preferably will not create complementary regions that could produce secondary mRNA structure. Substitutional variants are those in which at least one residue has been removed and a different residue inserted in its place. Such substitutions generally are made in accordance with the following Tables 1 and 2 and are referred to as conservative substitutions.

TABLE 1

Amino Acid Abbreviations

| Amino Acid | Abbreviations |
|---|---|
| alanine | Ala, A |
| allosoleucine | AIle |
| arginine | Arg, R |
| asparagine | Asn, N |
| aspartic acid | Asp, D |
| cysteine | Cys, C |
| glutamic acid | Glu, E |
| glutamine | Gln, K |
| glycine | Gly, G |
| histidine | His, H |
| isolelucine | Ile, I |
| leucine | Leu, L |
| lysine | Lys, K |
| phenylalanine | Phe, F |
| proline | Pro, P |
| pyroglutamic acid | Glu |
| serine | Ser, S |
| threonine | Thr, T |
| tyrosine | Tyr, Y |
| tryptophan | Trp, W |
| valine | Val, V |

TABLE 2

Amino Acid Substitutions
Original Residue Exemplary Conservative
Substitutions, others are known in the art.

Ala, ser
Arg, lys, gln
Asn, gln; his
Asp, glu
Cys, ser
Gln, asn, lys
Glu, asp
Gly, pro
His, asn; gln
Ile, leu; val
Leu, ile; val
Lys, arg; gln;
Met, Leu; ile
Phe, met; leu; tyr
Ser, thr
Thr, ser
Trp, tyr
Tyr, trp; phe
Val, ile; leu Substantial changes in function or immunological identity are made by selecting substitutions that are less conservative than those in Table 2, i.e., selecting residues that differ more significantly in their effect on maintaining (a) the structure of the polypeptide backbone in the area of the substitution, for example as a sheet or helical conformation, (b) the charge or hydrophobicity of the molecule at the target site or (c) the bulk of the side chain. The substitutions which in general are expected to produce the greatest changes in the protein properties will be those in which (a) a hydrophilic residue, e.g. seryl or threonyl, is substituted for (or by) a hydrophobic residue, e.g. leucyl, isoleucyl, phenylalanyl, valyl or alanyl; (b) a cysteine or proline is substituted for (or by) any other residue; (c) a residue having an electropositive side chain, e.g., lysyl, arginyl, or histidyl, is substituted for (or by) an electronegative residue, e.g., glutamyl or aspartyl; or (d) a residue having a bulky side chain, e.g., phenylalanine, is substituted for (or by) one not having a side chain, e.g., glycine, in this case, (e) by increasing the number of sites for sulfation and/or glycosylation.

For example, the replacement of one amino acid residue with another that is biologically and/or chemically similar is known to those skilled in the art as a conservative substitution. For example, a conservative substitution would be replacing one hydrophobic residue for another, or one polar residue for another. The substitutions include combinations such as, for example, Gly, Ala; Val, Ile, Leu; Asp, Glu; Asn, Gln; Ser, Thr; Lys, Arg; and Phe, Tyr. Such conservatively substituted variations of each explicitly disclosed sequence are included within the mosaic polypeptides provided herein.

Substitutional or deletional mutagenesis can be employed to insert sites for N-glycosylation (Asn-X-Thr/Ser) or O-glycosylation (Ser or Thr). Deletions of cysteine or other labile residues also may be desirable. Deletions or substitutions of potential proteolysis sites, e.g. Arg, is accomplished for example by deleting one of the basic residues or substituting one by glutaminyl or histidyl residues.

Certain post-translational derivatizations are the result of the action of recombinant host cells on the expressed polypeptide. Glutaminyl and asparaginyl residues are frequently post-translationally deamidated to the corresponding glutamyl and asparyl residues. Alternatively, these residues are deamidated under mildly acidic conditions. Other post-translational modifications include hydroxylation of proline and lysine, phosphorylation of hydroxyl groups of seryl or threonyl residues, methylation of the o-amino groups of lysine, arginine, and histidine side chains (T. E. Creighton, Proteins: Structure and Molecular Properties, W. H. Freeman & Co., San Francisco pp 79-86 [1983]), acetylation of the N-terminal amine and, in some instances, amidation of the C-terminal carboxyl.

It is understood that the description of conservative mutations and homology can be combined together in any combination, such as embodiments that have at least 70% homology to a particular sequence wherein the variants are conservative mutations.

It is understood that there are numerous amino acid and peptide analogs which can be incorporated into the disclosed compositions. For example, there are numerous D amino acids or amino acids which have a different functional substituent then the amino acids shown in Table 1 and Table 2. The opposite stereo isomers of naturally occurring peptides are disclosed, as well as the stereo isomers of peptide analogs. These amino acids can readily be incorporated into polypeptide chains by charging tRNA molecules with the amino acid of choice and engineering genetic constructs that utilize, for example, amber codons, to insert the analog amino acid into a peptide chain in a site specific way (Thorson et al., Methods in Molec. Biol. 77:43-73 (1991), Zoller, Current Opinion in Biotechnology, 3:348-354 (1992); Ibba, Biotechnology & Genetic Engineering Reviews 13:197-216 (1995), Cahill et al., TIBS, 14(10):400-403 (1989); Benner, TIB Tech, 12:158-163 (1994); Ibba and Hennecke, Bio/technology, 12:678-682 (1994) all of which are herein incorporated by reference at least for material related to amino acid analogs).

Molecules can be produced that resemble peptides, but which are not connected via a natural peptide linkage. For example, linkages for amino acids or amino acid analogs can include $CH_2NH$—, —$CH_2S$—, —$CH_2$—$CH_2$—$CH$=$CH$— (cis and trans), —$COCH_2$—, —$CH(OH)CH_2$—, and —$CHH_2SO$— (These and others can be found in Spatola, A. F. in Chemistry and Biochemistry of Amino Acids, Peptides, and Proteins, B. Weinstein, eds., Marcel Dekker, New York, p. 267 (1983); Spatola, A. F., Vega Data (March 1983), Vol. 1, Issue 3, Peptide Backbone Modifications (general review); Morley, Trends Pharm Sci (1980) pp. 463-468; Hudson, D. et al., Int J Pept Prot Res 14:177-185 (1979) (—$CH_2NH$—, $CH_2CH_2$—); Spatola et al. Life Sci 38:1243-1249 (1986) (—$CH H_2$—S); Hann J. Chem. Soc Perkin Trans. I 307-314 (1982) (—$CH$—$CH$—, cis and trans); Almquist et al. J. Med. Chem. 23:1392-1398 (1980) (—$COCH_2$—); Jennings-White et al. Tetrahedron Lett 23:2533 (1982) (—$COCH_2$—); Szelke et al. European Appin, EP 45665 CA (1982): 97:39405 (1982) (—$CH(OH)CH_2$—); Holladay et al. Tetrahedron. Lett 24:4401-4404 (1983) (—$C(OH)CH_2$—); and Hruby Life Sci 31:189-199 (1982) (—$CH_2$—S—); each of which is incorporated herein by reference. A particularly preferred non-peptide linkage is —$CH_2NH$—. It is understood that peptide analogs can have more than one atom between the bond atoms, such as b-alanine, g-aminobutyric acid, and the like.

Amino acid analogs and peptide analogs often have enhanced or desirable properties, such as, more economical production, greater chemical stability, enhanced pharmacological properties (half-life, absorption, potency, efficacy, etc.), altered specificity (e.g., a broad-spectrum of biological activities), reduced antigenicity, and others.

D-amino acids can be used to generate more stable peptides, because D amino acids are not recognized by peptidases and such. Systematic substitution of one or more amino acids of a consensus sequence with a D-amino acid of the same type (e.g., D-lysine in place of L-lysine) can be used to generate more stable peptides. Cysteine residues can be used to cyclize or attach two or more peptides together. This can be beneficial to constrain peptides into particular conformations. (Rizo and Gierasch Ann. Rev. Biochem. 61:387 (1992), incorporated herein by reference).

Also disclosed herein are pharmaceutical compositions comprising the peptide of SEQ ID NO: 1 or a pharmaceutically acceptable salt thereof. By "pharmaceutically acceptable" is meant a material that is not biologically or otherwise undesirable, i.e., the material may be administered to a subject, along with the nucleic acid or vector, without causing any undesirable biological effects or interacting in a deleterious manner with any of the other components of the pharmaceutical composition in which it is contained. The carrier would naturally be selected to minimize any degradation of the active ingredient and to minimize any adverse side effects in the subject, as would be well known to one of skill in the art.

The materials may be in solution, suspension (for example, incorporated into microparticles, liposomes, or cells). These may be targeted to a particular cell type via antibodies, receptors, or receptor ligands. The following references are examples of the use of this technology to target specific proteins to tumor tissue (Senter, et al., *Bioconjugate Chem.*, 2:447-451, (1991); Bagshawe, K. D., *Br. J. Cancer*, 60:275-281, (1989); Bagshawe, et al., *Br. J. Cancer*, 58:700-703, (1988); Senter, et al., *Bioconjugate Chem.*, 4:3-9, (1993); Battelli, et al., *Cancer Immunol. Immunother.*, 35:421-425, (1992); Pietersz and McKenzie, *Immunolog. Reviews*, 129: 57-80, (1992); and Roffler, et al., *Biochem. Pharmacol*, 42:2062-2065, (1991)). Vehicles such as "stealth" and other antibody conjugated liposomes (including lipid mediated drug targeting to colonic carcinoma), receptor mediated targeting of DNA through cell specific ligands, lymphocyte directed tumor targeting, and highly specific therapeutic retroviral targeting of murine glioma cells in vivo. The following references are examples of the use of this technology to target specific proteins to tumor tissue (Hughes et al., *Cancer Research*, 49:6214-6220, (1989); and Litzinger and Huang, *Biochimica et Biophysica Acta*, 1104:179-187, (1992)). In general, receptors are involved in pathways of endocytosis, either constitutive or ligand induced. These receptors cluster in clathrin-coated pits, enter the cell via clathrin-coated vesicles, pass through an acidified endosome in which the receptors are sorted, and then either recycle to the cell surface, become stored intracellularly, or are degraded in lysosomes. The internalization pathways serve a variety of functions, such as nutrient uptake, removal of activated proteins, clearance of macromolecules, opportunistic entry of viruses and toxins, dissociation and degradation of ligand, and receptor-level regulation. Many receptors follow more than one intracellular pathway, depending on the cell type, receptor concentration, type of ligand, ligand valency, and ligand concentration. Molecular and cellular mechanisms of receptor-mediated endocytosis has been reviewed (Brown and Greene, *DNA and Cell Biology* 10:6, 399-409 (1991)).

Suitable carriers and their formulations are described in *Remington: The Science and Practice of Pharmacy* (19th ed.) ed. A. R. Gennaro, Mack Publishing Company, Easton, Pa. 1995. Typically, an appropriate amount of a pharmaceutically-acceptable salt is used in the formulation to render the formulation isotonic. Examples of the pharmaceutically-acceptable carrier include, but are not limited to, saline, Ringer's solution and dextrose solution. The pH of the solution is preferably from about 5 to about 8, and more preferably from about 7 to about 7.5. Further carriers include sustained release preparations such as semipermeable matrices of solid hydrophobic polymers containing the antibody, which matrices are in the form of shaped articles, e.g., films, liposomes or microparticles. It will be apparent to those persons skilled in the art that certain carriers may be more preferable depending upon, for instance, the route of administration and concentration of composition being administered.

Pharmaceutical carriers are known to those skilled in the art. These most typically would be standard carriers for administration of drugs to humans, including solutions such as sterile water, saline, and buffered solutions at physiological pH. The compositions can be administered intramuscularly or subcutaneously. Other compounds will be administered according to standard procedures used by those skilled in the art.

Pharmaceutical compositions may include carriers, thickeners, diluents, buffers, preservatives, surface active agents and the like in addition to the molecule of choice. Pharmaceutical compositions may also include one or more active ingredients such as antimicrobial agents, antiinflammatory agents, anesthetics, and the like.

The pharmaceutical composition may be administered in a number of ways depending on whether local or systemic treatment is desired, and on the area to be treated. Administration may be topically (including ophthalmically, vaginally, rectally, intranasally), orally, by inhalation, or parenterally, for example by intravenous drip, subcutaneous, intraperitoneal or intramuscular injection. The disclosed antibodies can be administered intravenously, intraperitoneally, intramuscularly, subcutaneously, intracavity, or transdermally.

Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose), and the like. Preservatives and other additives may also be present such as, for example, antimicrobials, antioxidants, chelating agents, and inert gases and the like.

Formulations for topical administration may include ointments, lotions, creams, gels, drops, suppositories, sprays, liquids and powders. Conventional pharmaceutical carriers, aqueous, powder or oily bases, thickeners and the like may be necessary or desirable.

Compositions for oral administration include powders or granules, suspensions or solutions in water or non-aqueous media, capsules, sachets, or tablets. Thickeners, flavorings, diluents, emulsifiers, dispersing aids or binders may be desirable.

Some of the compositions may potentially be administered as a pharmaceutically acceptable acid- or base-addition salt, formed by reaction with inorganic acids such as hydrochloric acid, hydrobromic acid, perchloric acid, nitric acid, thiocyanic acid, sulfuric acid, and phosphoric acid, and organic acids such as formic acid, acetic acid, propionic acid, glycolic acid, lactic acid, pyruvic acid, oxalic acid, malonic acid, succinic acid, maleic acid, and fumaric acid, or by reaction with an inorganic base such as sodium hydroxide, ammonium hydroxide, potassium hydroxide, and organic bases such as mono-, di-, trialkyl and aryl amines and substituted ethanolamines.

Effective dosages and schedules for administering the compositions may be determined empirically, and making such determinations is within the skill in the art. The dosage ranges for the administration of the compositions are those large enough to produce the desired effect in which the symptoms disorder are effected. The dosage should not be so large as to cause adverse side effects, such as unwanted cross-reactions, anaphylactic reactions, and the like. Generally, the dosage will vary with the age, condition, sex and extent of the disease in the patient, route of administration, or whether other drugs are included in the regimen, and can be determined by one of skill in the art. The dosage can be adjusted by the individual physician in the event of any counterindications. Dosage can vary, and can be administered in one or more dose administrations daily, for one or several days. Guidance can be found in the literature for appropriate dosages for given classes of pharmaceutical products. For example, guidance in selecting appropriate doses for antibodies can be found in the literature on therapeutic uses of antibodies, e.g., Handbook of Monoclonal Antibodies, Ferrone et al., eds., Noges Publications, Park Ridge, N.J., (1985) ch. 22 and pp. 303-357; Smith et al., Antibodies in Human Diagnosis and Therapy, Haber et al., eds., Raven Press, New York (1977) pp. 365-389. A typical daily dosage of the antibody used alone might range from about 1 µg/kg to up to 100 mg/kg of body weight or more per day, depending on the factors mentioned above.

The polypeptides of the invention can be prepared using any of a number of chemical polypeptide synthesis techniques well known to those of ordinary skill in the art including solution methods and solid phase methods. Solid phase synthesis in which the C-terminal amino acid of the polypeptide sequence is attached to an insoluble support followed by sequential addition of the remaining amino acids in the sequence is one synthetic method for preparing the polypeptides. Techniques for solid phase synthesis are described by Merrifield et al., *J. Am. Chem. Soc.* 85:2149-2156 (1963). Many automated systems for performing solid phase peptide synthesis are commercially available.

Solid phase synthesis is started from the carboxy-terminal end (i.e., the C-terminus) of the polypeptide by coupling a protected amino acid via its carboxyl group to a suitable solid support. The solid support used is not a critical feature provided that it is capable of binding to the carboxyl group while remaining substantially inert to the reagents utilized in the peptide synthesis procedure. For example, a starting material can be prepared by attaching an amino-protected amino acid via a benzyl ester linkage to a chloromethylated resin or a hydroxymethyl resin or via an amide bond to a benzhydrylamine (BHA) resin or p-methylbenzhydrylamine (MBHA) resin. Materials suitable for use as solid supports are well known to those of skill in the art and include, but are not limited to, the following: halomethyl resins, such as chloromethyl resin or bromomethyl resin; hydroxymethyl resins; phenol resins, such as 4-(a-[2,4-dimethoxyphenyl]-Fmoc-aminomethyl)phenoxy resin; tert-alkyloxycarbonyl-hydrazidated resins; and the like. Such resins are commercially available and their methods of preparation are known to those of ordinary skill in the art.

The acid form of the peptides may be prepared by the solid phase peptide synthesis procedure using a benzyl ester resin as a solid support. The corresponding amides may be produced by using benzhydrylamine or methylbenzhydrylamine resin as the solid support. Those skilled in the art will recognize that when the BHA or MBHA resin is used, treatment with anhydrous hydrofluoric acid to cleave the peptide from the solid support produces a peptide having a terminal amide group.

The -amino group of each amino acid used in the synthesis should be protected during the coupling reaction to prevent side reactions involving the reactive-amino function. Certain amino acids also contain reactive side-chain functional groups (e.g. sulfhydryl, amino, carboxyl, hydroxyl, etc.) which must also be protected with appropriate protecting groups to prevent chemical reactions from occurring at those sites during the peptide synthesis. Protecting groups are well known to those of skill in the art. See, for example, *The Peptides: Analysis, Synthesis, Biology, Vol. 3: Protection of Functional Groups in Peptide Synthesis* (Gross and Meienhofer (eds.), Academic Press, N.Y. (1981)).

A properly selected-amino protecting group will render the -amino function inert during the coupling reaction, will be readily removable after coupling under conditions that will not remove side chain protecting groups, will not alter the structure of the peptide fragment, and will prevent racemization upon activation immediately prior to coupling. Similarly, side-chain protecting groups must be chosen to render the side chain functional group inert during the synthesis, must be stable under the conditions used to remove the -amino protecting group, and must be removable after completion of the peptide synthesis under conditions that will not alter the structure of the peptide.

Coupling of the amino acids may be accomplished by a variety of techniques known to those of skill in the art. Typical approaches involve either the conversion of the amino acid to a derivative that will render the carboxyl group more susceptible to reaction with the free N-terminal amino group of the peptide fragment, or use of a suitable coupling agent such as, for example, N,N'-dicyclohexylcarbodimide (DCC) or N,N'-diisopropylcarbodiimide (DIPCDI). Frequently, hydroxybenzotriazole (HOBt) is employed as a catalyst in these coupling reactions.

Generally, synthesis of the peptide is commenced by first coupling the C-terminal amino acid, which is protected at the N-amino position by a protecting group such as fluorenylmethyloxycarbonyl (Fmoc), to a solid support. Prior to coupling of Fmoc-Asn, the Fmoc residue has to be removed from the polymer. Fmoc-Asn can, for example, be coupled to the 4-(a-[2,4-dimethoxyphenyl]-Fmoc-amino-methyl)phenoxy resin using N,N'-dicyclohexylcarbodimide (DCC) and hydroxybenzotriazole (HOBt) at about 25° C. for about two hours with stirring. Following the coupling of the Fmoc-protected amino acid to the resin support, the -amino protecting group is removed using 20% piperidine in DMF at room temperature.

After removal of the -amino protecting group, the remaining Fmoc-protected amino acids are coupled stepwise in the desired order. Appropriately protected amino acids are commercially available from a number of suppliers (e.g., Novartis (Switzerland) or Bachem (Torrance, Calif.)). As an alternative to the stepwise addition of individual amino acids, appropriately protected peptide fragments consisting of more than one amino acid may also be coupled to the "growing" peptide. Selection of an appropriate coupling reagent, as explained above, is well known to those of skill in the art.

Each protected amino acid or amino acid sequence is introduced into the solid phase reactor in excess and the coupling is carried out in a medium of dimethylformamide (DMF), methylene chloride ($CH_2Cl_2$), or mixtures thereof. If coupling is incomplete, the coupling reaction may be repeated before deprotection of the N-amino group and addition of the next amino acid. Coupling efficiency may be monitored by a number of means well known to those of skill in the art. A preferred method of monitoring coupling efficiency is by the ninhydrin reaction. Peptide synthesis reactions may be performed automatically using a number of commercially available peptide synthesizers such as the Biosearch 9500™ synthesizer (Biosearch, San Raphael, Calif.).

The peptide can be cleaved and the protecting groups removed by stirring the insoluble carrier or solid support in anhydrous, liquid hydrogen fluoride (HF) in the presence of anisole and dimethylsulfide at about 0° C. for about 20 to 90 minutes, preferably 60 minutes; by bubbling hydrogen bromide (HBr) continuously through a 1 mg/10 mL suspension of the resin in trifluoroacetic acid (TFA) for 60 to 360 minutes at about room temperature, depending on the protecting groups selected; or by incubating the solid support inside the reaction column used for the solid phase synthesis with 90% trifluoroacetic acid, 5% water and 5% triethylsilane for about 30 to 60 minutes. Other deprotection methods well known to those of skill in the art may also be used.

The peptides can be isolated and purified from the reaction mixture by means of peptide purification well known to those of skill in the art. For example, the peptides may be purified using known chromatographic procedures such as reverse phase HPLC, gel permeation, ion exchange, size exclusion, affinity, partition, or countercurrent distribution.

The polypeptides of the invention can also be prepared by other means including, for example, recombinant techniques. Examples of appropriate cloning and sequencing techniques, and instructions sufficient to direct persons of skill through many cloning exercises are found in Sambrook et al. (1989) *Molecular Cloning—A Laboratory Manual* (2nd ed.) Vol. 1-3, Cold Spring Harbor Laboratory, Cold Spring Harbor Press, NY, (Sambrook).

Methods

Disclosed herein is a method of preventing or treating a disorder affecting rapidly proliferating tissue comprising administering to a subject an effective amount of a composition comprising SEQ ID NO: 1, thereby preventing or treating a disorder affecting rapidly proliferating tissue or one or more symptoms thereof. The disorder can be caused by an insult to the rapidly proliferating tissue. The insult can be radiation exposure, exposure to a chemical agent or a microorganism, or a combination thereof.

Also disclosed is a method of treating leukopenia (e.g., neutropenia) of a subject exposed to an insult affecting rapidly proliferating tissues (such as radiation, chemotherapy, and chemical/biological warfare agents with radiomimetic properties) comprising administering to the subject a therapeutically effective amount of a composition comprising one SEQ ID NO: 1.

Disclosed herein is a method of protecting and/or regenerating gastrointestinal tissues of a subject exposed to an insult affecting rapidly proliferating tissues (such as radiation, chemotherapy, and chemical/biological warfare agents with radiomimetic properties) comprising administering to the subject a therapeutically effective amount of a composition comprising SEQ ID NO: 1. For example, disclosed is a method of treating gastrointestinal mucositis of a subject exposed to an insult affecting rapidly proliferating tissues (such as radiation, chemotherapy, and chemical/biological warfare agents with radiomimetic properties) comprising administering to the subject a therapeutically effective amount of a composition comprising one or more CG53135 proteins.

Disclosed herein are methods of preventing and/or treating a disorder (e.g., alimentary mucositis, bone marrow failure, radiation induced prostatitis, virginitis and/or urethritis, a disorder of hematopoiesis, or a cardiovascular/central nervous system syndrome) or ameliorating a symptom (e.g., diarrhea, skin burn, sores, fatigue, dehydration, inflammation, hair loss, ulceration of oral mucosa, xerostomia, and bleeding) associated with an insult affecting rapidly proliferating tissues (such as radiation, chemotherapy, and chemical/biological warfare agents with radiomimetic properties) comprising administering to a subject in need thereof a prophylactically or therapeutically effective amount of SEQ ID NO: 1 or a variant thereof.

In one example, a composition comprising SEQ ID NO: 1 is administered to a subject prior to the subject's exposure to the insult. In another embodiment, a composition comprising SEQ ID NO: 1 is administered to a subject after the subject's exposure to the insult, but prior to any disorder associated with the insult, or a symptom thereof developed in the subject. In another embodiment, a composition comprising SEQ ID NO: 1 is administered to a subject after one or more disorders associated with the insult or symptoms thereof developed in the subject. In another embodiment, a composition comprising SEQ ID NO: 1 is administered a subject in need thereof both prior to the development of any radiation associated disorder and/or symptom (e.g., prior to the occurrence of the insult, and/or after the occurrence of the insult but prior to the development of any disorder and/or symptom) and after the development of a radiation associated disorder and/or symptom. In yet another embodiment, a composition comprising SEQ ID NO: 1 is administered to a subject who is at risk of exposing to an insult affecting rapidly proliferating tissues (such as radiation, chemotherapy, and chemical/biological warfare agents with radiomimetic properties).

In a specific example, a composition comprising SEQ ID NO: 1 is administered to a subject in need thereof no more than 24 hours, 20 hours, 15 hours, 10 hours, or 5 hours prior to the subject's exposure to an insult affecting rapidly proliferating tissues (e.g., radiation, chemotherapy, and chemical/biological warfare agents with radiomimetic properties). In another embodiment, a composition comprising SEQ ID NO: 1 is administered to a subject in need thereof 3 days, 2 days, 1 day prior to exposure to radiation (day −3, −2, and −1), the day exposed to radiation (day 0), and the day after exposure to the radiation (day 1), respectively. In yet another embodiment, a composition comprising SEQ ID NO: 1 is administered to a subject in need thereof on day −1, 0, and 1, respectively. Many more dosing schedules can be used, and such schedules are encompassed by the present invention.

Disclosed herein is a method of improving survival of subjects exposed to an insult affecting rapidly proliferating tissues (such as radiation, chemotherapy, and chemical/biological warfare agents with radiomimetic properties) comprising administering to the subjects a prophylactically or therapeutically effective amount of a composition comprising SEQ ID NO: 1. The therapeutically effective dose may be a single dose, two doses or more than two doses of a composition.

A single prophylactic dose of a composition comprising SEQ ID NO: 1 can be administered to a subject followed by an insult affecting rapidly proliferating tissues (such as radiation, chemotherapy, and chemical/biological warfare agents with radiomimetic properties), where such prophylactic dose causes a defined, short acting proliferative effect on various compartments in the proliferating tissues (e.g., intestinal villi). In another embodiment, more than a single prophylactic dose, which may be two or more than two doses of a composition comprising SEQ ID NO: 1, is administered to a subject exposed to an insult affecting rapidly proliferating tissues (such as radiation, chemotherapy, and chemical/biological warfare agents with radiomimetic properties) to preventing, treating or ameliorating a symptom associated with the insult.

An insult affecting rapidly proliferating tissues can be radiation exposure. In some embodiments, an insult affecting rapidly proliferating tissues is one or more alkylating agents, one or more vesicant agents (e.g., mustard agents), or one or more other chemotherapeutic agents, or a combination thereof. In some embodiments, an insult affecting rapidly proliferating tissues is a radiation exposure in combination with one or more alkylating agents, one or more mustard agents, or one or more other chemotherapeutic agents.

A composition comprising SEQ ID NO: 1 can be used in combination with one or more other therapies known in the art to prevent, treat, or ameliorate one or more symptoms associated with an insult affecting rapidly proliferating tissues (such as radiation, chemotherapy, and chemical/biological warfare agents with radiomimetic properties).

Examples of disorders that can be treated by the compositions disclosed herein include, but are not limited to, alimentary mucositis, oral mucositis, gastrointestinal mucositis, hematopoiesis, anemia, leukopenia, thrombocytopenia, pancytopenia, or a clotting disorder. The disorder can also be bone marrow failure, graft-versus-host disease, radiation induced prostatitis, virginitis, urethritis, or a cardiovascular/central nervous system syndrome.

When the subject has been exposed to radiation, the radiation exposure can result in diarrhea, skin burn, sores, fatigue, dehydration, inflammation, hair loss, ulceration of alimentary tract mucosa, xerostomia, bleeding, or a combination thereof.

Further disclosed herein is a method of promoting angiogenesis in a subject in need thereof, the method comprising administering to the subject an effective amount of a composition comprising SEQ ID NO: 1, thereby promoting angiogenesis in the subject.

The FGF-P peptide (SEQ ID NO: 1) may used for any condition, impairment, disease or syndrome for which inducing angiogenesis provides a therapeutic or palliative effect. Angiogenesis includes inducing vascularized tissue growth and physiological blood vessel formation. One particular application is angiogenesis at sites of ischemia, such as in the heart or a limb, to improve local or regional blood flow. In general, FGF-P can be employed to limit, repair or reverse damage to ischemic tissues, both internal and external. Thus, FGF-P can be employed for use in treatment of various intractable ulcers, including deep wound ulcers. Examples include bed sores, such as pressure-induced decubitus ulcers, ulcerative extremities, gangrenous extremities, diabetic ulcers and the like. Internal ulcers include oral mucosa ulcers, gastrointestinal ulcers, such as gastric ulcers, duodenal ulcers, or ulcers associated with trauma or other injury. FGF-P can also be used to restore aspects of epithelial integrity in diseases and syndromes including those characterized by inflammation of the gastrointestinal tract, including conditions such as inflammatory bowel disease, ulcerative colitis and Crohn's disease.

FGF-P (SEQ ID NO: 1) can thus be employed generally for wound healing, including surgically-induced, disease-induced and trauma-induced wounds. The peptide disclosed herein can be employed to assist in healing of muscles, skin, bone, cartilage and other tissues of the body. In surgical procedures, the peptide can be employed to limit, prevent or treat abdominal wall incisional hernias or to reduce fascial wound failure. For certain of the foregoing, it may readily be seen that sustained release peptides provide a therapeutic and practical advantage, and are included within the invention.

Injuries of the bone, which may be traumatic injuries and also include injuries resulting from diseases and degenerative conditions, that may be treated by FGF-P include fractures, open fractures, compound fractures, non-union fractures, segmental bone filling, boney voids, ischemic osteonecrosis, including avascular necrosis, and the like. FGF-P can also be employed in various orthopedic procedures, including procedures in which any device or fixture is intended to be fixed to bone, or any condition for which osteoinduction is desired. Thus, FGF-P can be employed for spinal fixation procedures using cages, rods, and other implants. FGF-P can be employed for other forms of spinal fusion and treatment of vertebral fractures and degenerative discs. FGF-P can be employed for joint replacement procedures, including but not limited to application as a coating component on joint prostheses. FGF-P can be employed for distraction osteogenesis and similar procedures for lengthening or otherwise altering bone. FGF-P can also be employed in dental applications.

Injuries of the dermis may be treated by FGF-P peptides (SEQ ID NO: 1) of the present invention, such as chemical, radiation or heat induced burns.

In another aspect, FGF-P can be employed in treatment of various cardiovascular conditions. In one aspect, therapeutic angiogenesis induced by FGF-P can serve to salvage chronically ischemic myocardium. In another aspect, FGF-P can serve to increase cardiac resistance to injury and to guard against secondary injury after an acute ischemic insult, such as at the time of reperfusion. Thus depending on the disease state and the clinical objectives, the FGF-P can be employed either acutely or chronically. In another aspect, the FGF-P peptide can serve to treat or ameliorate arterial occlusion.

In another aspect, FGF-P can be employed to improve pulmonary function in patients with emphysema and other chronic obstructive pulmonary diseases. For pulmonary applications, FGF-P can be delivered as an aerosol of microparticles, or may be administered by intratracheal means, such as using controlled-release microspheres.

In another aspect, FGF-P can be used for treatment or improvement of neurological deficits including in the treatment of Huntington's disease, Parkinson's disease, or Alzheimer's disease, and the like or after occlusive cerebrovascular disease. FGF-P can used in combination with other agents, including specifically bone marrow stromal cell transplantation.

FGF-P (SEQ ID NO: 1) can have particular application in patients with compromised or reduced immune systems, and patients with diseases, such as diabetes, in which chronic or ischemic ulcers, wounds and the like are more common or in accelerating tissue transplants in such patients.

FGF-P (SEQ ID NO: 1) can be useful as a biologically active agent for coating of medical devices, such as for instance, sutures, implants and medical instruments to promote biological responses, for instance, to stimulate growth and proliferation of cells, or healing of wounds. Recombinant basic fibroblast growth factor (rFGF-2) has been widely studied with the goal of incorporating it into clinical regimens. While FGF-2 affects many cell types, its effect on angiogenesis underlies many of therapeutic approaches for it use. It has continued to be explored for potential applications in a host of organs and diseases states. Examples of such applications include use in bone fracture healing and in bone void fillers, aneurysm healing and treatment, preparation of artificial organ implant sites and in the controversial area of therapeutic angiogenesis.

During bone repair and insufficient or interrupted angiogenic response following injury inhibits osseous regeneration and is also thought to contribute to the pathophysiology of fibrous union, osteomyelitis, and osteoradionecrosis. The importance of angiogenesis in bone repair is reinforced by the ability of anti-angiogenic compounds to inhibit ectopic bone formation and by the ability of FGF-P to accelerate bone healing.

The term "medical device" as used herein means a device that has one or more surfaces in contact with an organ, tissue, blood or other bodily fluid in an organism, preferably a mammal, particularly, a human. Medical devices include, for example, extracorporeal devices for use in surgery such as blood oxygenators, blood pumps, blood sensors, tubing used to carry blood, and the like which contact blood that is returned to the patient. The term can also include endoprostheses implanted in blood contact in a human or animal body, such as vascular grafts, stents, pacemaker leads, heart valves, and the like that are implanted in blood vessels or in the heart. The term can further include devices for temporary intravascular use such as catheters, guide wires, and the like that are placed in blood vessels or the heart for purposes of monitoring or repair. The term can further include nerve electrodes, muscle electrodes, implantable pulse generators, implantable drug pumps, and defibrillators. Moreover, the term medical device can include sutures, graft materials, wound coverings, nerve guides, bone wax, aneurysm coils, embolization particles, microbeads, dental implants, bone prostheses, tissue scaffolds, artificial joints or controlled release drug delivery devices.

The surface of the medical device can be formed from any of the commonly used materials suitable for use in medical devices, such as for instance, stainless steel, titanium, platinum, tungsten, ceramics, polyurethane, polytetrafluoroethylene, extended polytetrafluoroethylene, polycarbonate, polyester, polypropylene, polyethylene, polystyrene, polyvinyl chloride, polyamide, polyacrylate, polyurethane, polyvinyl alcohol, polycaprolactone, polylactide, polyglycolide, polysiloxanes (such as 2,4,6,8-tetramethylcyclotetrasiloxane), natural rubbers, or artificial rubbers, or block polymers or copolymers thereof.

Methods for coating biological molecules onto the surfaces of medical devices are known. See for instance U.S. Pat. No. 5,866,113 to Hendriks et al., the specification of which is hereby incorporated by reference. Tsang et al. in U.S. Pat. No. 5,955,588 teach a non-thrombogenic coating composition and methods for using the same on medical devices, and is incorporated herein by reference. Zamora et al. in U.S. Pat. No. 6,342,591 teach an amphipathic coating for medical devices for modulating cellular adhesion composition, and is incorporated herein by reference.

The FGF-P peptide (SEQ ID NO: 1) can be delivered to a mammal, the method including (i) providing a medical device coated on its surface with SEQ ID NO: 1 or a variant thereof, the peptide being bound to the surface of the medical device by non-covalent bonds; and (ii) placing the medical device onto a surface of, or implanting the medical device into, the mammal.

The medical device can be an aneurysm coil or other vaso-occlusive device, and the synthetic FGF analog of the invention serves to induce endothelial cell attachment, proliferation and/or migration, and optionally further angiogenesis, such that a permanent and substantial blockage of the blood vessel into which the aneurysm coil or other vaso-occlusive device is placed results. Aneurysm coils and vaso-occlusive devices are described in U.S. Pat. Nos. 6,866,155, 6,835,185, 6,656,218, 6,656,201, 6,638,291, 6,616,617, 6,551,305, 6,416,541, 6,383,204, 6,306,153, 6,221,066, 6,171,326, 6,168,615, 6,165,194, 6,159,165, 6,136,015 and 6,102,932, incorporated here by reference as if set forth in full.

Disclosed herein are methods of preventing and/or treating a pathology of epithelial cells and/or mesenchymal cells comprising administering to a subject in need thereof a composition comprising SEQ ID NO: 1. Also disclosed are methods of stimulating proliferation, differentiation or migration of epithelial cells and/or mesenchymal cells comprising administering to a subject in need thereof an effective amount of a composition comprising SEQ ID NO: 1.

Epithelial membranes are continuous sheets of cells with contiguous cell borders that have characteristic specialized sites of close contact called cell junction. Such membrane, which can be one or more cells thick, contain no capillaries. Epithelia are attached to the underlying connective tissue by a component known as a basement membrane, which is a layer of intercellular material of complex composition that is distributed as a thin layer between the epithelium and the connective tissue.

Stratified squamous nonkeratinizing epithelium is common on wet surfaces that are subject to considerable wear and tear at sites where absorptive function is not required. The secretions necessary to keep such surfaces wet have to come from appropriately situated glands. Sites lined by this type of epithelium include the esophagus and the floor and sides of the oral cavity.

Simple columnar epithelium is made up of a single layer of tall cells that again fit together in a hexagonal pattern. In simple secretory columnar epithelium, the columnar cells are all specialized to secret mucus in addition to being protective. Sites of this type of epithelium is present include the lining of the stomach.

A simple columnar epithelium that is made up of absorptive cells as well as secretory cells lines the intestine. To facilitate absorption, this membrane is only one cell thick. Interspersed with cells that are specialized for absorption, there are many goblet cells that secrete protective mucus.

Mesenchymal cells are stem cells that can differentiate into, e.g., osteoblasts, chondrocytes, myocytes, and adipocytes. Mesenchymal-epithelial interactions play an important role in the physiology and pathology of epithelial tissues. Messenchymal cells may associate with epithelium basement membrane (e.g., pericytes and perivascular monocyte-derived cells (MDCs)), or reside within epithelium (MDCs and T cells). The nature of the interactions between mesenchymal cells and tissue-specific cells may depend on the tissue type (e.g., brain versus epidermis), or on the prevention or allowance/stimulation of differentiation of cells into the suicidal state (apoptosis) by mesenchymal cells in a given epithelium. Specialized mesenchymal cells, such as pericytes, MDCs, and T lymphocytes, may significantly influence the differentiation and aging of epithelial cells.

The stromal compartment of the cavities of bone is composed of a net-like structure of interconnected mesenchymal cells. Stromal cells are closely associated with bone cortex, bone trabecule and to the hemopoietic cells. The bone marrow-stromal microenvironment, is a complex of cells, extracellular matrix (ECM) with growth factors and cytokines that regulate osteogenesis and hemopoiesis locally throughout the life of the individual. The role of the marrow stroma in creating the microenvironment for bone physiology and hemopoiesis lies in a specific subpopulation of the stroma cells. They differentiate from a common stem cell to the specific lineage each of which has a different role. Their combined function results in orchestration of a 3-D-architecture that maintains the active bone marrow within the bone.

In adults, blood cells are produced by the bone marrow, the spongy material filling the body's bones. The bone marrow produces two blood cell groups, myeloid and lymphoid. The myeloid cell line includes, e.g., the following: (1) Immature cells called erythrocytes that later develop into red blood cells; (2) Blood clotting agents (platelets); (3) Some white blood cells, including macrophages (which act as scavengers for foreign particles), eosinophils (which trigger allergies and also defend against parasites), and neutrophils (the main defenders against bacterial infections). The lymphoid cell line includes, e.g., the lymphocytes, which are the body's primary infection fighters. Among other vital functions, certain lymphocytes are responsible for producing antibodies, factors that can target and attack specific foreign agents (antigens). Lymphocytes develop in the thymus gland or bone marrow and are therefore categorized as either B-cells (bone marrow-derived cells) or T-cells (thymus gland-derived cells).

Disclosed herein is a method of stimulating hematopoietic stem cell proliferation comprising administering to a subject a composition comprising SEQ ID NO: 1 (FGF-P), thereby stimulating hematopoietic stem cell proliferation.

Also disclosed is a method of optimizing hematopoietic stem cell engraftment comprising administering to a subject a composition comprising SEQ ID NO: 1, thereby optimizing hematopoietic stem cell engraftment.

Further disclosed is a method of stimulating gastrointestinal stem cell proliferation comprising administering to a subject a composition comprising SEQ ID NO: 1, thereby stimulating gastrointestinal stem cell proliferation.

Disclosed is a method to stimulate growth and proliferation of cells in a vertebrate animal comprising administering to a vertebrate subject in need of such treatment an effective amount of a composition comprising SEQ ID NO: 1, thereby stimulating growth and proliferation of cells in a vertebrate animal. The cells can be crypt cells. The cells can be in the gastrointestinal tract.

Further disclosed is a method for treating an aneurysm in a vertebrate animal comprising introducing an embolus generating vaso-occlusive device into the aneurysm, wherein the vaso-occlusive device comprises an effective amount of a composition comprising SEQ ID NO: 1, thereby treating an aneurysm in a vertebrate animal.

Further disclosed is a vaso-occlusive device, comprising an effective amount of a composition that augments fibroblast growth factor activity, which composition comprises SEQ ID NO: 1.

Further disclosed is a method to treat ulcerative colitis in a vertebrate animal comprising administering to a vertebrate subject in need of such treatment an effective amount of a composition comprising SEQ ID NO: 1, thereby treating ulcerative colitis in a vertebrate animal.

Disclosed herein is a defined, isotonic culture medium comprising SEQ ID NO: 1, sufficient to support growth of substantially undifferentiated mammalian stem cells. The mammalian stem cells can be primate stem cells. The primate stem cells can be primate primordial stem cells. The primate primordial stem cells can be human primordial stem cells. The human primordial stem cells can be human embryonic stem cells.

Defined, isotonic cell culture media can be used to culture stem cells, including primate primordial stem cells, particularly human embryonic stem cells, in a substantially undifferentiated state. The media is essentially serum-free, and does not require the use of a feeder cell layer or conditioned medium from separate cultures of feeder cells, although in some embodiments it is preferred to initially culture the stem cells in a growth environment that includes allogeneic feeder cells (or conditioned medium from such cells) prior to transferring the cells to fresh, feeder-free cultures for serial passaging (e.g., 1-50 or more passages). Given its defined nature, the media can be used to investigate the developmental effects of known growth factors and other compounds added exogenously to cultures of stem cells such as substantially undifferentiated primate primordial stem cells, including stem cells that have been genetically modified. It can also be used for many other applications, including (i) to screen for compounds that can direct the developmental fate of stem cells, for example, to further promote maintenance in culture of primate primordial stem cells in a substantially undifferentiated state or to induce differentiation toward a desired cell or tissue type, or to promote de-differentiation of a primate multipotent stem cell to a pluripotent stem cell, and (ii) to culture substantially undifferentiated human primordial stem cells for use in various cell therapy applications. A more thorough description of the invention and its applications appears below.

Disclosed herein is a defined cell culture media for growing and maintaining stem cells, including primate-derived stem cells, particularly primate primordial stem cells, in a substantially undifferentiated state. In solution, the media are isotonic. In some embodiments, a medium has low osmotic pressure. FGF-P (SEQ ID NO: 1) can be used in the cell culture media.

A medium according to the invention can also include, without limitation, non-essential amino acids, an anti-oxidant, a reducing agent, growth factors, and a pyruvate salt. The base media may, for example be Dulbecco's Modified Eagle Medium (DMEM), DMEM/F-12, or KO-DMEM, each supplemented with L-glutamine or GlutaMAX™-I (provided as the dipeptide L-alanyl-L-glutamine (Invitrogen) at a final concentration of 2 mM), non-essential amino acids (1%), and 100 .mu.M .beta.-mercaptoethanol. A medium is preferably sterilized (e.g., by filtration) prior to addition to a cell culture.

Populations of stem cells (such as primate primordial stem cells) can be obtained that are 4-, 10-, 20-, 50-, 100-, 1000-, or more fold expanded when compared to the previous starting cell population. Under suitable conditions, cells in the expanded population will be 50%, 70%, or more in the undifferentiated state, as compared to the stem cells used to initiate the culture. The degree of expansion per passage can be calculated by dividing the approximate number of cells harvested at the end of the culture by the approximate number of cells originally seeded into the culture. Where geometry of the growth environment is limiting or for other reasons, the cells may optionally be passaged into a similar growth environment for further expansion. The total expansion is the product of all the expansions in each of the passages. Of course, it is not necessary to retain all the expanded cells on each passage. For example, if the cells expand two-fold in each culture, but only about 50% of the cells are retained on each passage, then approximately the same number of cells will be carried forward. But after four cultures, the cells are said to have undergone an expansion of 16-fold. Cells that are not passaged forward may be retained, if desired, in which event they may be frozen and stored, preferably in liquid nitrogen or at −140° C.

Stem cells, including primate primordial stem cells, cultured in accordance with the invention can be obtained from any suitable source using any appropriate technique. For example, procedures for isolating and growing human primordial stem cells are described in U.S. Pat. No. 6,090,622. Procedures for obtaining Rhesus monkey and other non-human primate primordial stem cells are described in U.S. Pat. No. 5,843,78 and international patent publication WO 96/22362. In addition, methods for isolating Rhesus monkey primordial stem cells are described by Thomson, et al. ((1995), Proc. Natl. Acad. Sci. USA, vol. 92:7844-7848).

Human embryonic stem cells (hESCs) can be isolated, for example, from human blastocysts obtained from human in vivo preimplantation embryos, in vitro fertilized embryos, or one-cell human embryos expanded to the blastocyst stage (Bongso, et al. (1989), Hum. Reprod., vol. 4: 706). Human embryos can be cultured to the blastocyst stage in G1.2 and G2.2 medium (Gardner, et al. (1998), Fertil. Steril., vol. 69:84). The zona pellucida is removed from blastocysts by brief exposure to pronase (Sigma). The inner cell masses can be isolated by immunosurgery or by mechanical separation, and are plated on mouse embryonic feeder layers, or in the defined culture system as described herein. After nine to fifteen days, inner cell mass-derived outgrowths are dissociated into clumps either by exposure to calcium and magnesium-free phosphate-buffered saline (PBS) with 1 mM EDTA, by exposure to dispase, collagenase, or trypsin, or by mechanical dissociation with a micropipette. The dissociated cells are then replated as before in fresh medium and observed for colony formation. Colonies demonstrating undifferentiated morphology are individually selected by micropipette, mechanically dissociated into clumps, and replated. Embryonic stem cell-like morphology is characterized as compact colonies with apparently high nucleus to cytoplasm ratio and prominent nucleoli. Resulting embryonic stem cells are then routinely split every 1-2 weeks by brief trypsinization, exposure to Dulbecco's PBS (without calcium or magnesium and with 2 mM EDTA), exposure to type IV collagenase (about 200 U/mL), or by selection of individual colonies by mechanical dissociation, for example, using a micropipette.

Once isolated, the stem cells, e.g., primate stem cells, can be cultured in a culture medium according to the invention that supports the substantially undifferentiated growth of primate primordial stem cells using any suitable cell culturing technique. For example, a matrix laid down prior to lysis of primate feeder cells (preferably allogeneic feeder cells) or a synthetic or purified matrix can be prepared using standard methods. The primate primordial stem cells to be cultured are then added atop the matrix along with the culture medium. In other embodiments, once isolated, undifferentiated human embryonic stem cells can be directly added to an extracellular matrix that contains laminin or a growth-arrested human feeder cell layer (e.g., a human foreskin fibroblast cell layer) and maintained in a serum-free growth environment according to the culture methods of invention. Unlike existing human embryonic stem cell lines cultured using conventional techniques, human embryonic stem cells and their derivatives prepared and cultured in accordance with the instant methods can be used therapeutically since they will not have been exposed to animal feeder cells, feeder-cell conditioned media, or serum at some point of their life time, thereby avoiding the risks of contaminating human cells with non-human animal cells, transmitting pathogens from non-human animal cells to human cells, forming heterogeneous fusion cells, and exposing human cells to toxic xenogeneic factors.

Alternatively, the stem cells, e.g., primate primordial stem cells, can be grown on living feeder cells (preferably allogeneic feeder cells) using methods known in the cell culture arts. The growth of the stem cells is then monitored to determine the degree to which they have become differentiated, for example, using a marker for alkaline phosphatase or telomerase or detecting the expression of the transcription factor Oct-4, or by detecting a cell surface marker indicative of an undifferentiated state (e.g., in the context of human embryonic stem cells, a labeled antibody for any one or more of SSEA-4, Tra-1-60, and Tra-1-81). When the culture has grown to confluence, at least a portion of the undifferentiated cells is passaged to another culture vessel. The determination to passage the cells and the techniques for accomplishing such passaging can be performed in accordance with the culture methods of invention (e.g., through morphology assessment and dissection procedures).

In certain preferred embodiments, the cells are cultured in a culture vessel that contains a substrate selected from the group consisting of feeder cells, preferably allogeneic feeder cells, an extracellular matrix, a suitable surface and a mixture of factors that adequately activate the signal transduction pathways required for undifferentiated growth, and a solution-borne matrix sufficient to support growth of the stem cells in solution. Thus, in addition to the components of the solution phase of culture media of the invention, the growth environment includes a substrate selected from the group consisting of primate feeder cells, preferably allogeneic feeder cells, and an extracellular matrix, particularly laminin. Preferred feeder cells for primate primordial stem cells include primate fibroblasts and stromal cells. In preferred embodiments, the feeder cells and stem cells are allogeneic. In the context of human embryonic stem cells, particularly preferred feeder cells include human fibroblasts, human stromal cells, and fibroblast-like cells derived from human embryonic stem cells. If living feeder cells are used, as opposed to a synthetic or purified extracellular matrix or a matrix prepared from lysed cells, the cells can be mitotically inactivated (e.g., by irradiation or chemically) to prevent their further growth during the culturing of primate primordial stem cells. Inactivation is preferably performed before seeding the cells into the culture vessel to be used. The primate primordial stem cells can then be grown on the plate in addition to the feeder cells. Alternatively, the feeder cells can be first grown to confluence and then inactivated to prevent their further growth. If desired, the feeder cells may be stored frozen in liquid nitrogen or at −140° C. prior to use. As mentioned, if desired such a feeder cell layer can be lysed using any suitable technique prior to the addition of the stem cells (e.g., primate stem cells) so as to leave only an extracellular matrix.

Any suitable culture vessel can be adapted to culture stem cells (e.g., primate primordial stem cells) in accordance with the invention. For example, vessels having a substrate suitable for matrix attachment include tissue culture plates (including multi-well plates), pre-coated (e.g., gelatin-pre-coated) plates, T-flasks, roller bottles, gas permeable containers, and bioreactors. To increase efficiency and cell density, vessels (e.g., stirred tanks) that employ suspended particles (e.g., plastic beads or other microcarriers) that can serve as a substrate for attachment of feeder cells or an extracellular matrix can be employed. In other embodiments, undifferentiated stem cells can be cultured in suspension by providing the matrix components in soluble form. As will be appreciated, fresh medium can be introduced into any of these vessels by batch exchange (replacement of spent medium with fresh medium), fed-batch processes (i.e., fresh medium is added without removal of spent medium), or ongoing exchange in which a proportion of the medium is replaced with fresh medium on a continuous or periodic basis.

The defined cell culture media and methods for growing stem cells, particularly primate primordial stem cells, in a substantially undifferentiated state in accordance with the present invention will be seen to be applicable to all technologies for which stem cell lines are useful. Of particular importance is the use of the instant cell culture media and methods of culturing, for example, primate primordial stem cells in screening to identify growth factors useful in culturing primate stem cells in an undifferentiated state, as well as compounds that induce such cells to differentiate toward a particular cell or tissue lineage. The instant invention also allows genetically modified stem cells to be developed, as well as the creation of new stem cell lines, especially new primate primordial stem cell lines. The establishment of new cell lines according to the invention includes normal stem cell lines, as well as abnormal stem cell lines, for example, stem cell lines that carry genetic mutations or diseases (e.g., stem cells infected with a pathogen such as a virus, for example, HIV). Cells produced using the media and methods of the invention can also be mounted on surfaces to form biosensors for drug screening. The invention also provides for the capacity to produce, for example, commercial grade undifferentiated primate primordial stem cells (e.g., human ESCs) on a commercial scale. As a result, stem cells such as primate primordial stem cells produced in accordance with the present invention will have numerous therapeutic and diagnostic applications. In other applications, substantially undifferentiated hESCs can be used. Several representative examples of such applications are provided below.

An aspect of the present invention involves screens for identifying growth factors that promote or inhibit the differentiation, growth, or survival of stem cells such as primate primordial stem cells in serum-free, feeder-free culture, as well as factors that promote the differentiation of such cells. Such systems have the advantage of not being complicated by secondary effects caused by perturbation of the feeder cells by the test compounds. In some embodiments, primate primordial stem cells are used as a primary screen to identify substances that promote the growth of primate primordial stem cells in a substantially undifferentiated state. Such screens are performed by contacting the stem cells in culture with one test compound species (or, alternatively, pools of different test compounds). The effect of exposing the cells to the test compound can then be assessed using any suitable assay, including enzyme activity-based assays and reporter/antibody-based screens, e.g., to detect the presence of a marker correlated with an undifferentiated state. Such assays can be either qualitative or quantitative in terms of their read out. Suitable enzyme activity assays are known in the art (e.g., assays based on alkaline phosphatase or telomerase activity), as are antibody-based assays, any of which may readily be adapted for such applications. Of course, any other suitable assay may also be employed, depending on the result being sought.

With regard to antibody-based assays, polyclonal or monoclonal antibodies may be obtained that are specifically reactive with a cell surface marker that is correlated with totipotency or pluripotency. Such antibodies can be labeled. Alternatively, their presence may be detected by a labeled secondary antibody (e.g., a fluorescently labeled, rabbit-derived anti-mouse antibody that reacts with mouse-derived antibodies), as in a standard ELISA (Enzyme-Linked ImmunoSorbent Assay). If desired, labeled stem cells can also be sorted and counted using standard methods, e.g., fluorescence-activated cell sorting ("FACS").

In one embodiment of such a primary screen, the presence of increased alkaline phosphatase activity (indicative of an undifferentiated state) indicates that the test compound is a growth factor. In other embodiments, increased percentages of cells with continued expression of one or more markers indicative of an undifferentiated state (e.g., Oct-4, SSEA-4, Tra-1-60, and Tra-1-81) following exposure to a test compound indicates that the test compound is a growth factor. Serial or parallel combinations of such screens (e.g., an alkaline phosphatase-based screen followed by, or alternatively coupled with, a screen based on expression of Oct-4, SSEA-4, Tra-1-60, and Tra-1-81) may also be employed. Substances that are found to produce statistically significant promotion of growth of the stem cells in an undifferentiated state can then be re-tested, if desired. They can also be tested, for example, against primordial stem cells from other primate species to determine if the growth factor exerts only species-specific effects. Substances found to be effective growth factors for primate stem cells can also be tested in combinations to determine the presence of any synergistic effects.

Such assays can also be used to optimize the culture conditions for a particular type of stem cell, such as primate primordial stem cells (e.g., human ESCs).

In addition to screening for growth factors, stem cells cultured in accordance with the invention can also be used to identify other molecules useful in the continued culture of the cells in a substantially undifferentiated state, or alternatively, which stimulate a change in the developmental fate of a cell. Such changes in developmental fate include inducing differentiation of the stem cell toward a desired cell lineage. In other embodiments, the developmental change stimulated by the molecule may be de-differentiation, such that following exposure to the test compound, the cells become more primitive, in that subsequent to exposure, they have the capacity to differentiate into more cell types than was possible prior to exposure. As will be appreciated, such methods allow the evaluation of any compound for such an effect, including compounds already known to play important roles in biology, e.g., proteins, carbohydrates, lipids, and various other organic and inorganic molecules found in cells or which affect cells.

Feeder-free, serum-free cultures of stem cells such as primate primordial stem cells can also be used in drug discovery processes, as well as for testing pharmaceutical compounds for potential unintended activities, as might cause adverse reactions if the compound was administered to a patient. Assessment of the activity of pharmaceutical test compounds generally involves combining the cells of the invention with the test compound, determining any resulting change, and then correlating the effect of the compound with the observed change. The screening may be done, for example, either because the compound is designed to have a pharmacological effect on certain cell types, or because a compound designed to have effects elsewhere may have unintended side effects. Two or more drugs (or other test compounds) can also be tested in combination (by combining with the cells either simultaneously or sequentially) to detect possible drug-drug interaction effects. In some applications, compounds are screened initially for potential toxicity. See generally "In vitro Methods in Pharmaceutical Research," Academic Press, 1997. Cytotoxicity can be determined by the effect on cell viability, survival, morphology, on the expression or release of certain markers, receptors or enzymes, and/or on DNA synthesis or repair, measured by [3H]-thymidine or BrdU incorporation.

Primate primordial stem cells (or other stem cells) cultured according to this invention can be used to prepare populations of differentiated cells of various commercially and therapeutically important tissue types. In general, this is accomplished by expanding the stem cells to the desired number. Thereafter, they are caused to differentiate according to any of a variety of differentiation strategies.

Primate primordial stem cells can also be used to generate cells that have characteristic markers of cardiomyocytes and spontaneous periodic contractile activity. Differentiation in this way is facilitated by nucleotide analogs that affect DNA methylation (such as 5-aza-deoxy-cytidine), growth factors, and bone morphogenic proteins. The cells can be further enriched by density-based cell separation, and maintained in media containing creatine, carnitine, and taurine.

Additionally, stem cells such as primate primordial stem cells can be directed to differentiate into mesenchymal cells in a medium containing a bone morphogenic protein (BMP), a ligand for the human TGF-β receptor, or a ligand for the human vitamin D receptor. The medium may further comprise dexamethasone, ascorbic acid-2-phosphate, and sources of calcium and phosphate. In preferred embodiments, derivative cells have phenotypic features of cells of the osteoblast lineage.

As will be appreciated, differentiated cells derived from stem cells such as primate primordial stem cells cultured in accordance with the methods of the invention can be also be used for tissue reconstitution or regeneration in a human patient in need thereof. The cells are administered in a manner that permits them to graft to the intended tissue site and reconstitute or regenerate the functionally deficient area. For instance, neural precursor cells can be transplanted directly into parenchymal or intrathecal sites of the central nervous system, according to the disease being treated. The efficacy of neural cell transplants can be assessed in a rat model for acutely injured spinal cord, as described by McDonald, et al. ((1999) Nat. Med., vol. 5:1410) and Kim, et al. ((2002) Nature, vol. 418:50). Successful transplants will show transplant-derived cells present in the lesion 2-5 weeks later, differentiated into astrocytes, oligodendrocytes, and/or neurons;

and migrating along the spinal cord from the lesioned end, and an improvement in gait, coordination, and weight-bearing.

Similarly, the efficacy of cardiomyocytes can be assessed in a suitable animal model of cardiac injury or dysfunction, e.g., an animal model for cardiac cryoinjury where about 55% of the left ventricular wall tissue becomes scar tissue without treatment (Li, et al. (1996), Ann. Thorac. Surg., vol. 62:654; Sakai, et al. (1999), Ann. Thorac. Surg., vol. 8:2074; Sakai, et al. (1999), J. Thorac. Cardiovasc. Surg., vol. 118:715). Successful treatment will reduce the area of the scar, limit scar expansion, and improve heart function as determined by systolic, diastolic, and developed pressure (Kehat, et al. (2004)). Cardiac injury can also be modeled, for example, using an embolization coil in the distal portion of the left anterior descending artery (Watanabe, et al. (1998), Cell Transplant., vol. 7:239), or by ligation of the left anterior descending coronary artery (Min, et al. (2002), J. Appl. Physiol., vol. 92:288). Efficacy of treatment can be evaluated by histology and cardiac function. Cardiomyocyte preparations embodied in this invention can be used in therapy to regenerate cardiac muscle and treat insufficient cardiac function.

Liver function can also be restored by administering hepatocytes and hepatocyte precursors differentiated from, for example, primate pluripotent stem cells grown in accordance with this invention. These differentiated cells can be assessed in animal models for ability to repair liver damage. One such example is damage caused by intraperitoneal injection of D-galactosamine (Dabeva, et al. (1993), Am. J. Pathol., vol. 143:1606). Treatment efficacy can be determined by immunocytochemical staining for liver cell markers, microscopic determination of whether canalicular structures form in growing tissue, and the ability of the treatment to restore synthesis of liver-specific proteins. Liver cells can be used in therapy by direct administration, or as part of a bioassist device that provides temporary liver function while the subject's liver tissue regenerates itself, for example, following fulminant hepatic failure.

The present invention also provides methods for producing, for example, primate stem cell lines having one or more genetic modifications. As is apparent to one of ordinary skill in the art, altered expression of gene products can be achieved by modifying the coding sequence of a gene product or by altering flanking regions of the coding sequence. Thus, as used herein, the terms "genetic modification" and the like include alterations to the sequence encoding a gene product, as well as alterations to flanking regions, in particular to the 5' upstream region of the coding sequence (including the promoter). Similarly, the term "gene" encompasses all or part of the coding sequence and the regulatory sequences that may be present flanking the coding sequence, as well as other sequences flanking the coding sequence. Genetic modifications may be permanent or transient. Preferred permanent modifications are those that do not adversely affect chromosome stability or cell replication. Such modifications are preferably introduced by recombination or otherwise by insertion into a chromosome (as may be mediated, for example, by an engineered retroviral vector). Transient modifications are generally obtained by introducing an extrachromosomal genetic element into a cell by any suitable technique. Regardless of the permanence of a particular genetic modification, in embodiments wherein one or more genes are introduced, their expression may be inducible or constitutive. The design, content, stability, etc. of a particular genetic construct made for use in practicing the invention is left to the discretion of the artisan, as these will vary depending on the intended result.

After introducing a desired genetic modification, a particularly effective way of enriching genetically modified cells is positive selection using resistance to a drug such as neomycin. To accomplish this, the cells can be genetically altered by contacting them simultaneously with a vector system harboring the gene(s) of interest and a vector system that provides the drug resistance gene. Alternatively, the drug resistance gene can be built into the same vector as the gene(s) of interest. After transfection has taken place, the cultures are treated with the corresponding drug, and untransfected cells are eliminated.

According to this aspect, genetically modified stem cells such as primate primordial stem cells are grown using a cell culture medium of the invention. One or more genes or nucleic acid molecules are introduced into, or one or more genes are modified in, these cells to produce a clone population having the desired genetic modifications. Depending upon the genetic modification(s) made, the cells may continue to be propagated in a substantially undifferentiated state in accordance with the invention. Alternatively, they may be allowed (or induced) to differentiate. Primate-derived primordial stem cells having such genetic modifications have important applications, especially with respect to applications where euploid primate cells having genetic modifications are useful or required. Examples of such applications include, but are not limited to, the development of cell-based models for primate, especially human, diseases, as well as the development of specialized tissues for transplantation. Genetically modified stem cells cultured in accordance with the invention, including primate primordial stem cells, especially human embryonic stem cells, also have many other therapeutic applications, including in gene therapy (e.g., to compensate for a single gene defect), and as tissue for grafting or implantation, and to treat other diseases and disorders. Examples of diseases caused by single gene defects include myotonic dystrophy, cystic fibrosis, sickle cell anemia, Tay Sachs disease, and hemophilia.

For therapeutic application, cells prepared according to this invention (be they totipotent or pluripotent cells or differentiated cells derived therefrom) are typically supplied in the form of a pharmaceutical composition comprising an isotonic excipient, and are prepared under conditions that are sufficiently sterile for human administration. For general principles in medicinal formulation of cell compositions, see "Cell Therapy: Stem Cell Transplantation, Gene Therapy, and Cellular Immunotherapy," by Morstyn & Sheridan eds, Cambridge University Press, 1996; and "Hematopoietic Stem Cell Therapy," E. D. Ball, J. Lister & P. Law, Churchill Livingstone, 2000. The cells may be packaged in a device or container suitable for distribution or clinical use, optionally accompanied by information relating to use of the cells in tissue regeneration or for restoring a therapeutically important metabolic function.

EXPERIMENTAL

The following examples are put forth so as to provide those of ordinary skill in the art with a complete disclosure and description of how the compounds, compositions, articles, devices and/or methods claimed herein are made and evaluated, and are intended to be purely exemplary of the invention and are not intended to limit the scope of what the inventors regard as their invention. Efforts have been made to ensure accuracy with respect to numbers (e.g., amounts, temperature, etc.), but some errors and deviations should be accounted for. Unless indicated otherwise, parts are parts by weight, temperature is in ° C. or is at ambient temperature, and pressure is at or near atmospheric.

Example 1

FGF-P

Role of Acidic FGF (FGF-1) and Basic FGF (FGF-2) as Prevention and Mitigation Agents for Bone Marrow and Gastrointestinal Syndromes All the animal experiments described herein feature human FGFs used in murine models. Both FGF-1 and FGF-2 are radiation protectors of the bone marrow and of the small bowel. In the case of the bone marrow, the stroma is probably the target. FGF-2 outperforms FGF-1 by a small margin, and the process is modal with a peak advantage seen at approximately 6 μg/mouse intravenously (iv) or intramuscularly (im). Delivery iv or im is more beneficial than subcutaneous which, in turn, is better than intraperitoneal. FGFs in general bind heparin, but delivery of FGF with heparin decreases the benefit though it increases the plasma half-life. The nadir of marrow cellularity does not seem to be affected by FGF. The benefit from FGF arises from the rapid recovery of the marrow and an associated decreased period of marrow aplasia.

FGF-1 and to a greater extent FGF-2 are effective after irradiation as mitigators of AGS. The benefit is less if the FGF-2 is delayed more than 24 hours after irradiation or is given more than 48 hours before irradiation. This timing gives insight into the frequency that FGF must be administered (daily doses seem to be optimal). Extensive studies of AGS in mice treated with FGFs (9-13) FGF-1 and FGF-2 has revealed that both radioprotect when given before irradiation, as measured by either the LD50/7 or crypt assay. Both agents can also be given 1 hour after irradiation with little or no decrease in efficacy. Here again there is a modal response with a peak response at approximately 6 μg/mouse. The benefit is lost if the dose is increased beyond approximately 24 μg/mouse. The optimal time of FGF delivery is 24 hours before exposure, in prevention experiments. In mitigation experiments, multiple doses given daily for three days beginning with an initial dose at 1 hr after exposure appears optimal. Finally, combinations of FGF with KGF-1 (aka FGF-7) or KGF-2 (aka FGF-10) have additive benefit.

Other benefits of FGF-2 are improved bone growth in young mice exposed to limb irradiation. Here FGF-2 was given 3 times each week at a dose of 6 μg/mouse/dose iv (9, 10). The FGF-2 was initiated either the day after radiation and continued for 4 weeks or was initiated on week 5 and continued to week 8. Substantial reparation of growing potential of the limb was achieved by early administration of FGF-2 even when the agent was begun one month after irradiation. Thus FGF-2 has the potential to mitigate damage at late times after radiation exposure in a number of organs. Circulating FGF-2 has been measured in patients undergoing total body radiation. In these studies the patients are given radiation at 1.7 Gy BID for 4 days. A substantial continuous decline in FGF-2 levels was found in the circulation (12, 14). A dramatic decline in normal circulating levels FGF-2 can even be seen in patients exposed to partial body radiation. The patients with the greatest decrease in FGF-2 report anorexia even when the abdomen was not included in the radiation field (12, 14).

The levels of circulating FGF-2 in Rhesus monkeys at late times following exposure to 12.5 Gy delivered in two 6.25 Gy doses given 6 hours apart was studied. Surviving primates can go on to hepato-renal syndromes that are followed, compensatorily, by elevations in FGF-2 in an incomplete attempt to repair the microvascular damage.

Finally, it has been shown that FGF-2 levels can be very high in patients who develop late complications of radiation (12, 14). In this case, the FGF is attempting to overcome a radiation-induced inflammatory process that is acting locally in the damaged tissue and preventing normal angiogenesis and repair. Therapy for the complication resulted in a reduction of the FGF-2 levels in the circulation (12, 14).

Taken together, it has been shown that the FGF family, in particular FGF-2, has great promise across species. FGF-2 is commonly found below detectable levels in humans exposed to irradiation, and is involved in the repair processes that are still occurring long after radiation exposure. There are also some unknown factors. The modal response suggests differential receptor binding, and similarly the differential responses between some strains of mice requires better understanding if to know the human subjects most likely to benefit from FGF-2 therapy.

Synthesis and Design Considerations for FGF-P

FGF-2 has domains that bind to the FGF receptor and another for heparin binding. An essential component of the biological activity is the heparin-mediated dimerization of the FGF receptors (15-17). There are 4 main FGF receptors (FGFR), but multiple splice variants, especially in exon III of the receptors (corresponding to the FGFR protein domain D3) add to the complexity. Many cell and animal systems confirm a modal biological response wherein increases of FGF lead to a peak and then decline in response. The mechanism of that modal response is assumed to be the dimerization of inactive receptor complexes. For this the receptor 2, being the most promiscuous, has been suggested. In most cases, FGFR activation acts as a strong mitogen to stimulate cell proliferation and inhibit apoptosis (18). Since FGFRs are expressed on the surface of many types of cells, FGF-2 exerts a broad range of biological functions including stem cell proliferation, cell differentiation, angiogenesis, and tissue repair (17-19).

Stability and deployability are significant biological factors that must be considered in evaluating countermeasures for radiological terror. Synthetic peptides solve some of the problems inherent with recombinant cytokine proteins It has been found that the 10-amino acid stretch in the first receptor-binding domain of bFGF has high affinity to FGFR1III (15-19). Based on this, synthetic peptides that mimic FGF-2 have been developed. These stable peptides are: F2A3 (RFHSWD-CIKTWASDTFVLVCYDDGSEA, SEQ ID NO: 2) and F2A4 (YRSRKYSSWYVALKR, SEQ ID NO: 3), which bind with high specificity to a cytokine receptor, and via another domain bind to heparin, connected by a spacer with useful chemical characteristics. When the peptides are premixed with heparin, a bimolecular complex is formed, and it is this complex that can activate a receptor. The binding of F2A3 and F2A4 to FGF receptor is equivalent to native bFGF and can trigger the downstream signaling as effectively as bFGF. In addition, when applied to bovine aortic endothelial cells in vitro, F2A3/F2A4 trigger cell proliferation and block radiation-induced apoptosis similar to bFGF. In animals, F2A3/F2A4 exhibit radio-protective effects similar to bFGF (20-22).

More recently a biologically stable proprietary FGF-2 analog has been designed, termed FGF-P. FGF-P is a small peptide that consists of a FGFR binding domain and a dimer link as well as end protection to reduce peptidase digestion. It provides excellent in vivo efficacy for protection and mitigation of AGS. It is stable as a liquid even with boiling. FGF-P was chemically synthesized and purified using HPLC by a specialized peptide synthesis company (Metagene Inc). The sequence includes a leucine that can be replaced with a dehydroleucine for tritium labeling.

In Vitro Characterization of FGF-P Effects

Three preliminary experiments were carried out using FGF-P in vitro to confirm its activity. First, the biotin conjugated FGF-P was used as a tool to examine for cell surface binding. AsPC-1 pancreatic cancer epithelial cells are known to have high levels of FGFR and were used for this study. ASPC1 cells were incubated with 1 μg/ml of biotin-FGF-P and then labeled with streptavidin-FITC. The cells were then analyzed using an imaging flow cytometer (Amnis Imagestream). This device can image each cell as it passes through the laser, it can then sort cells according to both staining and morphological characteristics.

Figure 1B:
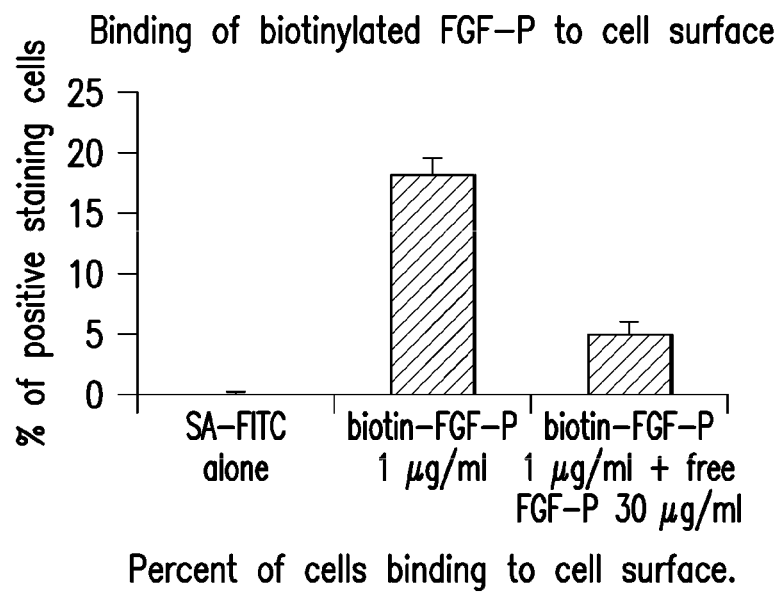

It was found that FGF-P is bound to the cell surface and causes the aggregation of FGFR (cluster spots) consistent with the known FGF signaling mechanism FIG. 1A. These clusters can be counted thus allowing for measurement of relative binding coefficients. To test the feasibility of binding coefficient measurement, competition experiments were performed. Free FGF-P (30 ug/ml) was added to cells for 20 min and then the biotin-FGF-P (1 μg/mL) was added. One hour later, the streptavidin-FITC was added and analyzed by flow cytometry. The free FGF-P competed with biotin-FGF-P for cell surface binding (FIG. 1B), consistent with the specific binding. In a third test, a bioassay was performed. FGF-P was added to culture media of two types of cells: endothelial cells (adult bovine aorta endothelium) and epithelial cells (SW480, a cell line from colon). The result (FIG. 1C) showed that the FGF-P stimulated the growth of both endothelium and epithelium, a characteristic biological effect of FGF.

In Vivo Mitigation Effect of FGF-P on AGS

A sub-TBI (total body irradiation) model was created, in which one leg of mouse is shielded from the direct radiation field. With this system, 8.5 Gy can be delivered to Balb/c mice without BM deaths (defined as deaths that occur between 10 and 30 days). When sub-TBI dose was increased to 9 Gy, half the irradiated mice die, and at 10.5 Gy, 66-100% mice died within 5-7 days. Pathologically these mice have devastating gut damage. In our GI (sub-TBI) model, the LD50/7 for Balb/c mice (6-8 week old from NCI) was 8.9-9.1 Gy. Using this GI model, the mitigation effect of FGF-P on the GI syndrome was tested. FGF-P (2 mg/kg) was given im 5-10 minutes after IR and continued once a day for 3-5 consecutive days. Each animal experiment had its own vehicle mock treatment group as control.

Figure 2:
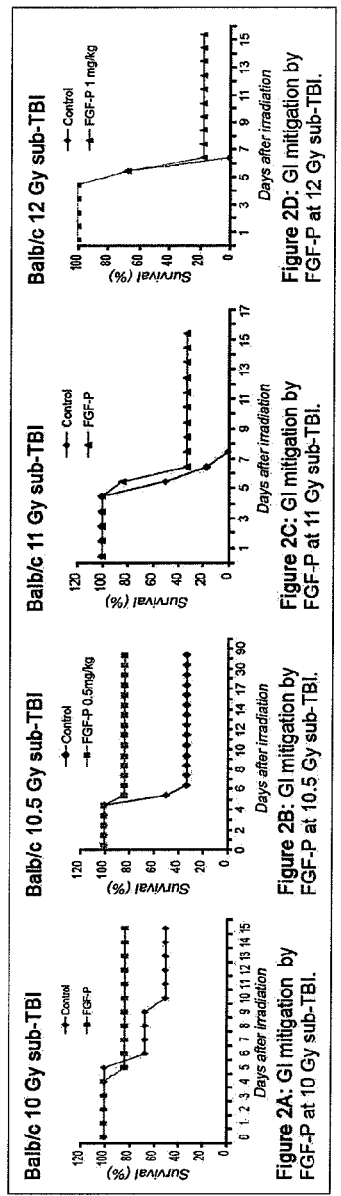
FIG. 2 shows that when Balb/c mice received sub-TBI of 10 Gy, >50% of control mice died within 7 days (LD50/7) while 87% of mice treated with FGF-P were still alive at 4 months (FIG. 2A). When the sub-TBI dose is raised to 10.5 or 11 Gy, 100% of the untreated control mice died of GI syndrome, while 33-67% of mice treated with FGF-P survived 3.5 months, FIGS. 2B and 2C). When the IR dose was raised to 12 Gy, all control animals died and 17% of FGF-P treated mice survived (FIG. 2D). The Kaplan Meier analysis indicated that all the differences between the vehicle alone and FGF-P treatment groups were statistically significant ($P<0.05$). All the data show that FGF-P given after an otherwise lethal AGS dose produced a mitigative effect. Additionally, many of the animals that do die, do so later than mice not treated with FGF-P.

When Balb/c mice receive sub-TBI of 10 Gy, >50% of control mice died within 7 days (LD50/7) while 87% of mice treated with FGF-P were still alive at 4 months (FIG. 2A). When the sub-TBI dose is raised to 10.5 or 11 Gy, 100% of the untreated control mice died of GI syndrome, while 33-67% of mice treated with FGF-P survived 3.5 months, FIGS. 2B and 2C). When the IR dose was raised to 12 Gy, all control animals died and 17% of FGF-P treated mice survived (FIG. 2D). The Kaplan Meier analysis indicated that all the differences between the vehicle alone and FGF-P treatment groups were statistically significant (P<0.05). All the data show that FGF-P given after an otherwise lethal AGS dose produced a mitigative effect. Additionally, many of the animals that do die, do so later than mice not treated with FGF-P.

FGF-P Rescued Mice of Multiple Strains from Lethal AGS

Figure 3:
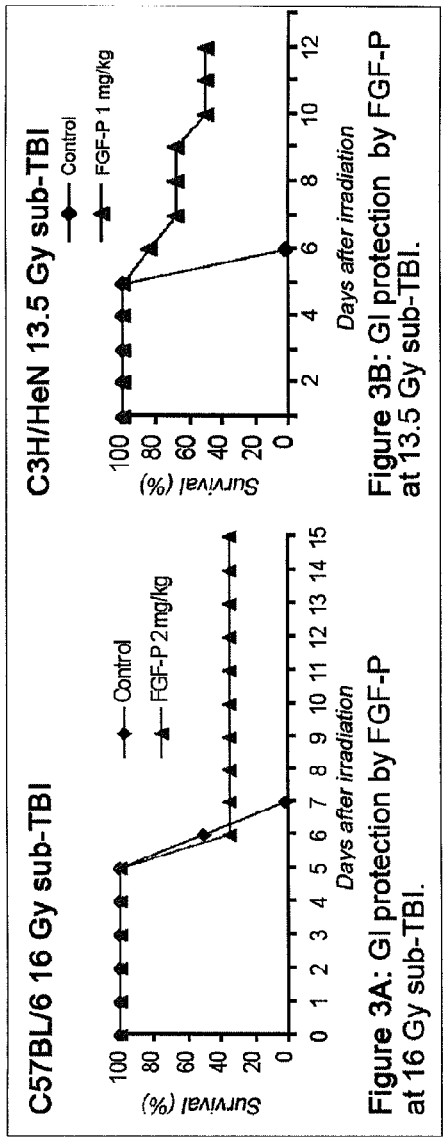
FIG. 3 shows that to determine if the agent works in mice with different genomic backgrounds, FGF-P (2 mg/kg) was given to C57BL/6 mice 10 min after the mice were exposed to 16 Gy sub-TBI. While none of the irradiated control mice survived (LD50/7 about 13.5 Gy), 33% of mice treated with FGF-P were still alive at 1.5 months (FIG. 3A). A third strain of mouse, C3H/HeN (LD50/7 about 12 Gy), was also studied. At 12.5 Gy sub-TBI, 33% of control mice survived while 50% of mice treated with FGF-P survived. At 13.5 Gy, all the control mice died within 7 days, while 50% of FGF-P treated mice survived (FIG. 3B).

Native FGF-2 has a mouse strain dependent response profile. Most strains enjoy a benefit, but responses in C57 mice have been unimpressive. To determine if the agent works in mice with different genomic backgrounds, FGF-P (2 mg/kg) was given to C57BL/6 mice 10 min after the mice were exposed to 16 Gy sub-TBI. While none of the irradiated control mice survived (LD50/7 about 13.5 Gy), 33% of mice treated with FGF-P were still alive at 1.5 months (FIG. 3A). A third strain of mouse, C3H/HeN (LD50/7 about 12 Gy), was also studied. At 12.5 Gy sub-TBI, 33% of control mice survived while 50% of mice treated with FGF-P survived. At 13.5 Gy, all the control mice died within 7 days, while 50% of FGF-P treated mice survived (FIG. 3B). Thus unlike native FGF the bioavailability or bioeffect of FGF-P seems to be strain independent.

FGF-P Rescued Mice from Death of BM (Bone Marrow) Syndrome

Figure 4:
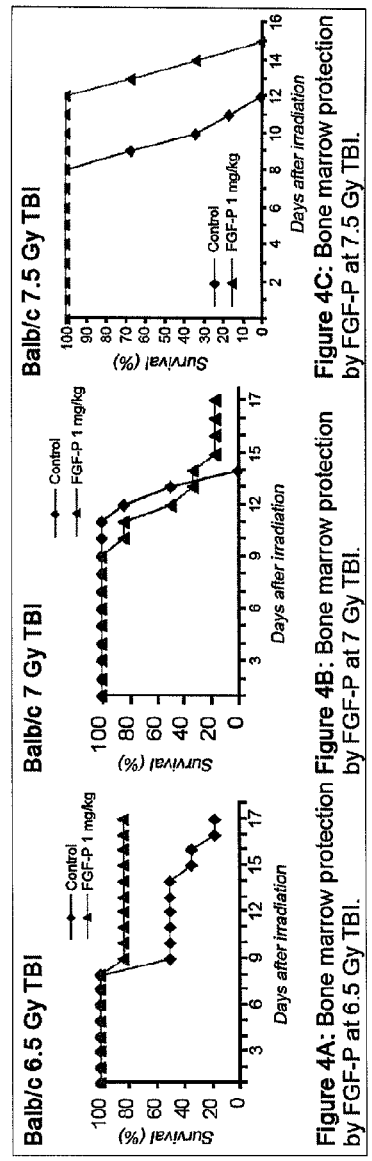
FIG. 4 shows that FGF-P was tested in TBI experiments with a 30 day time line. Importantly, it was shown that FGFs can increase the LD50/30 and improve bone marrow repopulation. To test whether FGF-P shared this property with other FGFs, the TBI model in Balb/c mouse was used. When mice were given 6.5 Gy, all control mice died within 12 days, while 87% of mice treated with FGF-P survived (FIG. 4A,B). When the TBI dose was raised to 7.5 Gy, again all control mice died within 12 days, while 66% of mice treated with FGF-P survived (FIG. 4C). The difference between vehicle alone and FGF-P treatment groups were statistically significant ($P<0.05$).

While a ground level nuclear detonation or fallout exposure will produce an inhomogeneous dose distribution which in many victims will spare a portion of the bone marrow, an above ground detonation in the first few miles (depending on the blast tonnage) would produce a total body exposure. Therefore, FGF-P was tested in TBI experiments with a 30 day time line. Importantly, it was shown that FGFs can increase the LD50/30 and improve bone marrow repopulation (12-16). To test whether FGF-P shared this property with other FGFs, the TBI model in Balb/c mouse was used. When mice were given 6.5 Gy, all control mice died within 12 days, while 87% of mice treated with FGF-P survived (FIG. 4A,B). When the TBI dose was raised to 7.5 Gy, again all control mice died within 12 days, while 66% of mice treated with FGF-P survived (FIG. 4C). The difference between vehicle alone and FGF-P treatment groups were statistically significant (P<0.05).

Direct Effect of FGF-P on the GI Tract

Enhanced proliferation of crypts in small intestine: The epithelium of the small intestine has a rapid turnover, renewing every 3-7 days. The stem cells are located ⅓ of the way up the villus and active mitosis can be seen above growing into the villus and below, forming the crypt. There are no definitive markers available to identify the stem cells, and thus the number of these cells in each crypt are unknown. When the bowel is irradiated, the number of crypts remains constant up to a dose just below the LD50/7. Above that dose, there is a log-linear decrease in the number of crypts, usually measured at 3.5 days. This phenomenon has been modeled mathematically using the multi-target model: $S/So=(1-(1-\exp(-d/Do)^N)$. Here S/So is the surviving fraction of crypts, Do is related to the intrinsic sensitivity of the crypt stem cells, and N is an integer related to the initial number of stem cells per crypt. An increase in N therefore suggests a proliferation of stem cells; an increase in Do represents an increased resistance of stem cells to apoptosis, differentiation, and reproductive inactivation. It has been shown that FGFs can both increase the number and resistance of stem cells in the crypt, with different effects in different animal models. Data from the crypt assay can be augmented with injection of BrdU. BrdU can be given to animals at one or more times after irradiation to determine the rate of proliferation and rate of elongation of villi.

Figure 5:
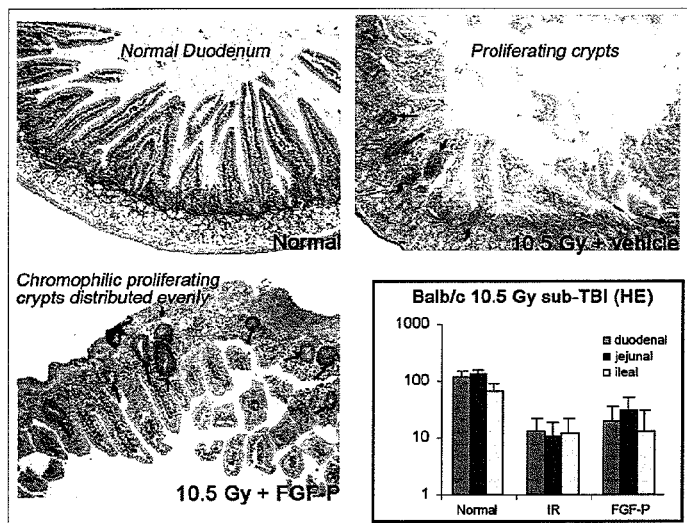
FIG. 5 shows enhanced proliferation of crypts in small intestine: compared with the normal untreated bowel, the numbers of proliferating crypts in all the segments of bowel exposed to 10.5 Gy treated with vehicle alone were decreased dramatically (control crypt numbers were 110-130 vs. 10-15 after 10.5 Gy). However, when treated with FGF-P, the numbers of proliferating crypts in the bowel (FIG. 5A) were increased. There was an associated decreased BrdU staining of remaining crypts (FIG. 5B, $P<0.05$). The results indicate that FGF-P, like FGF-1 and FGF-2, approximately doubles crypt survival which is consistent with improved stem cell survival and/or proliferation.
Figure 5:
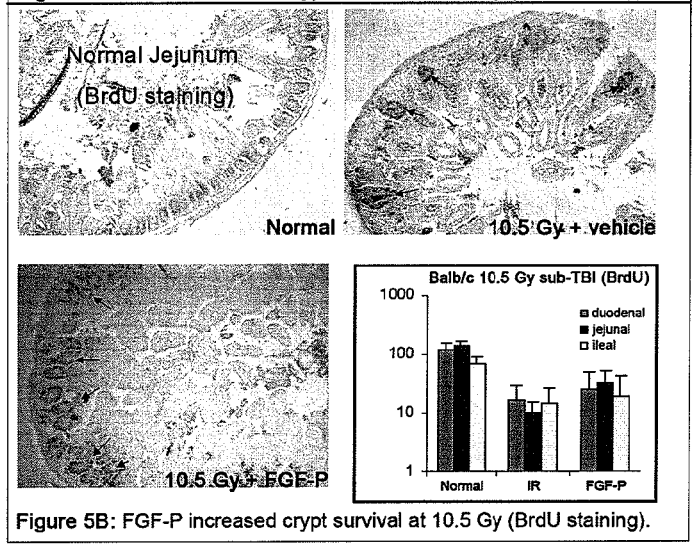

Initial studies are shown below. Briefly, mice exposed to 10.5 Gy sub-TBI were randomly divided into two groups and saline or FGF-P (2 mg/kg) was then given im. This dose of FGF-P was chosen based on Dr. Peña's experience with a related peptide (20-22). FGF-P was then repeated daily for 2 days. At 80 hr post-IR, BrdU (120 mg/kg) was injected ip and 4 hours later (about 3.5 days post-IR), the mice were sacrificed and the duodenal, jejunal and ileal segments (3-4 pieces/segment) were harvested, fixed in formalin, processed in paraffin blocks, cut in transverse sections of the full segment circumference (5 μm thick) and stained with H&E or anti-BrdU following the standard immunochemistry procedure (23). The proliferating crypts were defined as containing 10 or more adjacent chromophilic non-Paneth cells and a lumen. The circumference of a transverse cross-section of the intestine was used as a unit. The number of proliferating crypts was counted in each circumference. At least 10 circumferences were scored per mouse and 4-5 mice were used to generate each data point. The results (FIG. 5) showed that compared with the normal untreated bowel, the numbers of proliferating crypts in all the segments of bowel exposed to 10.5 Gy treated with vehicle alone were decreased dramatically (control crypt numbers were 110-130 vs. 10-15 after 10.5 Gy). However, when treated with FGF-P, the numbers of proliferating crypts in the bowel (FIG. 5A) were increased. There was an associated decreased BrdU staining of remaining crypts (FIG. 5B, P<0.05).

Figure 6:
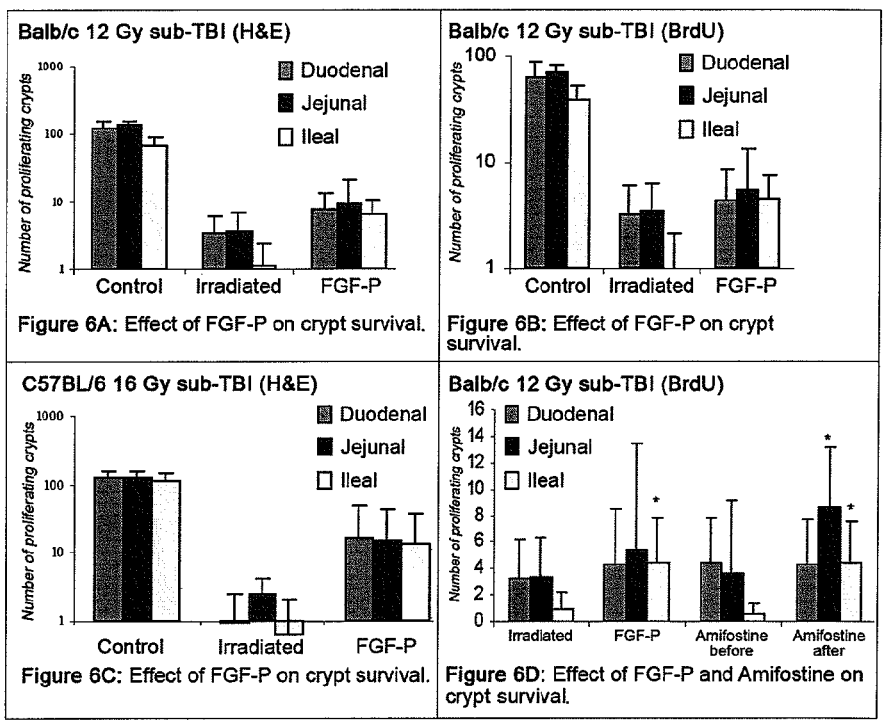
FIG. 6 shows that when the IR dose was raised to 12 Gy, the proliferating crypts in mice treated with vehicle alone dropped significantly as compared to 10.5 Gy (a further three-fold decrease to 3-4 crypts per circumference), while there was again a higher number of proliferating crypts in duodenum, jejunum and ileum in FGF-P treated group (FIG. 6A, $P<0.05$). A similar result was obtained using the BrdU staining method (FIG. 6B, $P<0.05$) to that observed in the 10.5 Gy group. C57BL/6 mice are less sensitive to AGS than Balb/c, and are less responsive to native FGF-2. It was found that the same FGF-P dose (FIG. 6C) there was improved crypt numbers in all sections of C57BL/6 small bowel at doses as high as 16 Gy sub-TBI.

The results indicate that FGF-P, like FGF-1 and FGF-2, approximately doubles crypt survival which is consistent with improved stem cell survival and/or proliferation. When the IR dose was raised to 12 Gy, the proliferating crypts in mice treated with vehicle alone dropped significantly as compared to 10.5 Gy (a further three-fold decrease to 3-4 crypts per circumference), while there was again a higher number of proliferating crypts in duodenum, jejunum and ileum in FGF-P treated group (FIG. 6A, P<0.05). A similar result was obtained using the BrdU staining method (FIG. 6B, P<0.05) to that observed in the 10.5 Gy group.

As previously mentioned, C57BL/6 mice are less sensitive to AGS than Balb/c, and are less responsive to native FGF-2. It was found that the same FGF-P dose (FIG. 6C) there was improved crypt numbers in all sections of C57BL/6 small bowel at doses as high as 16 Gy sub-TBI. This histopathological data was consistent with the 33% long-term survival data (over 2.5 months) of C57BL/6 mice after 16 Gy sub-TBI. The villi length of duodenum, jejunum and ileum was measured using a customized Imaging Pro program. The 16 Gy sub-TBI dose reduced villi length compared to normal mice, and treatment with FGF-P better preserved villi length in the duodenum and jejunum (P<0.05). Taken together, these data provide evidence that FGF-P reduces loss of differentiated cells of the bowel mucosa.

FIG. 6D shows crypt numbers counted 3.5 days after 12 Gy in the ileum of Balb/c mice. Radiation with saline im nearly eliminated the crypts. Higher numbers of crypts were observed with FGF-P given after irradiation. The level of protection matched that obtained for Amifostine (200 mg/kg iv 30 min before sub-TBI). However, Amifostine, unlike FGF-P, had no effect when given after irradiation.

FGF-P Partially Preserves and Restores the Physiological Function of the Gastrointestinal Tract There are commonly employed assays known to be relevant to both mouse and man for determining relative endpoints. These include: 1) stool blood: mucosal barrier breakdown is associated with bleeding of the small bowel; therefore, a hemoccult analysis with a commercial kit (BD Cat #64151) was used in the preliminary data at 3 days after sub-TBI. The time course and frequency of GI bleeding; 2) stool formation: the GI functions of digestion, absorption of nutrition and water, and the regular movement of intestinal muscle are required for formation of normal stool can be measured. All these functions can be upset by radiation. For example, loss of villi leads to decreased fluid absorption and diarrhea. The colon was excised and examined visually for the presence of formed stool at 3.5 days post-IR; 3) endotoximia: bacterial translocation can occur at early times following gastrointestinal radiation exposure.

Some studies have employed bacterial culture of liver samples. Bacterial translocation occurs due to mucosal barrier changes (1) at the level of the basement membrane and (2) bowel mucous volume and composition. The most reliable and most clinically applicable method to measure bacterial translocation is the endotoxin assay. The level of plasma endotoxin 3.5 days post-IR was measured with a commercialized kit that utilized tachypleus amebocyte lysate to sensitively quantitate endotoxin at extremely low levels (<0.01 EU/ml); and 4) body weight (BW): poor nutrition and water absorption will result in reduced body weight. The rate and severity of weight loss, as well as the pace of body weight recovery, will be measured. Experiments were performed for all the above studies and all support the utility of FGF-P as an AGS mitigator.

Figure 7:
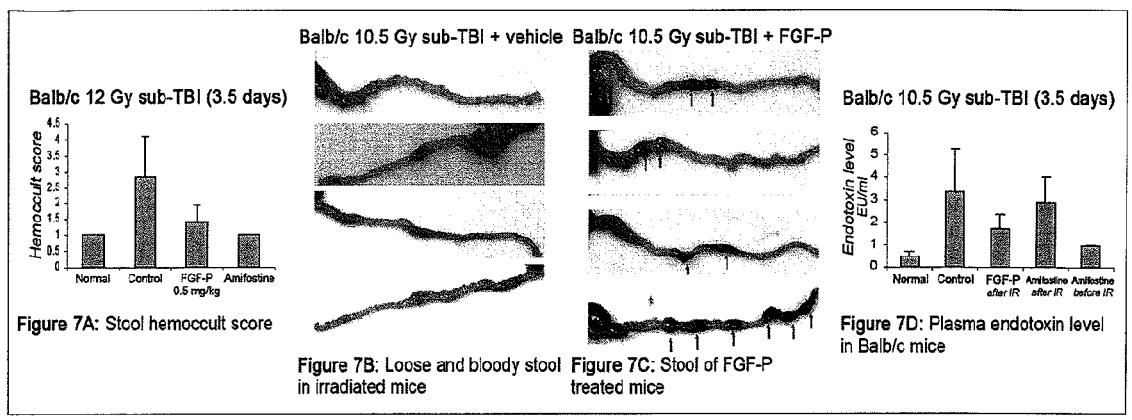
FIG. 7 shows that FGF-P partially preserves and restores the physiological function of the gastrointestinal tract. The results are summarized in the following: 1) The stool hemoccult score differed among the groups (FIG. 7A) in a pattern that correlated with the survival studies and crypt analyses. The irradiated Balb/c treated with FGF-P 15 min post irradiation (2 mg/kg im) or Amifostine (positive control given iv 30 min pre-irradiation) had a reduced stool hemoccult score following 12.5 Gy sub-TBI ($P<0.05$). Similar results were obtained in C57BL/6 mice. 2) A standard scoring scale was used to evaluate stool formation (diarrhea). The bowel was extracted from the abdomen and visually inspected. Formed stool was easily distinguished from semi-solid and liquid stool as it passed from the ascending to descending colon.
Figure 7:
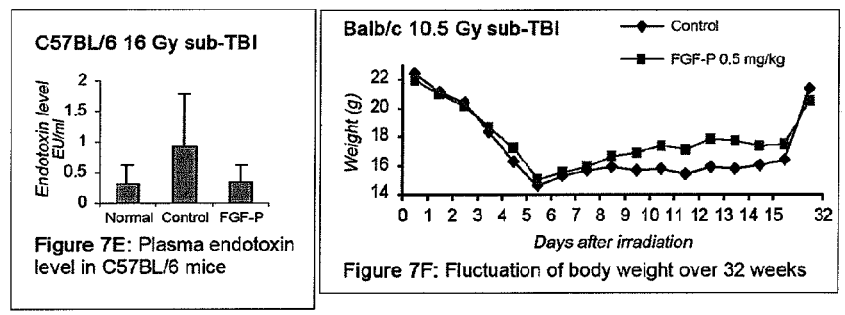

The results are summarized in the following: 1) The stool hemoccult score differed among the groups (FIG. 7A) in a pattern that correlated with the survival studies and crypt analyses. The irradiated Balb/c treated with FGF-P 15 min post irradiation (2 mg/kg im) or Amifostine (positive control given iv 30 min pre-irradiation) had a reduced stool hemoccult score following 12.5 Gy sub-TBI (P<0.05). Similar results were obtained in C57BL/6 mice. 2) A standard scoring scale was used to evaluate stool formation (diarrhea). The bowel was extracted from the abdomen and visually inspected. Formed stool was easily distinguished from semi-solid and liquid stool as it passed from the ascending to descending colon. FIGS. 7B and 7C show the irradiated bowel in controls compared with FGF-P-treated Balb/c mice. The FGF-P was given at a dose of 2 mg/kg im for three daily doses beginning 15 min after irradiation. Animals were sacrificed 3.5 days after 10.5 Gy sub-TBI. 3) The plasma endotoxin level of Balb/c mice that had been exposed to 10.5 Gy sub-TBI was elevated significantly in vehicle treated groups compared to normal mice (mean 0.45 vs. 3.32 EU/ml), while the irradiated mice treated with FGF-P had a reduced endotoxin (mean 2.12 EU/ml, FIG. 7D). Amifostine (as positive control, 24) that was delivered by iv injection 30 min before 10.5 Gy IR resulted in a reduction of endotoxemia (mean 0.93 EU/ml), but it had no effect when given after irradiation (2.87 EU/ml). Similar results were obtained in C57BL/6 mice that were exposed to up to 16 Gy sub-TBI (FIG. 7E). The consistent data from two strains of mouse confirms that FGF-P can reduce endotoxemia. These data show that FGF-P is capable of partially restoring GI function following radiation exposure, which accounts for the ability of FGF-P to rescue mice from ARS.

FGF-P Partially Restores GI Endocrine and Exocrine Function

The gastrointestinal tract facilitates nutritional absorption and digestion through endocrine organs and exocrine function. Measurements of these functions in Balb/c mice with AGS, with and without FGF-P treatment have been made. Regarding endocrine function, critical proteins produced by epithelial cells lining the small intestine and/or the pancreas are: 1) secretin, which stimulates secretion of a bicarbonate-rich fluid from the pancreas and liver; and 2) insulin, produced by pancreatic β cells, which controls the level of blood glucose. Regarding exocrine function, a major digestive protein, amylase was measured. Amylase is secreted by epithelial cells along the GI tract, including the pancreas.

Figure 8:
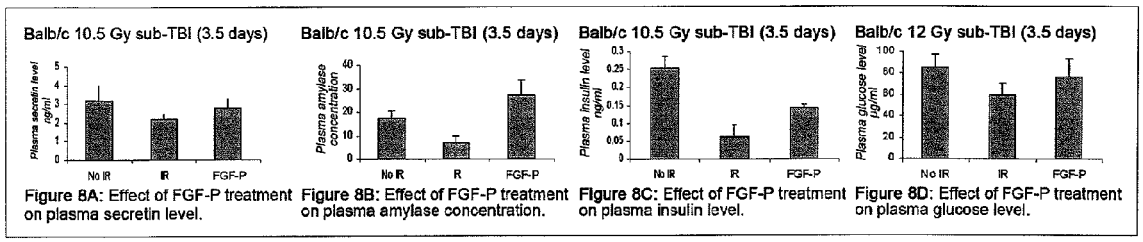
FIG. 8 shows FGF-P partially restores GI endocrine and exocrine function. The samples were collected 3.5 days after irradiation. It was found that: 1) compared with normal mice, the plasma level of secretin in irradiated mice was reduced, indicating loss of epithelial cells lining the small intestine. FGF-P reversed this effect, (FIG. 8A, $P<0.05$); 2) the plasma amylase level decreased 3.5 days after irradiation but FGF-P restored it to normal levels (FIG. 8B, $P<0.05$); 3) similarly, plasma insulin levels were restored to near normal after FGF-P treatment (FIG. 8C, $P<0.05$); and 4) along with all these other benefits nutritional status was better preserved as was blood glucose (FIG. 8D).

For secretin, the amino acid sequence in mice is (HSDGT-FTSELSRLQDSARLQRLLQGLV, SEQ ID NO: 4), which has a one amino acid change (M vs. T) at position 5. The kit for human secretin (Peninsula Laboratories, cat #S-1229) has been tested and it recognizes the mouse form. A mouse insulin kit is available (Linco Inc. Cat #EZRMI-13 K). The EnzChek Ultr Amylase Assay kit (Molecular Probes, Cat #E33651.3) can be used for all species, since it measures for the enzymatic product. Blood glucose level can be measured with a commercial kit from Sigma (Cat #GAG0-20 and GAHK-20) and is based on enzymatic activity, which is also universal to all species. Using these kits, the alterations in the plasma concentrations of the GI-derived proteins and peptides in mice that had been exposed to 10.5 Gy sub-TBI and, thereafter, received vehicle alone or FGF-P (2 mg/ml im) for 3 doses (10 min, 1 day, and 2 days post-IR) were measured. The samples were collected 3.5 days after irradiation. It was found that: 1) compared with normal mice, the plasma level of secretin in irradiated mice was reduced, indicating loss of epithelial cells lining the small intestine. FGF-P reversed this effect, (FIG. 8A, $P<0.05$); 2) the plasma amylase level decreased 3.5 days after irradiation but FGF-P restored it to normal levels (FIG. 8B, $P<0.05$); 3) similarly, plasma insulin levels were restored to near normal after FGF-P treatment (FIG. 8C, $P<0.05$); and 4) along with all these other benefits nutritional status was better preserved as was blood glucose (FIG. 8D).

Effect of FGF-P on Plasma Inflammatory Molecules after Exposure to High Dose Sub-TBI It has been that certain growth factors can additively improve the survival outcome in mice receiving optimal doses of FGF-2. Bead array technology has been developed to facilitate the study of cytokine expression profiles in normal tissues following radiation. Bead arrays have several advantages over ELISA. First, mice have a limited blood volume (0.3-0.4 ml of plasma/mouse). Each ELISA typically requires approximately 0.1 ml and thus only a limited number of assays are possible. Secondly, the time required to perform ELISAs one by one stresses the system in a large experiment and would be difficult to perform in the field in case of a radiological event. The Luminex bead array technology was used. The paired monoclonal antibodies, the highly-purified protein standards, and the more than 50 different cytokinespecific beads were purchased. In these studies, Balb/c mice received 12 Gy sub-TBI and then im injection of vehicle alone (0.2 ml of saline), FGF-P (2 mg/kg at 10 min post-IR and daily for two days), or Amifostine (200 mg/kg, either 30 min before IR, or 10 min after IR). The samples were collected 3.5 days after IR. Substantial changes can be seen for many of the cytokines that were measured.

Figure 9:
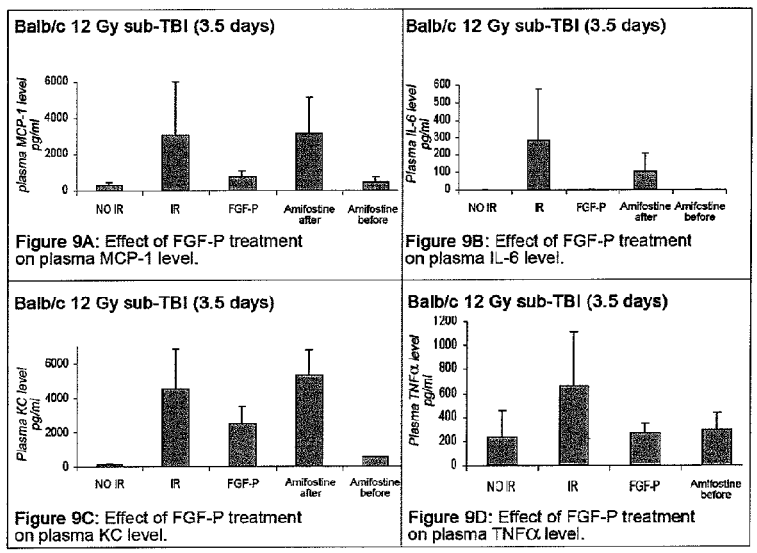
FIG. 9 shows the effect of FGF-P on plasma inflammatory molecules after exposure to high dose sub-TBI. MCP-1 (FIG. 9A), IL-6 (FIG. 9B), and TNFα (FIG. 9C) are shown. All three of these cytokines are associated with increased severity and progression of radiation-related inflammatory toxicity in mouse and man. The administration of FGF-P after irradiation normalized or near-normalized these factors while FGF-P and antioxidants like Amifostine work through different mechanisms and therefore are useful in combinations.
Figure 10:
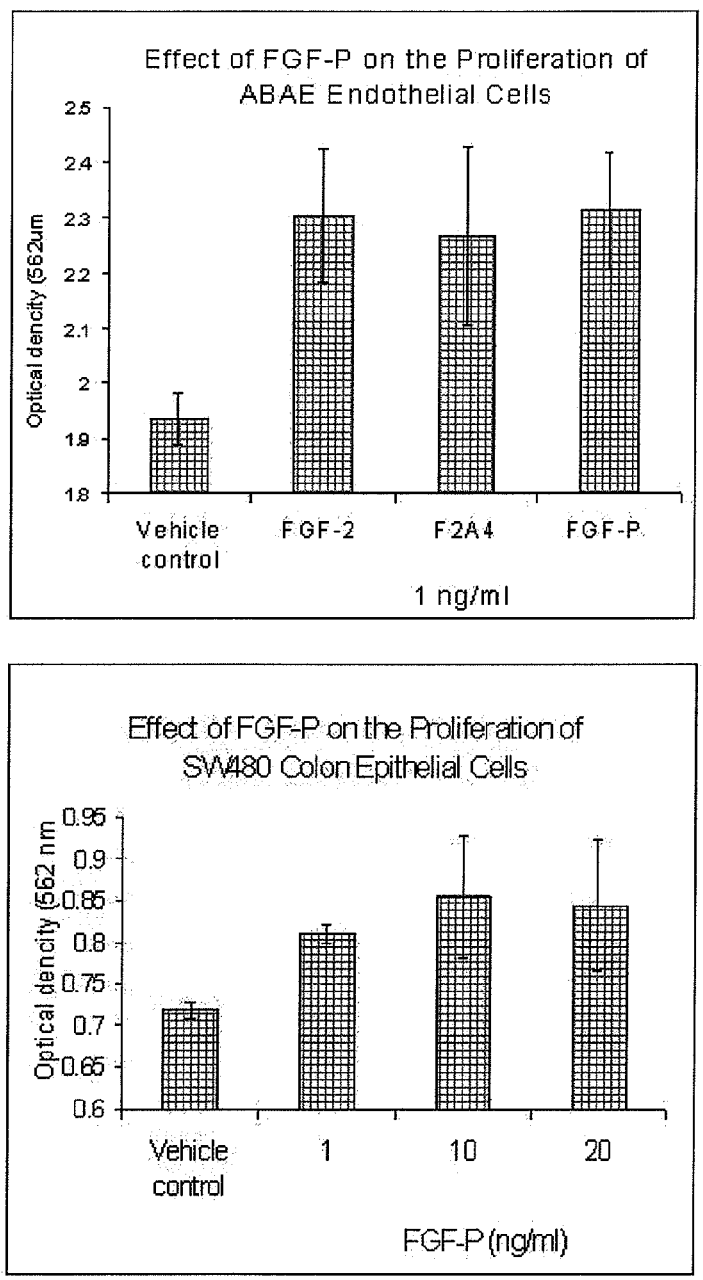
FIG. 10 shows the effect of FGF-P on the proliferation of epithelial and endothelial cells.

MCP-1 (FIG. 9A), IL-6 (FIG. 9B), and TNFα (FIG. 9C) are shown. All three of these cytokines are associated with increased severity and progression of radiation-related inflammatory toxicity in mouse and man. The administration of FGF-P after irradiation normalized or near-normalized these factors while Amifostine, given after irradiation, had no benefit. However, Amifostine, administered before radiation as a positive control, did provide a beneficial response. Indeed, FGF-P and antioxidants like Amifostine work through different mechanisms and therefore are useful in combinations.

Toxicity of FGF-P

Standard LD50/14 experiments have been performed. Up to 400 mg/kg of FGF-P was injected into Balb/c mice. No obvious signs of illness were observed. The mice were fully active and their body weight did not decrease. Thus, even the maximum NOAEL (no observed adverse effect level) could not be found. Given this result, the therapeutic index (TI=LD50/ED50) of FGF-P is likely to be >200, showing that it can be used with little concern for toxicity. This observation is not surprising since similar observations have been made previously with human FGF-2 in mice (9-14) Likewise, it has been shown that in various disease states the level of FGF in humans is commonly 100 times the normal baseline. In those disease states, FGF is elevated as a beneficial response to the disease.

Summary

It has been demonstrated that: 1) FGFs are among the few options we have for mitigation of AGS, and that FGF-P has several advantages (e.g., stability and stain independance) over native FGFs, 2) FGFs work by a specific receptor-mediated mechanism and are additive in combined therapy with other cytokines; 3) the antioxidant radioprotectant amifostine has a different mechanism of action than FGF: good utility for many gastrointestinal functions when given pre-irradiation; and 4) that the mechanisms seen in animals are closely tied to those seen in man.

Experimentally, it has been shown that: 1) FGF-P increases the survival of animals at a given TBI or sub-TBI dose level; 2) FGF-P has benefit even for C57BL/6 mice, a strain that is resistant to benefit from human FGF-2; 3) FGF-P provides better preservation of crypt counts after TBI and sub-TBI; and 4) FGF-P forms complexes on the cell surface and these complexes are specific binding sites. These data show that FGF-P is a useful mitigation drug to reduce ARS and specifically AGS.

Design and Methods

Pharmacokinetics (PK) of FGF-P (Month 1-9):

It is well-known that the three strains of mouse (BALB/c, C57BL/6, C3H/HeN) have relevant differences in their response radiation exposure and to FGFs. Therefore, their PK of FGF-P is determined. Human FGF-2 in mice has benefit at doses of 1 μg/mouse, the benefit peaks at 2 to 12 μg/mouse iv or im, and the benefit is lost at 24 to 48 μg/mouse.

Substantial benefit is seen at 2 mg/kg im of FGF-P. Therefore the range of 0.2 mg/kg through 20 mg/kg FGF-P im, can be useful, with the maximum benefit between 1 and 5 mg/kg.

In humans the usual circulating level of FGF-2 is in the range of 1 to 20 ng/ml. FGF-2 is normally seen in a pulsatile rather than a constant circulating level. The shape of the FGF-P plasma distribution over time is therefore important, and is measured to determine necessary dose scheduling. 3H FGF-P is after specific labeling of leucine. The plasma and major vital tissues, especially the gut and BM, are collected at different time points after different single doses of FGF-P and homogenized. The Cmax, tmax, t½, AUCt, AUC∞, CL/F, and Vss are calculated. Whole body cross-section mounts are also planed for autoradiography. Initially animals are pre-irradiated.

Methods:

1) Preparation of FGF-P: To ensure consistency for the course of the experiments, 1 to 2 grams of FGF-P (HPLC>95% pure) are used. There are many commercial companies that can perform this process.

2) Preparation of animal: Three strains of mice (BALB/c, C57BL/6, C3H/HeN, 8-12 weeks old) are obtained from NCI.

3) Preparation of 3H labeled FGF-P: The highly purified FGF-P (99% pure) is sent to GE healthcare group for 3H label.

4) Single and multidose dose PK in mice: Mixture of 3H-FGF-P and FGF-P (1, 2.5, 5, 10 mg/kg) are i.m. injected into control mice or 15 min to 1 day after sub-TBI. At different time points, the samples are collected (0, 0.25, 0.5, 1, 3, 6, 9, 24, and 48 hr for plasma and 0, 3, 6, 9, 24, 48 hr for gut and BM), and processed (homogenate of gut and BM) for the measurement of 3H-FGF-P level. The Cmax, tmax, t½, AUCt, AUC∞, CL/F, and Vss are calculated. The difference of PK pattern of different doses of FGF-P in plasma, gut and BM are determined. The correlation of plasma level with gut level of FGF-P are defined. For daily dose experiments, appropriate time points and plasma and tissue homogenate levels are measured each day for 3 to 5 days of the experiment.

5) MULTI-TOF Metabolism Studies: There are many specifically different components of FGF-P which produce a sharp and specific line on the spectrum. There are no natural FGF fragments that coincide with the FGF-P line. Thus there is no difficulty in performing studies aimed at measurement of the levels of FGF-P in tissues.

6) Statistical analysis: The mean and standard deviation for the each group is calculated and analyzed for statistical significance using student t test or ANOVA as appropriate. The pharmacological values are determined (Cmax, tmax, t½, AUCt, AUC∞, CL/F, and Vss). The analyses will compared between strains and before and after radiation to identify any significant differences. Additionally, Cmax and AUC data for FGF-P is compared with the results of efficacy (e.g LD50/7, crypt assay, hemoccult, body weight etc) and 12 molecular markers (e.g., GI endocrine and exocrine, endotoxin and inflammatory molecules) of AGS. A 20% dose modification factor or a 50% prolongation of median survival is evidence of benefit.

Optimal Dose and Schedule of FGF-P (Month 6-18):

The physiological factors that are measured include anatomic indices such as crypt number, number of BrdU positively staining crypts and the length of villi. Gastrointestinal functional indices are also measured including stool formation, hemoccult and body weight. GI specific endocrine and exocrine molecular indices: secretin, cholecystokinin (CCK), PYY, amylase, insulin and glucose are also very relevant to preservation of gastrointestinal function. Among the most important predictors of a survival outcome in AGS is the reduction of bacterial translocation. Thus systemic indices endotoxin and plasma level of inflammatory molecules are very relevant.

FGF-P, like FGF, can promote rapid repopulation of the bone marrow after irradiation thereby reducing the impact of bacterial translocation. Pathologic slides of the marrow therefore are evaluated along with the gastrointestinal tract. Using above objective and quantitative measurements, the efficacy of different doses and schedules of FG-P in treatment of different strains of mice with different radiation dose exposures is evaluated.

Methods:

1) Determine the optimal dose of FGF-P in different strains of irradiated mice: The mice (20/group) received different dose (9-16 Gy) sub-TBI are i.m. given FGF-P at different doses 10 min after IR. The number of survivors is monitored daily. The mice receiving 0 mg/kg FGF-P (control vehicle group) normally die within 7 days, while the FGF-P treated group either live longer (postpone of death) or rescue from death (no death). The dose that gives the highest survival rate among all different dose groups is defined as the optimal dose.

Test FGF-P Efficacy Along with PK Optimization

Efficacy Testing

LD50/7 (main index for efficacy) body weight, stool Form, hemoccult (functional response); Crypt assay (anatomy and pathological response); Endotoximia, Plasma level of Inflammatory molecules (surrogate markers).

The optimal FGF-P dose is given via i.m. to mice who received sub-TBI for 1, 2, 3, 4 or 5 doses daily. The results (death rate) are compared among the groups received different dosing. The schedule that gives the highest survival rate among all different schedule groups is defined as the optimal schedule.

The effective treatment relates with its starting time. To determine the starting time for effective treatment, the irradiated mice receive i.m. injection of optimal dose of FGF-P at different times (10 min, 1, 4, 8, 24 hr) after IR with an optimal schedule. The starting treatment time that gives a highest survival rate is defined as a best intervention time.

Determine the DMF in three strains of mice: After determination of the optimal dose, schedule and starting time of given FGF-P, three stains of mice are sub-TBI with a whole range of IR dose (10-16 Gy, the lowest dose will cause no deaths and the highest dose 100% deaths in order to be sure the LD50/7 is within the range) and then given the optimal dose with optimal schedule at best starting time after IR. The DMF is calculated to determine the best effect of FGF-P on the lethal GI syndrome.

Crypt Assay: Mice are subjected to sub-TBI or TBI. Doses range from the highest dose that causes no crypt loss to a dose that leave less than 10 crypts per circumference. The analysis determines both the shoulder and slope of the dose response curve as an estimate of the preservation and proliferation of stem cells in the crypt and intrinsic resistance of the stem cells respectively. On day 3, mice are i.p. injected with 120 mg/kg BrdU and 4 hour later (about 3.5 days after IR), the mice are sacrificed and the duodenum, jejunum and ileum (3-4 specimens/segment) is fixed in formalin, processed in paraffin blocks, cut in transverse sections of the full segment circumference (5 μm thick) and stained with H&E or anti-BrdU following the standard immunochemistry procedure with antigen retrieve (1).

The proliferating crypts are defined as containing 10 or more adjacent chromophilic non-Paneth cells and a lumen. The number of proliferating crypts are counted in each circumference. At least 10 circumferences are scored per mouse and 5 mice are used to generate each data point. The different segments of bowel can have slightly different measurements but also provide a reproducibility standard. The villi length of each circumference is measured using Imaging Pro program.

Body weight, Stool formation and Bleeding: Mice are exposed to radiation doses above the LD50/7. Five to 10 animals in each group. Control animals receive vehicle alone. Treated animals have different doses of FGF-P in different schedules. The time to a positive hemoccult study (BD Hemoccult) and the severity of the bleeding over time are recorded. Animals are weighted daily. The stool is observed daily and scored for the degree watery diarrhea using a standardized scale. The colon is removed. This is done in animals prepared for crypt assay. Colons are photographed and scored for stool formation again using a standardized semi-quantitative scale.

Endocrine and exocrine: the alterations of plasma secretin, cholecystokinin (CCK), amylase and insulin can be easily determined by ELISA. These studies are done in parallel with the body weight and crypt assays, and thus require fewer additional animals. These studies are done when the near-optimal FGF-P regimen is determined to round out the data collection for these selected FGF-P doses and schedules.

Surrogate systemic indices of AGS: Plasma endotoxin increases after TBI and sub-TBI. As in those experiments endotoxin is measured with the tachypleus amebocyte lysate kit.

Radiation causes the production of deleterious cytokines and such cytokines are also produced in response to localized gut damage and systemic infection. It has been shown that these factors are more normal in animals treated with FGF-P. Thus full bead arrays re employed.

9) Statistics analysis: The mean and standard deviation from each group is calculated and analyzed for statistical significance using student t test or ANOVA. Based on the previously measured coefficients of variance between control and irradiated animals, and assuming a 50% improvement using FGF-P, the group sizes of 5 to 10 animals are sufficient to detect those differences for most assays. Replicate experiments are conducted, raising the total number of animals to 20. This provides a power of near 80% of detecting a difference even for the most challenging assays.

Relative Inter-Species Binding and Activation of FGF Receptors (Month 1-15):

The FGF receptors require a very specific dimeric structure to activate the kinase. In order to scale dose and interpret the previously measured PK and efficacy data therefore it is useful to know the comparative ability of FGF-P compared to human FGF-2 for activating receptors in mouse and man. Bound dimeric biotin labeled FGF-P can be displaced using unlabeled FGF-P. This competitive dissociation follows Scatchard analysis wherein the biotin-FGF-P sites decreases in proportion to increasing KFGF-2/[FGF-2] or KFGF-P/[FGF-P]. To calculate the ratio of the dissociation constants (KFGF-2/KFGF-P) the slopes of the competitive binding curves is calculated (40-43).

This calculation can be done for human and mouse cell lines to measure any differences for trans-species scaling. The competitive binding assay is performed, using the Amnis imaging cytometer as using two pairs of cell lines. Endothelial cells of human and mouse origin are employed, since these cells are judged by many to be the main target of FGF-2. Small bowel epithelial cells are used to be sure that there are no unexpected differences in their receptor binding kinetics. Fibroblasts are also used to measure MAP kinase activation (ERKs, Ras/MAPK and PI-3 kinase/Akt signaling pathways and the cell proliferation (27-32)).

Method: 1) Preparation of cells: The YAMC mouse gut epithelial cells (35), HEV mouse mucosal high endothelium (33,34), SK-HEP-1 human liver endothelium (36) and Caco-2 transformed human intestinal epithelium (37,38) are used. These cell lines are commonly used to study properties of the gastrointestinal system (33-38). The cells are cultured in 3% FBS-IMEM until 80% confluence and then changed to serum free media 24 hours before use. In this way the impact of any growth factors in the FGS are minimized.

2) Binding of FGFRs to FGF-P and FGF-2 on the cell surface: The four types of cells are incubated with biotin-FGF-P (1 μg/ml) at a constant concentration, and controlled pH and temperature. Human FGF-2 at increasing concentrations (10-50 μg/ml) are then added as a competitor to displace the biotin-FGF-P. The detection probe is SA-FITC (4 μg/ml) followed by analysis with Amnis ImageStream. The FITC intensity represents the relative number of FGFRs on the cell surface and the imaging of binding pattern on each cell surface is recorded by customized image analysis. Foci per cell, on the cell surface, is tabulated and plotted against inverse FGF-2 concentration. The experiment is repeated this using FGF-P (without biotin) to displace the foci.

3) Comparison of affinity of FGF-P to FGFRs: Sub-confluent cells in 24 well plates are incubated with 3H-FGF-P (7.5 ng/ml, 1 mMol/mCi) with 1 mg/ml heparin (to block low affinity FGFRs). In some wells, the 100-fold excess cold FGF-P (to saturate non-specific binding) or 100, 50, 25, 12.5, 6.25, 3.12 ng/ml cold FGF-P is added for specific binding. After 4 hours at 4° C., the cells are washed 3 times and harvested with lysis buffer. The cells are then processed for counting the radioactivity with β-counter. Scatchard analysis is performed to determine the Kd in each type of cells (39). The Kd is compared between mouse and human cell types.

4) Comparison of phosphorylation of ERK, MAPK and Akt upon the stimulation of FGF-P: The cells are stimulated without (as control) or with various doses of FGF-P or human FGF-2 (0.5 1, 2.5, 5, 10 or 25 ng/ml) for 10 to 30 min and the cells are harvested with special lysis buffer (39). An equal amount of protein (30 μg/sample in 100 μl) is added to ELISA plates that quantitatively measure the phosphorylation of ERK, MAPK and Akt (R&D system kits) according to the manufacture's instruction. For the mouse and human cell lines the relative concentrations that ½ maximally activate the receptors are determined for FGF-2 and FGF-P.

5) Comparison of proliferation responsiveness to FGF-P: The FGF-P (0, 1, 2.5, 5, 10 ng/ml) is added to cells (70% confluence in serum free IMEM) in 96 well plates and incubated for 24-72 hours. A serial diluted known number of cells is used as a standard. MTT reagents are added to each well and the number of cells is determined from the standard curve.

6) Statistics analysis: The mean and standard deviation from each type of cells is calculated and analyzed for statistical significance using student t test or ANOVA as appropriate. Scatchard calculations are performed using standard algorithms (Instat or StatMate software).

Throughout this application, various publications are referenced. The disclosures of these publications in their entireties are hereby incorporated by reference into this application in order to more fully describe the state of the art to which this invention pertains.

It will be apparent to those skilled in the art that various modifications and variations can be made in the present invention without departing from the scope or spirit of the invention. Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

Example 2

Protective Effect of Native Full Length of FGFs on ARS

The disclosed methods and compositions relate to FGFs and their receptors for their potential use against ARS.

Interest in FGF2 as an agent to mitigate ARS was triggered by clinical observations of FGF2 plasma levels in patients before, during and after TBI at 1.7 Gy BID for 4 days administered in preparation for BM allgraft transplantation. A substantial continuous decline in circulating FGF2 levels was found (Okunieff 1999, Ding 1997). A similar pattern was found in the mouse TBI model using cytokine array analysis. The loss of FGF2 post-IR in both humans and the mouse model indicated that supplementation with exogenous FGF2 was a beneficial for ARS.

Synthesis and Design Considerations of Functional Peptide of FGF2 (FGF-P)

FGF2 has domains that bind to FGF receptors (FGFRs) and heparin (Langley 1997, Gu 2004, Fuks 1995). There are 4 main FGFRs and multiple splice variants, especially in exon III (corresponding to the FGFR protein domain D3), and these add to the complexity. Many cell and animal systems confirm a modal biological response wherein increases of FGF lead to a peak and then a decline in response. In most cases, FGFR activation acts as a strong mitogen to stimulate cell proliferation and inhibit apoptosis (Okunieff 1999). Since FGFRs are expressed on the surface of many types of cells, FGF2 exerts a broad range of biological functions including stem cell proliferation, cell differentiation, angiogenesis, and tissue repair (Okunieff 1999, Fuks 1995, Taylor 2007).

In Vitro Characterization of FGF-P Effects

Three preliminary experiments were carried out using FGF-P in vitro to confirm its activity. First, the biotin conjugated FGF-P was used as a tool to examine cell surface binding. AsPC-1 pancreatic cancer epithelial cells are known to have high levels of FGFR and were used for this study. ASPC-1 cells were incubated with 1 µg/ml of biotin-FGF-P and then labeled with streptavidin-FITC. The cells were then analyzed using an imaging flow cytometer (Amnis Imagestream). This device can image each cell as it passes through the laser, and it can then sort cells according to both staining and morphological characteristics. FGF-P was bound to the cell surface and caused the aggregation of FGFR (cluster spots) consistent with the known FGF signaling mechanism FIG. 1A. These clusters were counted, allowing for measurement of relative binding coefficients. Second, to test the feasibility of binding coefficient measurement, competition experiments were performed. Free FGF-P (30 ug/ml) was added to cells for 20 min and then the biotin-FGF-P (1 µg/mL) was added. One hour later, streptavidin-FITC was added and analyzed by flow cytometry. The free FGF-P competed with biotin-FGF-P for cell surface binding (FIG. 1B), consistent with the specific binding. In a third test, a bioassay was performed. FGF-P was added to culture media of two types of cells: endothelial cells (adult bovine aorta endothelium) and epithelial cells (SW480, a cell line from colon). The result showed that FGF-P stimulated the growth of both endothelium (FIG. 1C) and epithelium (FIG. 1D).

In Vivo Mitigation Effect of FGF-P on ARS

To determine if the in vitro stimulatory function of FGF-P can be translated in vivo against ARS, it was used in Balb/c mice exposed to different IR doses (6.5, 7 and 7.5 Gy). FGF-P (1 mg/kg) was given IM right after TBI and daily thereafter for 5 days. The mice were closely observed, and the date of death was recorded. The data (FIG. 4) showed that FGF-P exerted a mitigation effect on ARS induced by high IR dose with a DMF similar to that of native FGF2.

Figure 11:
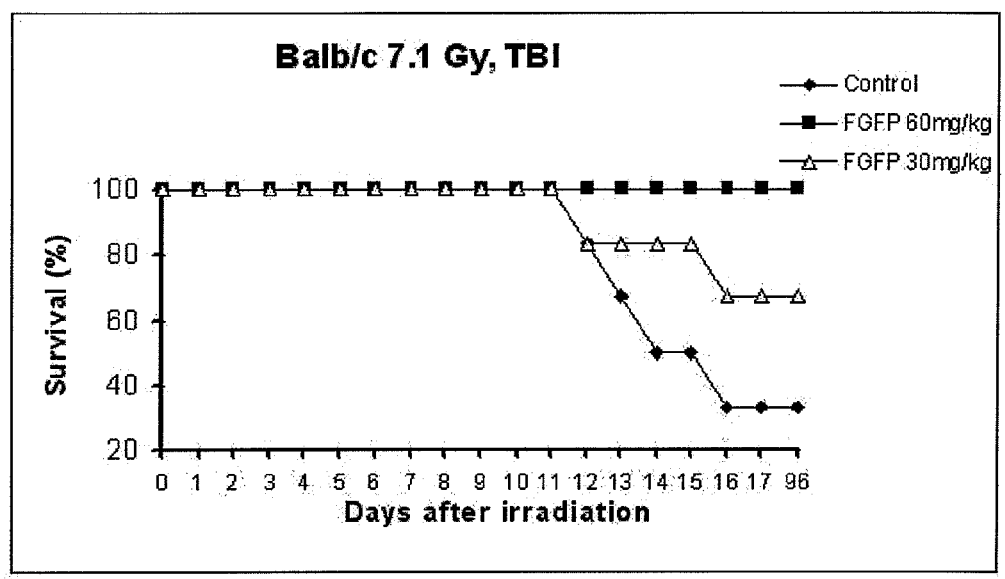
FIG. 11 shows the mitigation effect of FGF-P is dose-dependent.

To meet the criteria for "effective mitigation agent", an IR dose higher than 1.2× $LD_{50/30}$ (7.1 Gy) was used throughout testing of the dose and timing, since 7.1 Gy knocks down BM functions to almost "ground 0" and cause at least 80% death within 16 days. To see a better effect, the dose of FGF-P was increased to 15, 30, and 60 mg/kg. While 15 mg/kg was better than <10 mg/kg, the 60 mg/kg seemed to achieve a best result, and there was a dose-dependent effect (FIG. 11). Whether there is a plateau dose between 30-60 mg/kg remains to be determined.

Figure 12:
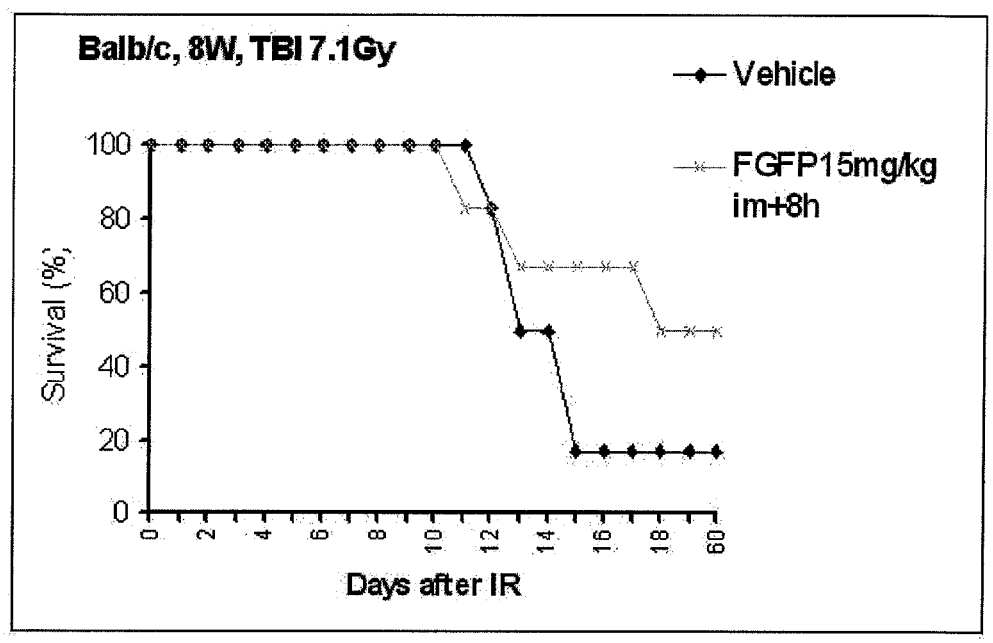
FIG. 12 shows that FGF-P is effective given at 8 hour after 7.1 Gy lethal TBI.

A useful mitigator can be effective even given 8-24 hours IR exposure because of the time required for distribution. Therefore, FGF-P given at 8 hour after 7.1 Gy IR was tested. The result was very promising as shown in FIG. 12. The 8 hr post-IR delivery was still effective, indicating that this agent meets the critical needs of anti-ARS. Importantly, the stability and toxicity tests indicated that: 1) boiled FGF-P was as effective as the original form; 2) mice tolerated up to 4 gram/kg well without any signs of sickness.

Figure 13:
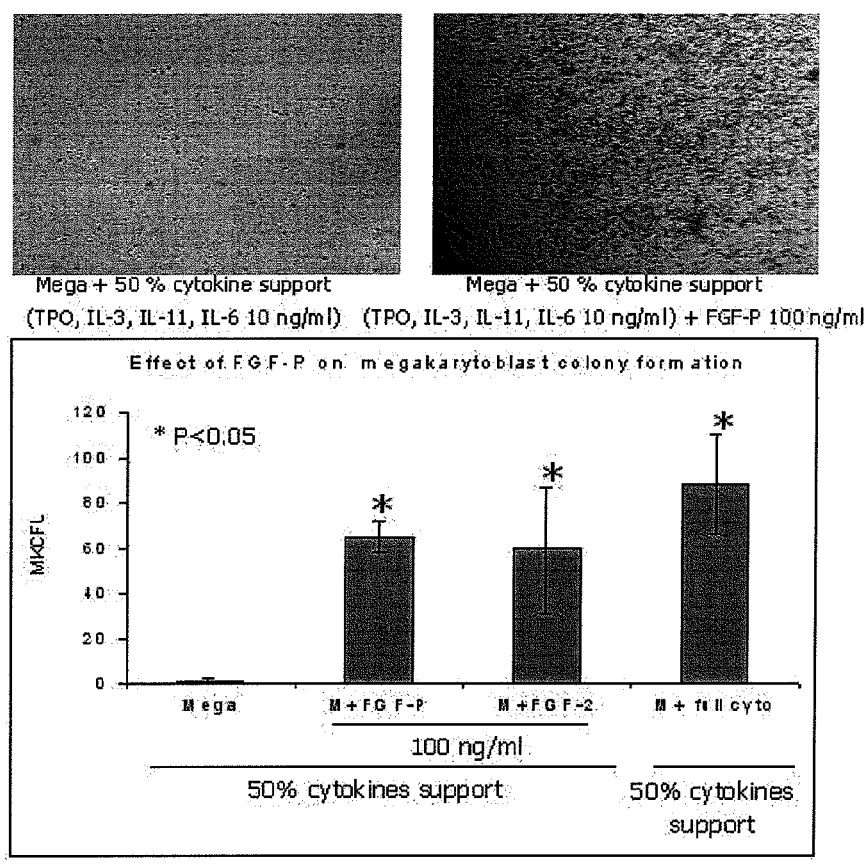
FIG. 13 shows the effect of FGF-P on megakaryoblast conly formation.
Figure 14:
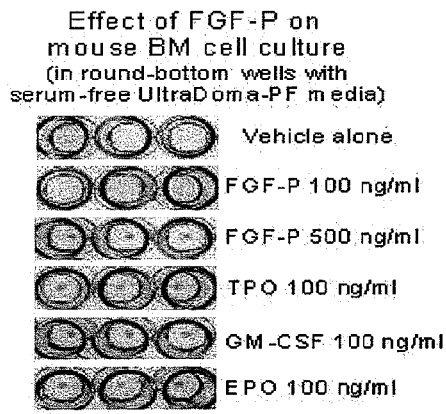
FIG. 14 shows that (A) BM cells grow in 96 wells. (B) FGF-P promotes BM cell regeneration. (C) FGF-P enhances BM colony formation (WBC, RBC).
Figure 14:
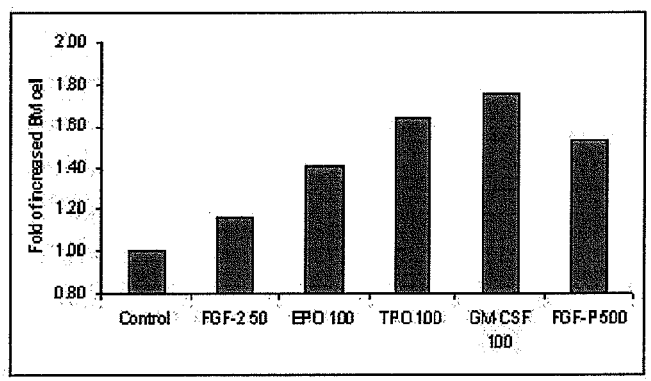
Figure 14:
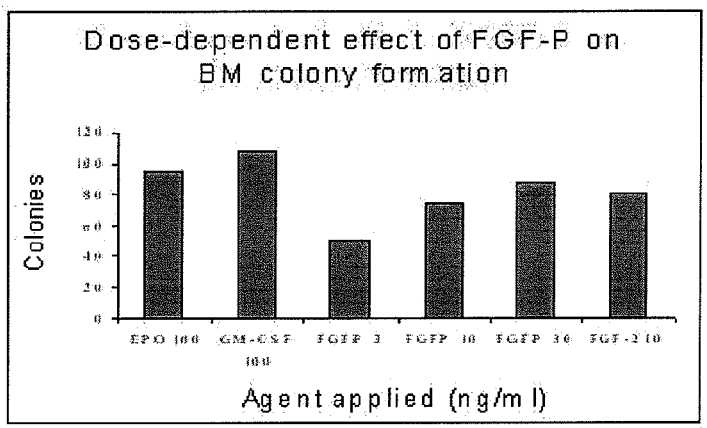

The Mitigation Effect of FGF-P is Related to Increased Regeneration of BM Stem Cells Survival of ARS depends on rapid reconstitution of hematopoiesis after IR-induced myelosuppression. The ability of FGF-P to prolong life of mice with ARS strongly indicates that the duration of myelosuppression is reduced. However, the timing and mechanism of effect on BM stem cells is unknown. Also unclear are the number of FGFRs on hematopoietic stem cells (HSCs) and their role in reconstitution after IR. The mesenchymal stem cells (MSCs) certainly possess high numbers of FGFRs, and it is known that hematopoiesis depends on local interactions between HSCs and MSCs (30). To characterize the effects of FGF-P on BM, the study approach was to obtain fresh BM (including both HSCs and MSCs) from Balb/c mice, and culture it under varying conditions (3 D culture or 2 D round-bottom well) in triplicate for 1-3 weeks. The BM cells were stimulated with FGF-P at different doses (as test) or with EPO, TPO, GM-CSF or native FGF2 (as a positive control). The cultures were examined using several methods including colony count, photography, CyQUANT® assay and $^3$H-TdR incorporation. The results indicated that: 1) the rich 100% cytokine cocktail media (from MegaCult-C of StemCell Tech Inc, Vancouver, Canada) were able to overwrite the effect of other stimulators. FGF-P stimulatory effect on megakaryocyte only exhibited when the cytokine cocktail was reduced to 50% (FIG. 13). The data demonstrated that while there was no megakaryocyte colony formed in the modified condition, the addition of 100 ng/ml FGF-P greatly stimulated the formation of megakaryocyte colony to the level as native FGF2 (FIG. 13); and 2) BM cells cultured in round-bottom 96 wells with serum-free ultraDoma-PF media (Lonza Ltd, Switzerland) were used to screen the effect of an agent much faster and cheaper than using colony formation assays (stemcell.com) because the round-bottom wells allowed cells to contact each other and made needed communication. The results demonstrated that: 1) In 96 well 2 D culture, FGF-P (500 ng/ml) stimulated the growth of BM cells in a similar pattern as TPO, EPO and GM-CSF (100 ng/ml) and the increased cells were seen clearly in wells (FIG. 14A); 2) FGF-P exerted a similar stimulatory effect on BM stem cells as EPO, TPO, GM-CSF and native FGF2, as evidenced by measurement of cell number in 2 D culture with the CyQUANT® assay kit (Mol Probe Inc, FIG. 14B); 3) FGF-P enhanced colony formation of BM cells in a dose dependent manner on MethoCult® 3 D culture, which is optimal for colony formation of multi-potential progenitors and lineage-restricted progenitors of the erythrocyte, granulocyte monocyte-macrophage lineages (FIG. 14C).

Figure 15:
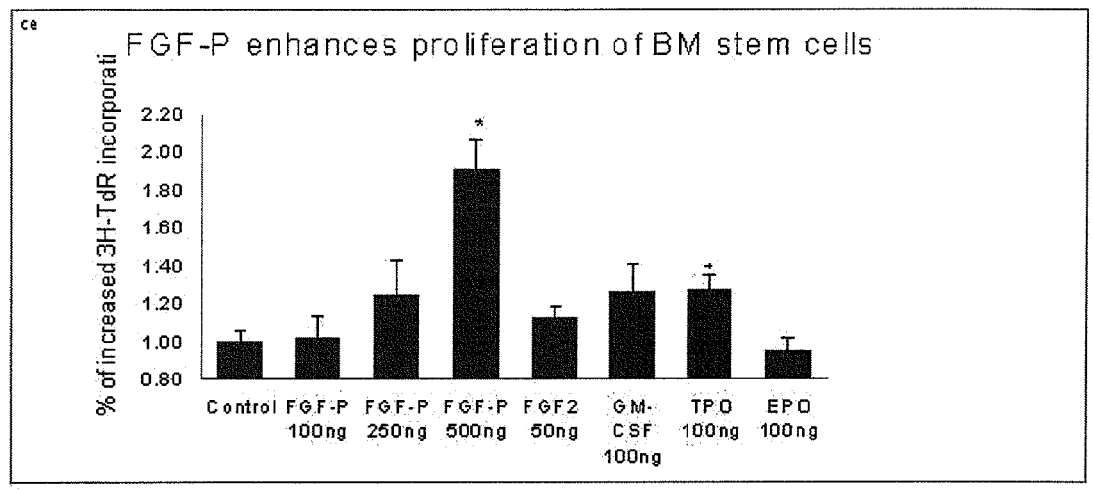
FIG. 15 shows (A) Normal BM cells response to FGF-P. (B) Irradiated (0.5Gy) BM cells response to FGF-P.
Figure 15:
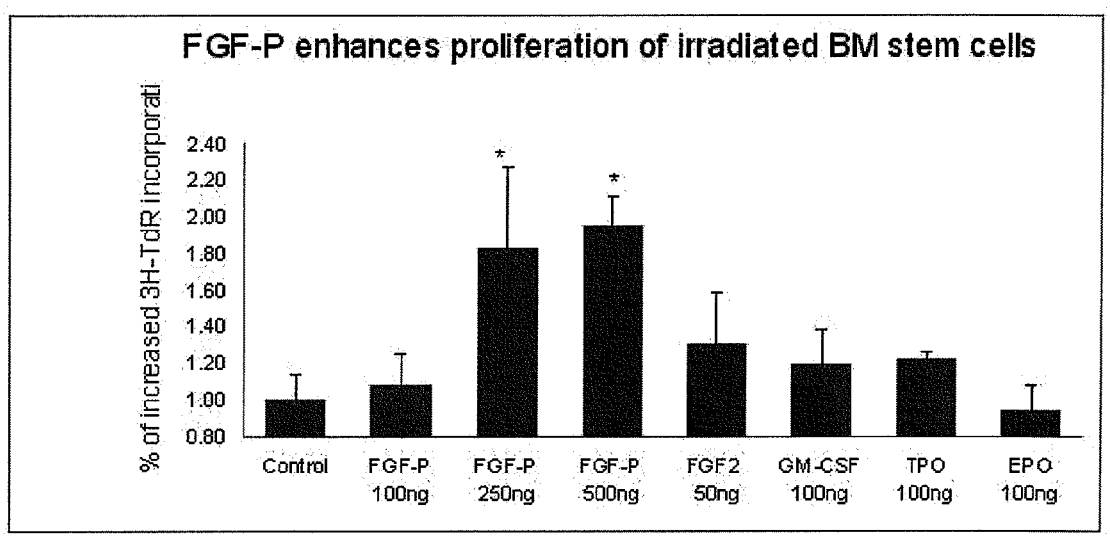

To determine if BM cells damaged by IR still responded to FGF-P, cells were plated in 96 round-bottom wells with serum-free ultraDoma-PF media and equally divided into two parts; one was not irradiated as control, and the other was irradiated with 0.5 Gy. They were then treated with equal amount of test agents within 1 hour post-IR. The following day, 0.2 uCi/well of $^3$H-TdR was added and they were further cultured for 4 days before harvesting with a 96 well automatic harvester. The results (FIG. 15, above) showed that: 1) the IR BM cells responded to FGF-P and other stem cell stimuli in the same fashion as normal BM cells. This finding, combined with the observation that FGF-P rescued mice after exposure to high dose IR, indicates that FGFRs in BM play an important role in hematopoiesis; 2) In both conditions, the FGF-P stimulatory effect was dose-dependent, although the doses was relatively high. It is of interest to find the reason for this high dose dependency; and 3) in these culture conditions, the order of responsiveness was FGF-P (250-500 ng/ml)>native FGF2 (50 ng/ml), GM-CSF and TPO (100 ng/ml). There was no response to EPO.

Figure 16:
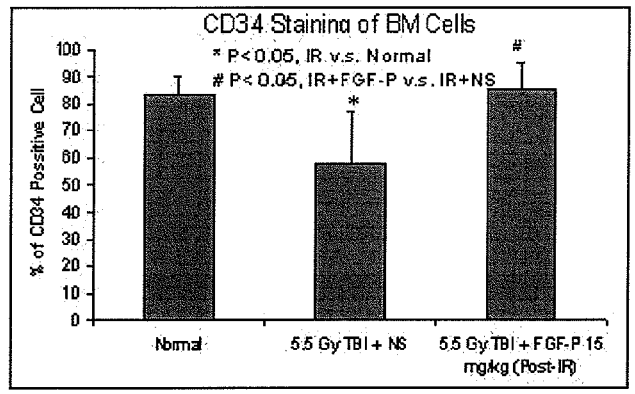
FIG. 16 shows (A) CD 34 staining of BM cells. (B) CD 24 staining of BM cells. (C) Both CD24 and CD 34 positive BM cells.
Figure 16:
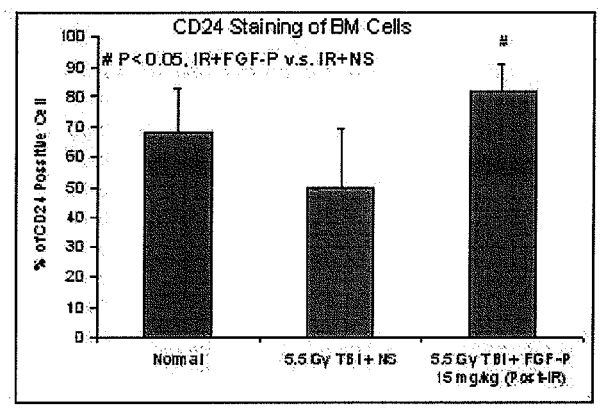
Figure 16:
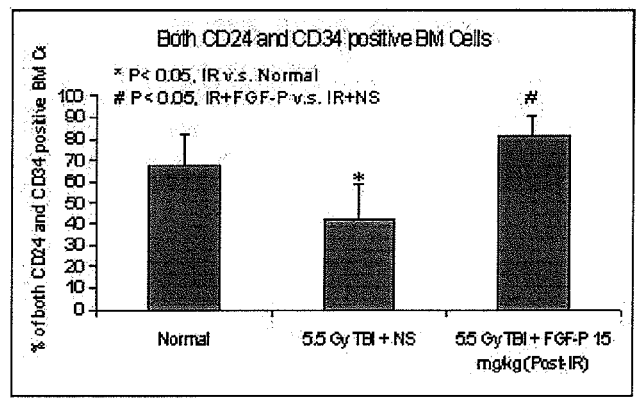

To determine if the stem cells are better regenerated, freshly harvested BM cells were stained with CD24, CD34 (two critical markers for BM multi-potential progenitors) and TER119 (a marker for reticulcoytes), and then analyzed with flow cytometry. The results demonstrated that the in vivo administration of FGF-P increased the number of BM progenitors following radiation (FIG. 16). This is consistent with the above in vitro data. After IR, there appears a very active generation of BM progenitors, a rebound phenomenon, similar to the intestine crypts that actively regenerate following IR to compensate for lost villi.

Both in vivo and in vitro data strongly indicate that FGF-P enhances hematopoiesis after IR, and this likely explains in part the mitigating effect of FGF-P.

IR Mitigation Effect of FGF-P is Related to Enhanced Recovery of Megakaryocytopoiesis and Improved Hemostasis.

Since bleeding and infection are the two major causes of ARS death, several experiments were performed in order to determine if the effect of FGF-P in rescuing IR mice was through enhanced recovery of megakaryocytopoiesis and improved hemostasis. Considerable practice and expertise are needed to obtain appropriately anti-coagulated blood from the inferior vena cava without platelet clumping or activation.

1. FGF-P Increases Platelet and Leukocyte Counts Post-IR

Figure 17:
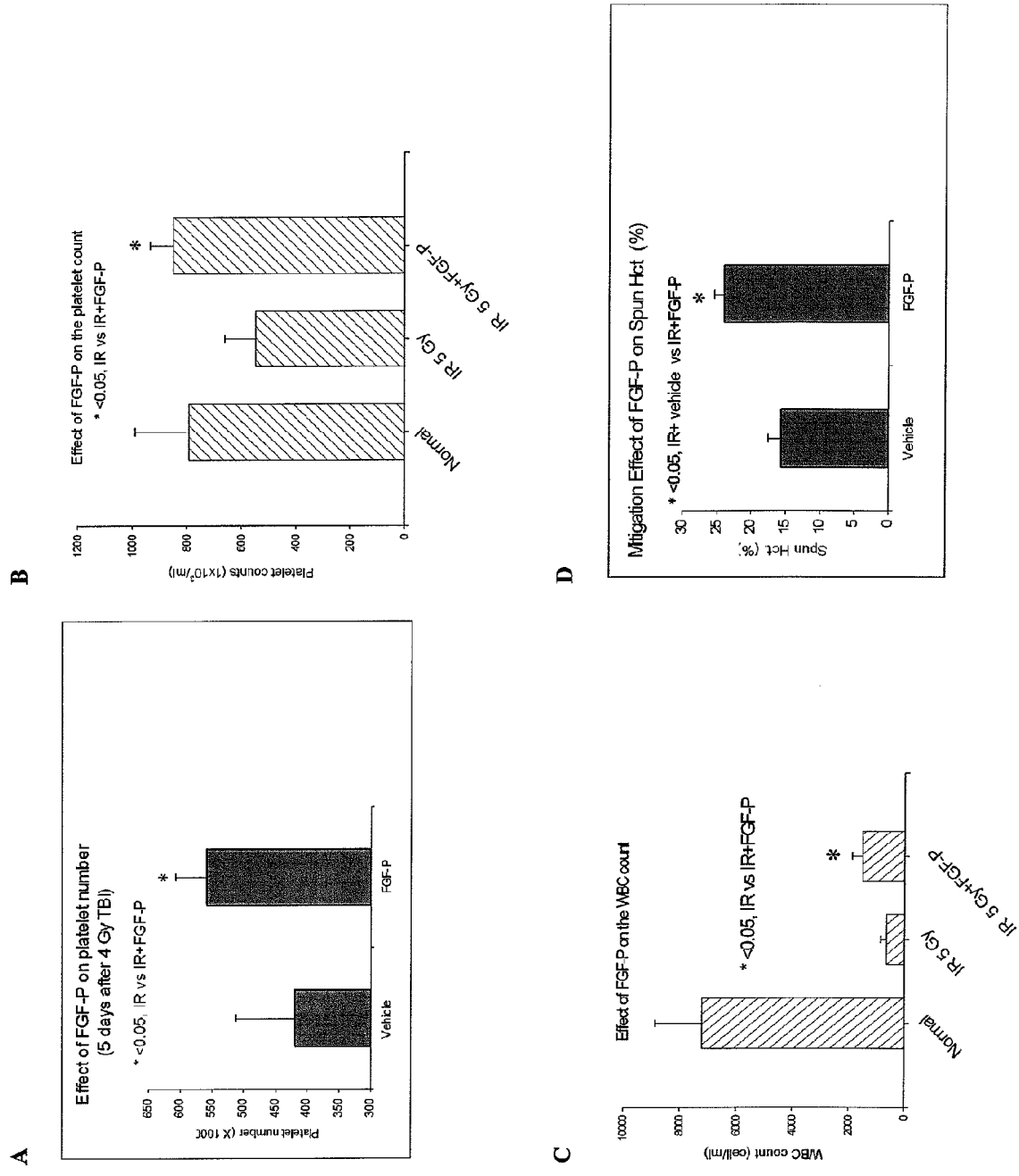
FIG. 17 shows (A) Increased platelet number (4 Gy). (B) Increased platelet number (5 Gy). (C) Increased WBC number (5 Gy). (D) Increased Spun Hct (5 Gy).

Following IR with 4 or 5 Gy TBI, blood was obtained from the inferior vena cava and platelets enumerated by phase contrast microscopy with a hemacytometer. The results indicated that mice treated with FGF-P had accelerated recovery of platelet counts (FIGS. 17A and B). In parallel, the leucocytes and red cells were increased as compared to vehicle-treated mice that received the same IR dose (FIGS. 17C and D).

Figure 18A:
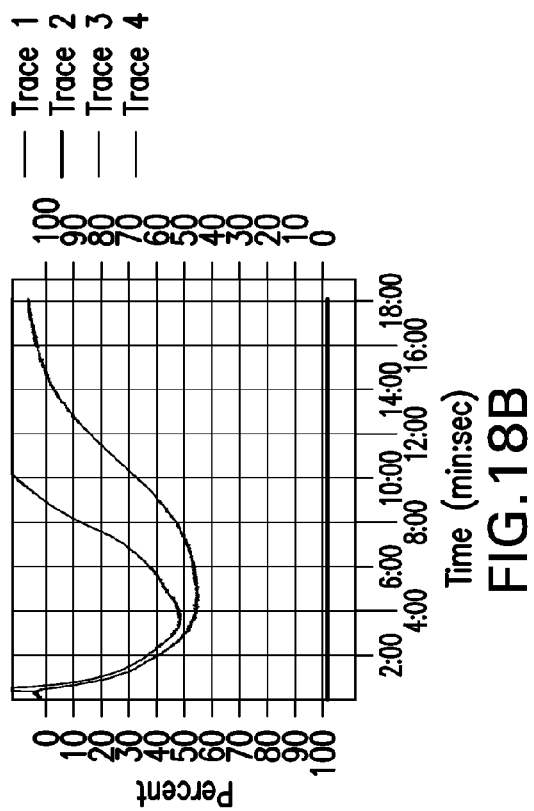
FIG. 18 shows (A) Platelet aggregation (normal). (B) 4Gy TBI (29 days post-IR). (C) 4Gy TBI+FGF-P (29 days post-IR). (D) FGF-P promotes recovery of aggregation.
Figure 18B:
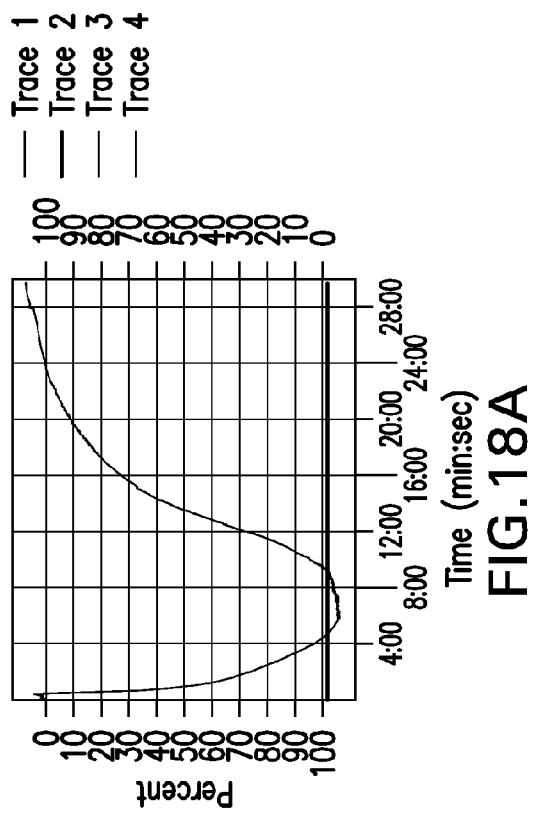
Figure 18C:
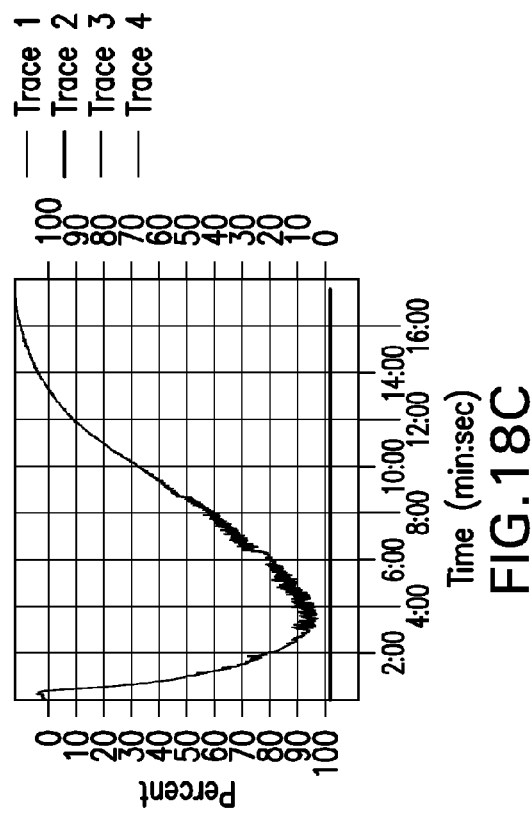
Figure 18D:
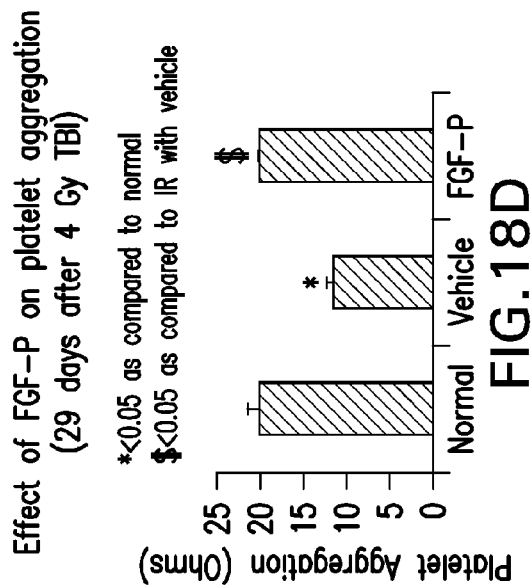

2. FGF-P Enhances Function of Platelet:

One of the major functions of platelet is to aggregate on the wounded site as first step to block the bleeding vessel. The results show that the on day 29 after 4 Gy TBI, the platelet aggregation in mice treated with FGF-P (FIG. 18C) right post-IR daily for 6 day was recovered towards normal (FIG. 18A) while the control mice had a great lost of aggregation capability (FIG. 18B), which indicates that FGF-P promotes the recovery of the number of platelet lost due to IR and its biological function. This recovery is statistically different (FIG. 18D $P<0.05$).

Figure 19:
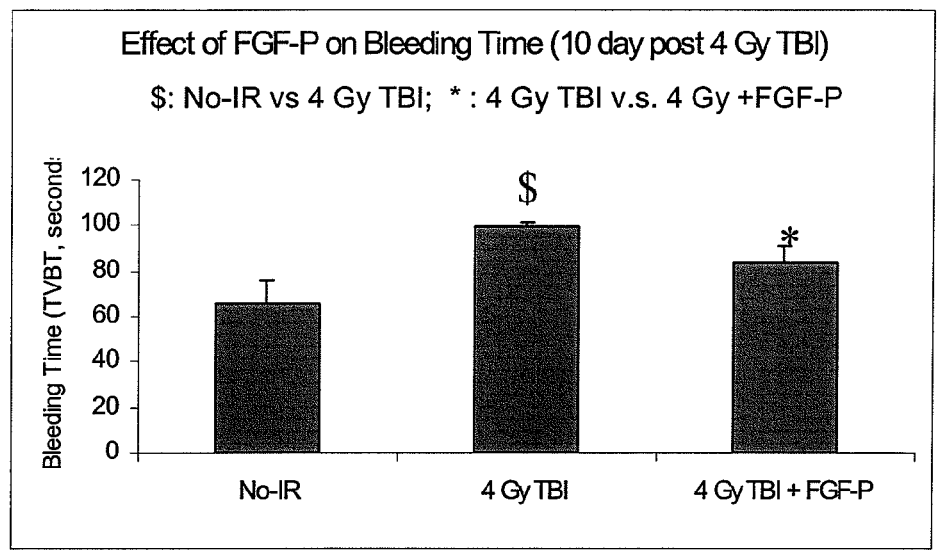
FIG. 19 shows that FGF-P shortens the bleeding time.

3. FGF-P Shortens the IR Prolonged Bleeding Time:

The bleeding is stopped by coagulant cascade, mainly the platelet aggregation, the vessel contraction and thrombosis which are trigged by the released platelet granules (*Francis* 2007, Khorana 2005). IR blocks the megakaryocytopoiesis and reduces the thrombocytopoiesis (an imbalance between the synthesis and consuming of coagulant proteins), which leads to a prolonged bleeding time. To determine if FGF-P has any effect on the bleeding time, the a single tail vein at the same anatomy position was cut in same depth and merged into 37° C. warm water, the time between bleeding and stopping was recorded. The test was performed on 10 days after 4 Gy TBI. As shown in FIG. 19, mice treated with FGF-P (15 mg/kg) right after IR daily for 3 days and then every other day for 3 times had a shorter bleeding time compared to the vehicle control, indicating that FGF-P improves both megakaryocytopoiesis and thrombocytopoiesis.

B8. FGF-P Reverse IR-Altered Gene Expression Pattern.

Figure 20:
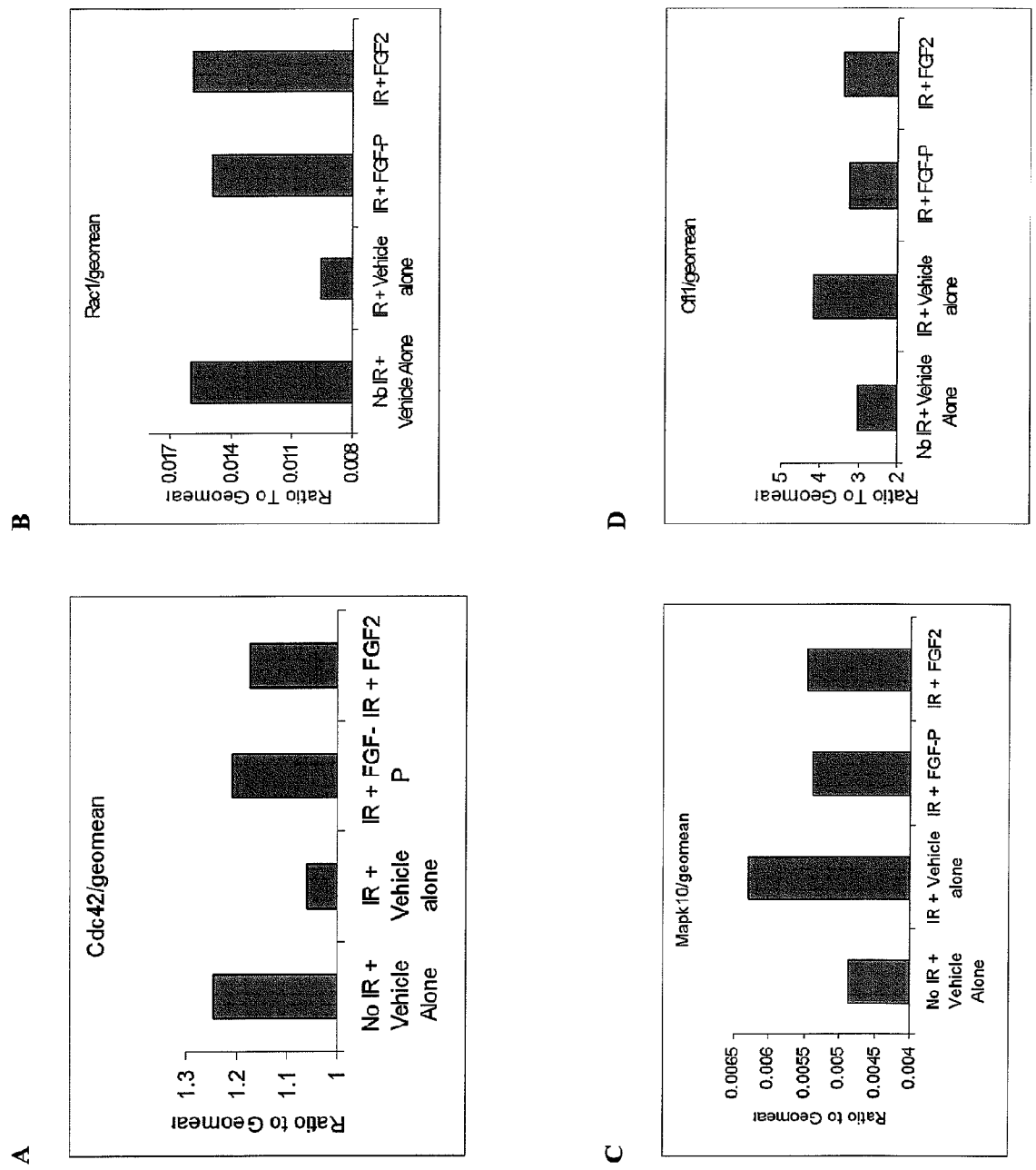
FIG. 20 shows (A) FGF-P increases Cdc42. (B) FGF-P increases Rac 1. (C) FGF-P decreases Mapk10. (D) FGF-P decreases Cfl.

One effect of IR on the BM is to alter gene expression. An effective IR mitigation agent is likely to reduce these changes and revert the pattern toward normal. The Luminex bead array for multiplex gene expression (Panomics Inc, Fremont, Calif.) was used to examine these changes in mouse BM after IR. This array measures 24 genes (Hprt1, Gapd, Actb, Ppib, Ssh1, Pak4, Diap2, Rhoa, Iqgap1, Pfn1, Limk2, Limk1, Gna13, Cdc42, Calm1, Tiam1, Mapk10, Rock1, Rac1, Pip4k2a, Pik3r2, Pak3, Cfl1, Arhgdib) with the results normalized with 4 house-keeping genes (Hprt1, Gapd, Actb, Ppib, collectively named Geomean). Fresh mouse BM cells in serum-free UltraDoma-PF media were divided into 4 groups: 1) normal; 2) IR+ vehicle alone; 3) IR+FGF-P; and 4) IR+ native FGF2 as positive control. The treatments were started 20 min after 5 Gy IR, and the cells were then cultured for 6 more hours before harvesting with Homogenizing Solution® (Panomics). The Geomean normalized results were compared among four groups. As shown in FIG. 20, FGF-P or native FGF2 had similar effects on IR-induced alteration of gene expression. Among them, four were statistically significant ($P<0.05$). For example, treatment with FGF-P or FGF2 reversed the IR-suppressed expression of Cdc42 (cell division cycle 42 homolog) and Rac1 (RAS-related C3 botulinum substrate, FIGS. 20A and B). The signaling of both Cdc42 and Rac1 accelerates p38-related progression of cell cycle, which is needed for cell survival. Similarly, IR increased expression of Mapk10 (mitogen activated protein kinase 10) and Cfl (cofilin 1), and this was suppressed towards normal by treatment with FGF-P or FGF2 (FIGS. 20C and D). The biological meaning of these changes requires further study. This study of gene expression shows that changes induced by IR can be identified and that FGF-P reduces IR-induced changes.

FGF-P Reverses the IR-Altered Cytokine Pattern.

Figure 21:
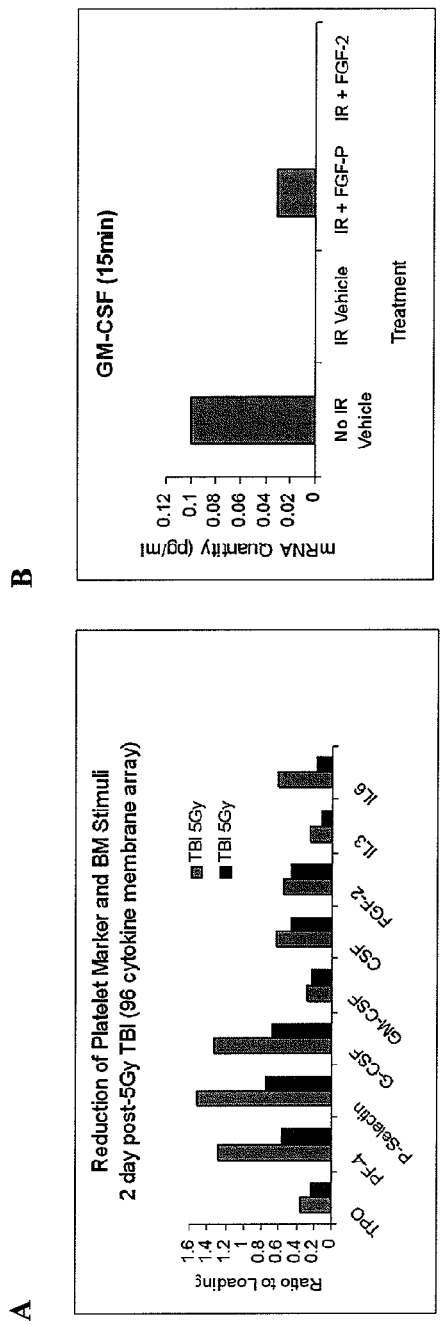
FIG. 21 shows (A) Reduction of platelet marker and BM stimuli. (B) FGF-P increases the IR-reduced GM-CSF. (C) FGF-P increases.

A 96 cytokine membrane array (RayBioTech, Norcross, Ga.) and a Luminex Multiple cytokine beads array (Panomics, Fremont, Calif.) were used to determine the alteration of a panel of plasma cytokines after IR and the effect of FGF-P on reversing the altered pattern. FIG. 21A indicated that the platelet-related molecules (P-selectin and PF4) and BM stimuli (TPO, IL3, IL6, FGF-2, G-CSF and GM-CSF) were reduced on day 2 post-IR, signifying that an exogenous supplement is needed. The addition of FGF-P indeed increased the IR-reduced GM-CSF (FIG. 21B). XXXFGF-P also exerts homeostatic effect to keep cytokine level towards normal balance.

FGF-P Reduces the IR Induced Infection.

Figure 22:
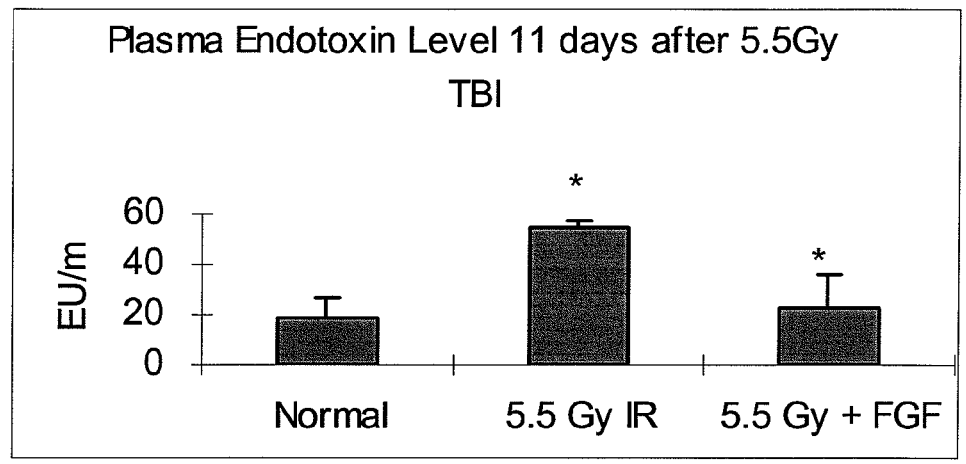
FIG. 22 shows that FGF-P reduces the plasma endotoxin.

The IR-induced decline of WBC and immunity results in the infection as evidenced by the increased plasma level of endotoxin, while treatment of IR mice with FGF-P reduced the LPS level (FIG. 22). This relates with the FGF-P promotion of WBC regeneration. The low endotoxin indicates a low probability of endothelium damage and less consumption of platelet, which promotes the recovery of homeostasis of TBI mice.

Taken together, the results of these studies demonstrate that FGF-P is a promising agent to effectively improve platelet recovery and survival of mice when given 8 hour after IR. Part of the benefit can derive from concurrent improvement in leucopenia that reduces infection and its associated platelet consumption. To maximize the mitigation effect of FGF-P in regeneration of platelet and WBC and to understand the mechanism of action, more detailed studies were performed as described below.

Example 3

To Determine the Optimal Dose and Schedule of FGF-P for Platelet Regeneration During ARS (Month 1-4)

FGF-P can possess several critical properties: 1) it has a mitigation effect, given 8 hr post-lethal TBI; 2) it is a stable peptide that can be synthesized and stored in large quantities ready to be delivered at any time; 3) it can be self-administrated, providing ease of use following a mass casualty; and 4) it is a peptide of human origin without toxic effects or immunogenicity; therefore, it can be used in normal, healthy populations.

Although FGF-P has beneficial effects on WBC regeneration, platelet regeneration is used as an endpoint to determine the optimal FGF-P dose, timing and schedule because: 1) thrombocytopenia is one of major causes of death with ARS, and recovery from thrombocytopenia can be one of the main contributors to ability of FGF-P to improve survival; and 2) an experimental approach to monitor platelet counts and function after IR has been established showing a large effect.

Throughout this set of experiments, Balb/c mice are be given 5 Gy TBI. This IR dose is selected because: 1) It is <LD50/30 dose (about 5.6-5.8 Gy); therefore, it allows all IR mice to survive during the 30 day experimental period which is the time required to examine the hematological alterations caused by IR; 2) Following 5 Gy IR, about 0.6 ml of blood required for platelet aggregation testing is obtained, whereas mice receiving higher doses are ill and blood drawing is technically difficult; and 3) it has been found that IR doses that are too high or too low result in a loss of ability to sensitively identify the best conditions for administration of the agent.

The following endpoints are used to reflect reconstitution of platelets: 1) measurement of platelet count at different time points following IR; 2) platelet function as reflected by aggregation assays at selected times; and 3) the level of platelet associated markers in blood, including P-selectin, PF4, c-Mpl and TPO; and 4) bleeding time. Since FGF-P is a small peptide with 17 amino acids, it has a significant renal clearance. It is critical to identify the optimal dose that gives a maximal anti-ARS effect and also to maintain the plasma level required at other critical sites, such as liver and kidney, which produce other growth stimulators (such as TPO, EPO and G-CSF, GM-CSF) for hematopoietic progenitors. Current studies focused on mitigation of gastrointestinal IR symptoms are investigating the Pharmacokinetics (PK) of FGF-P under no-IR and the results are being used to guide dose selection in the studies proposed herein. However, the PK is likely to vary with time after TBI due to the many physiological changes that occur. The best way to determine the optimal use of FGF-P is to test a series of doses in TBI mouse model and examine PK.

Methods:

1) Preparation of FGF-P: Up to 10 grams of FGF-P (HPLC>95% pure) are contracted to ensure consistency for the course of the experiments 2) Preparation of animals: Balb/c mice from NCI are be used for defining the optimal conditions (dosing, timing and schedule). The mice (6-8 weeks old, male) receive 5 Gy TBI and then are randomly divided into groups (8 mice/group) for different tests.

3) Parameters for determination of platelet regeneration:

A) Platelet number: The number of platelets reflects the extent of megakaryocytopoiesis. A method by which 80 ul of unclotted blood can be obtained from the tail vein for enumeration of platelets using a hematocounter designed specifically for mouse blood cell differential counts (Hemavet 950FS, Drew Scientific) has been worked out. This device has several advantages: a) it yields precise and consistent results; b) it avoids human manual counting error; and c) it fulfills the needs for platelet counts in a large number of samples generated from this proposed study. Observations are be carried out on days 5, 10, 15 20 after-IR to characterize the time dependence of regeneration.

B) Platelet aggregation assay: Hemostasis depends on both and adequate number and also adequate function of platelets. It is, thus, critical that the regenerated platelets following FGF-P treatment function well. This is characterized by testing platelet aggregation. Platelet aggregation is preformed by whole blood electrical impedance method utilizing instrumentation, software and reagents from Chronolog Corporation (Havertown, Pa. USA). Whole blood anticoagulated 1:9 with freshly prepared 100 Unit sodium heparin is collected from subject mice by atraumatic IVC stick using a 27 ga. needle and assayed with minimal delay. Chronolog model 560VS and AGRO/LINK(7) software is used to measure whole blood platelet aggregation using 10 uM ADP as the agonist.

C) Megakaryocyte colony formation: Mice are sacrificed at different times, and BM cells are flushed and seeded in Mega-Cult-C Collagen and modified media purchased from Stem-Cell Technologies Inc. (Vancouver, Canada). Two sets of experiments are performed: 1) examine the effect of FGF-P in vivo, in which Megakaryocyte colonies are compared between the BM from vehicle treated and FGF-P treated mice; and 2) the BM is treated with vehicle or FGF-P in vitro. These experiments characterize the responsiveness of megakaryocytes to FGF-P both in vivo and in vitro.

D) Plasma level of P-selectin, PF4, c-Mpl and TPO: c-Mpl, P-selectin and PF4 present on/in megakaryocytes can be released into the blood, and represent be markers for regenerating platelets, especially after IR depletion. TPO, which is mainly produced by the liver and kidney, is sensitively regulated by the level of platelets. FGF-P stimulates the production of TPO and indirectly enhances the proliferation of megakaryocyte (Bartley 1994, de Sauvage 1994, Kaushansky 1994, Kaushansky 1995, Kato 1995, Nichol 1995, Debilit 1995, Zeigler 194, Berthier 1997). These proteins in plasma or BM cell lysate or culture media collected from different time points after IR are measured with ELISA or Luminex bead array using commercially available reagents.

E) Bleeding time: The bleeding time is an overall measure of the integrity of the homeostatic system and is sensitive to platelet abnormalities. Bleeding times are performed as an assessment of homeostatic following FGF-P treatment. One tail vein in the same anatomic position is cut with a blade, the whole tail is submerged in 37° C. water, and the bleeding time is determined.

4) Determination of optimal FGF-P dosing: Different doses of FGF-P (0, 1, 5, 10, 15, 20, 25, 30, 35 40, 50 or 60 mg/kg in 0.2 ml saline) are given IM to BALB/c mice 8 hours after irradiated with 7 Gy TBI daily for 5 days and then every other day up to 14 days, which covers the course of regeneration. The every other day schedule provides the best interval for cell stimulation.

5) Optimal starting time: Identifying the best starting time is critical for successful treatment because of the complicated pathological process triggered by TBI, and this must be determined experimentally. Because of the focus on mitigation (rather than prevention), treatment starts after IR. To find the best point, a series of starting times (0, 1, 4, 8, 12, 24 and 48 hr post-IR) is tested with an optimal dose defined above, and the treatment is given daily for 5 days and then every other day up to 14 days. Mice that received 7 Gy TBI do not die within 8-14 days, they survive for a long term.

6) Optimal schedule for administration of FGF-P post-IR: The number of does and the intervals of FGF-P treatment needed to achieve the most effective mitigation effect are determined. The optimal dose of FGF-P is given in different courses, such as daily IM for 1, 2, 3, 4, 5, 6, 7 up to 14 days or twice a day for 14 days or in an every other day schedule for 14 days. Although the PK data (obtained from the other study) can guide the administration schedule, these experiments are critical because IR damaged BM cells respond differently to normal cells.

7) Data analysis: The mean and standard deviation of each test (8 samples/group) is calculated and analyzed for statistical significance using student t test or ANOVA as appropriate. The difference of platelet number, platelet aggregation, bleeding time and level of P-selectin, PF4, c-Mpl, TPO is compared among the groups with different doses, timings and schedules.

Interpretation, potential problem and alternatives: The effect of FGF-P on regeneration of platelets with different dosing conditions has been shown herein. These parameters are used to find the best dose, timing and schedule for stimulating platelet regeneration. The focus is on platelets, but data regarding leucocytes and also evidence of infection is collected, since they affect the platelet results via increased consumption that occurs with neutropenic infection.

Example 4

To Determine the Effect of the Combination of FGF-P with TPO on Platelet Regeneration During ARS (Month 4-8)

TPO, the main stimulator for the c-Mpl receptor on megakaryocyte, is critical for megakaryocytopoiesis and thrombocytopoiesis. However, TPO does not work alone but needs other growth factors (Waselenko 2004, Dorsch 1995, Chen 1995, Bacon 1995, Ezumi 1995, Ballmaier 1998, Luoh 2000, Tonelli 2000, Bartley 1994, de Sauvage 1994, Kaushansky 1994, Kaushansky 1995, Kato 1995, Nichol 1995, Debilit 1995, Zeigler 1994). To determine if the combination of FGF-P and TPO can synergistically enhance thrombocytopoiesis during ARS, TPO (native protein or peptide form) and FGF-P are tested together in 2 ways: 1) use at the same time; 2) use in sequence with the TPO first for 1-3 days and then together with FGF-P for a few more days or the other way around, in order to determine if FGF-P increases the level of TPO and the cells' response to TPO.

Figure 23:
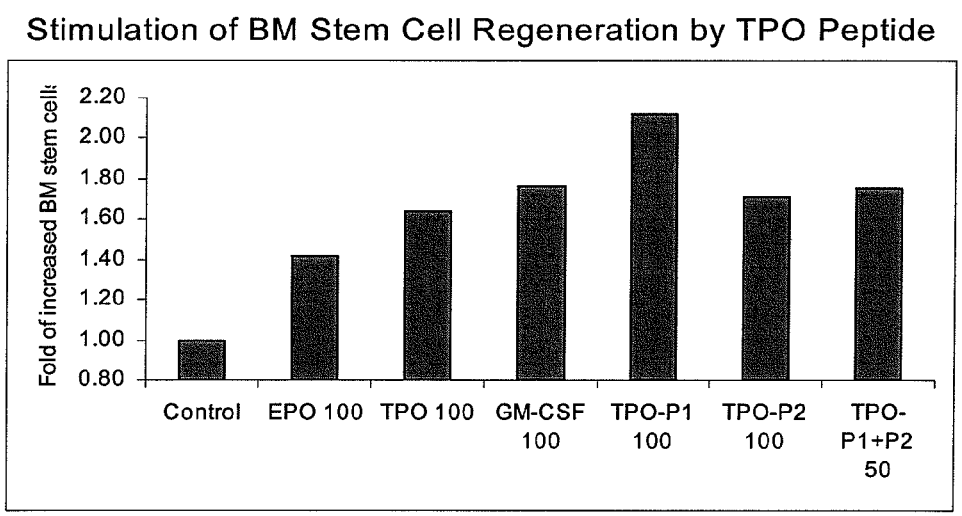
FIG. 23 shows the effect of TPO peptide on regeneration of BM cells.
Figure 24:
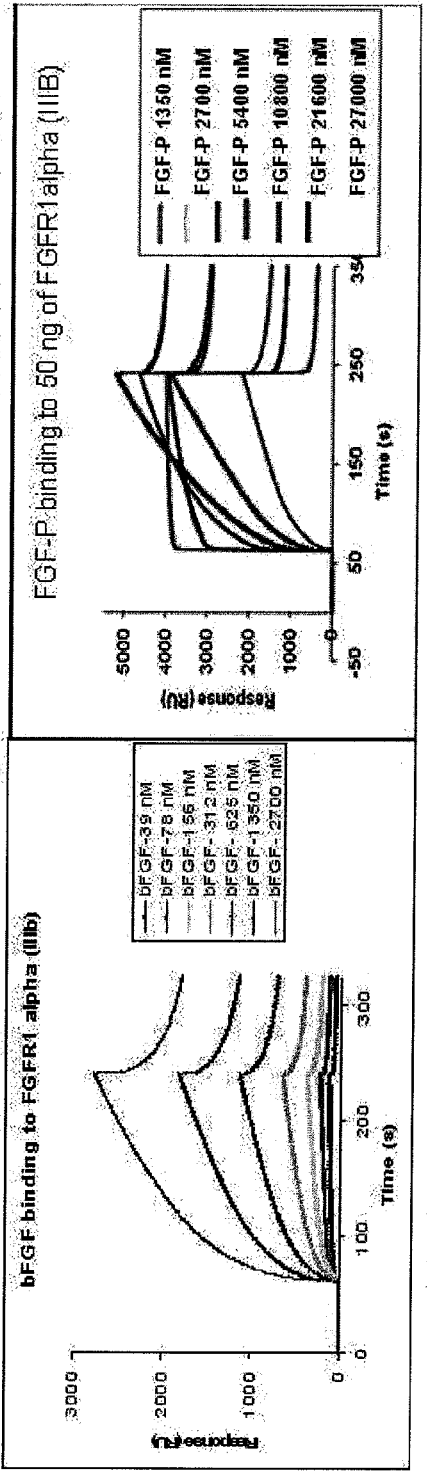
FIG. 24 shows the binding of FGF-P to human FGFR1 (Biacore assay).
Figure 25:
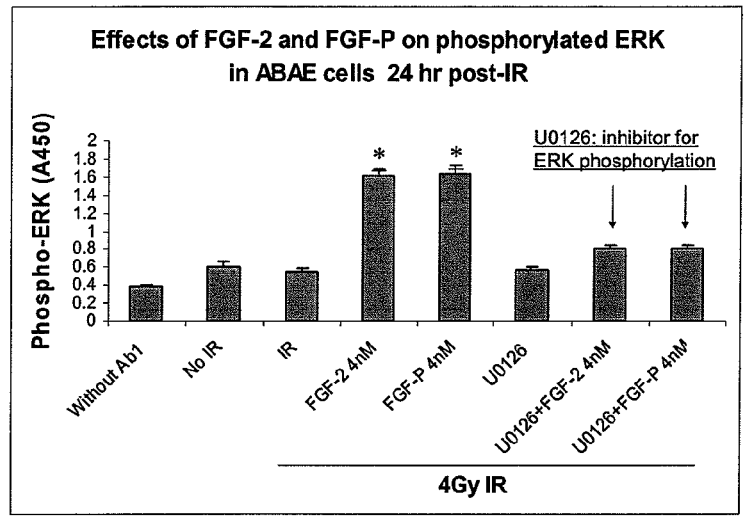
FIG. 25 shows that FGF-P triggers phosphorylation of ERK Pathway.
Figure 25:
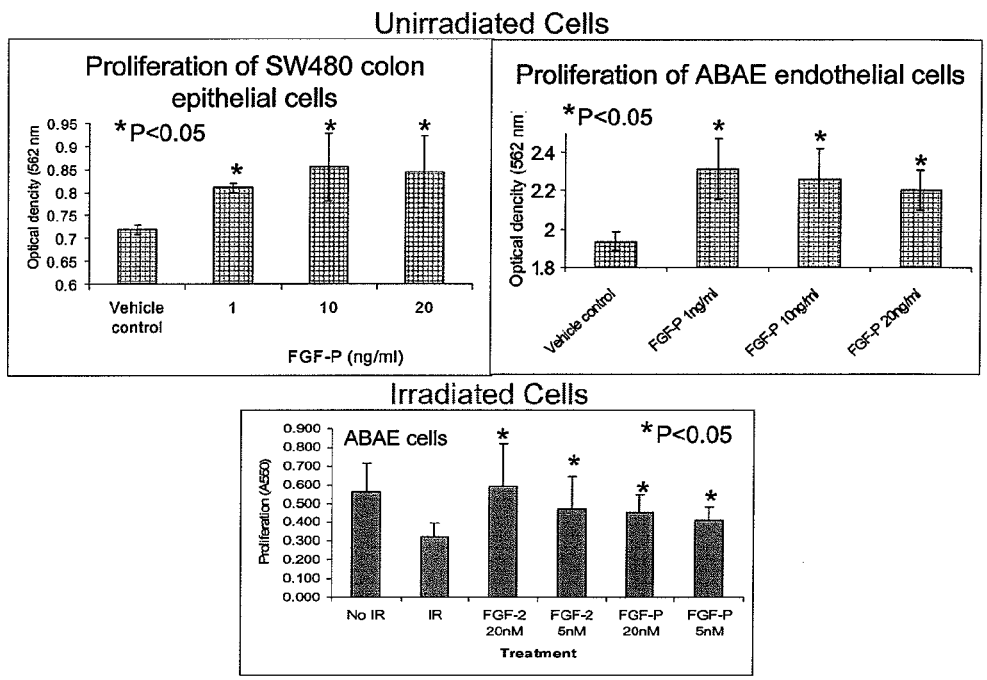
Figure 26:
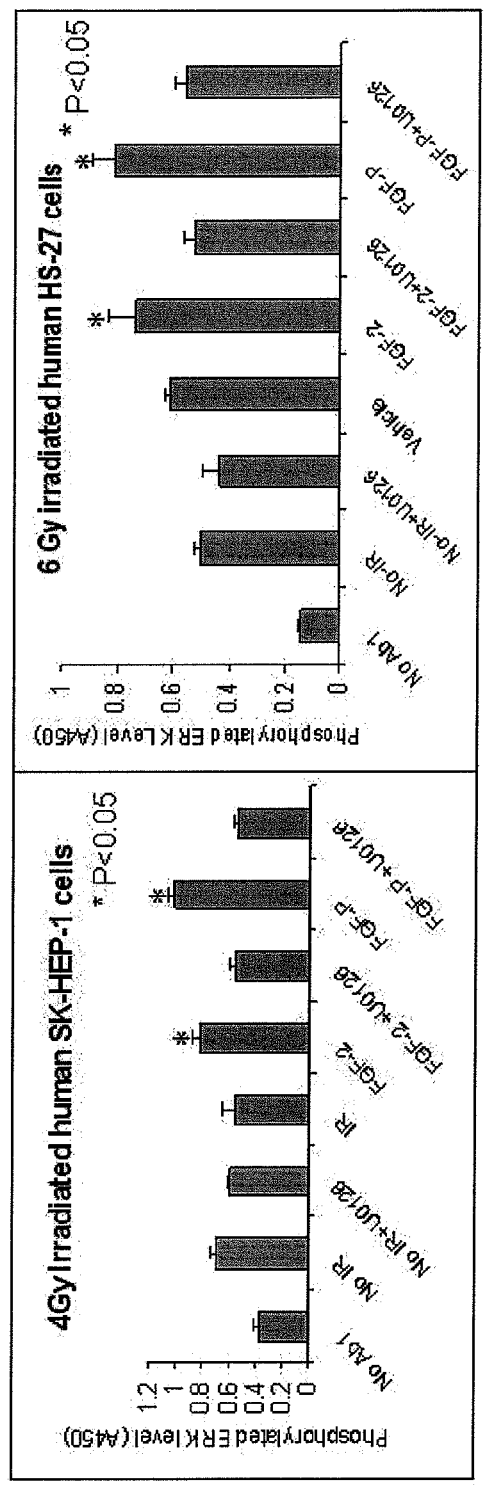
FIG. 26 shows that irradiated human cells maintain their responsiveness to FGF-P.
Figure 27:
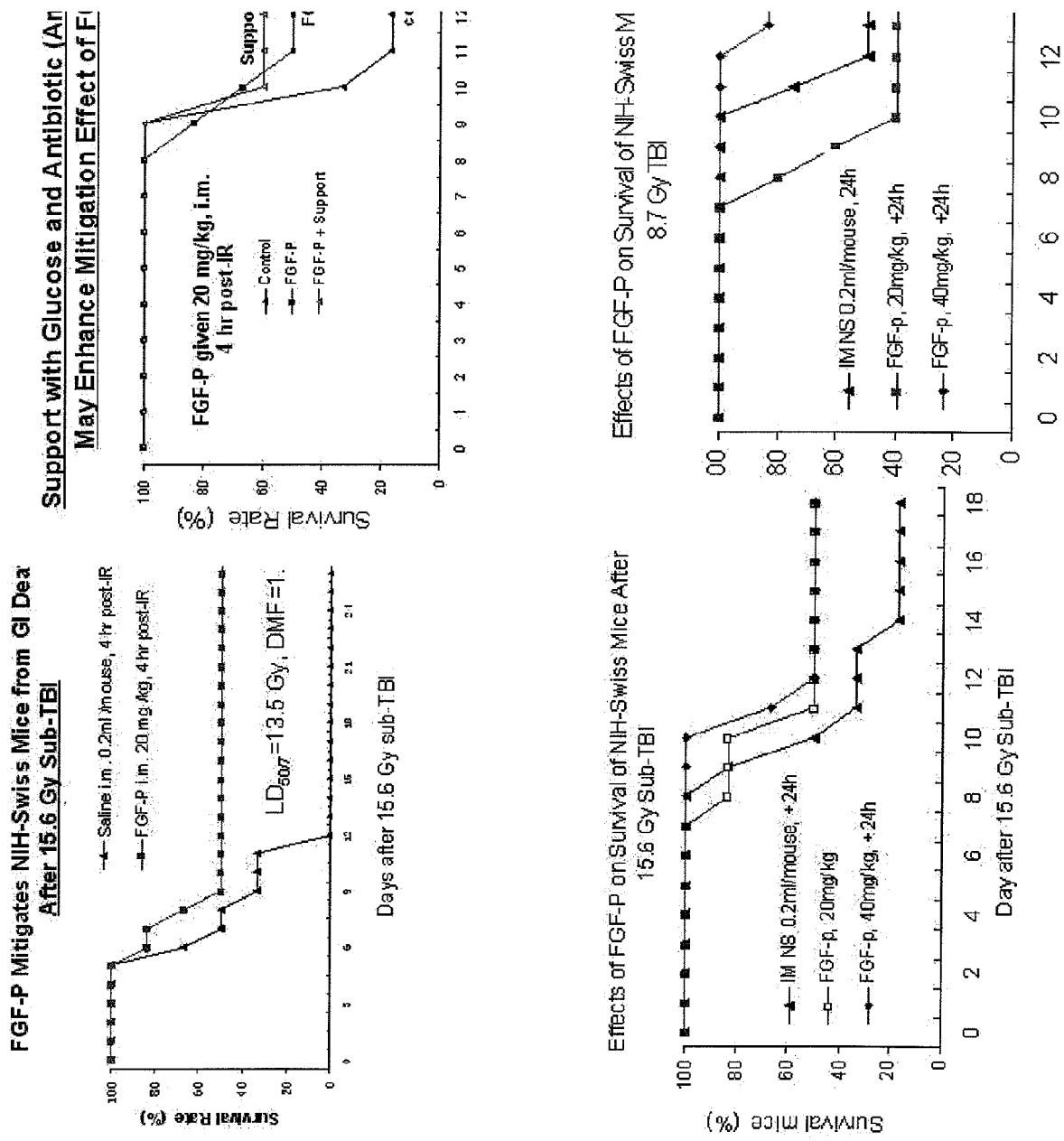
FIG. 27 shows the mitigation Effect of FGF-P on Acute Radiation Syndrome (FGF-P is administrated 4 or 24 hours after radiation). FGF-P improves GI function: The absorption of Na coupling with nutrition and blocking of pathogen invasion are the basic function of GI. Rescued mice have been observed to have a fast recovery of body weight and reduced level of plasma endotoxin. To pin down the mechanism in cell/tissue level, the electrolyte transport assay with $^{22}$Na flux was carried with Ussing chamber. The result showed that the IR reduced Na transport from mucosa to serosa was reversed by FGF-P, indicating that FGF-P increases the GI absorptive function. Similarly, a "Dilution Potential" experiment was carried out and Goldman-Hodgkin-Katz (GHK) Voltage Equation used to determine relative paracellular permeability. Normally, the GI permeability is selectively for 1 Cl:2 Na as PCl/PNa=0.5, which was lost to about 1 after 7 Gy IR, however, FGF-P was capable to reverse back to about 0.5, indicating that the FGF-P restores paracellular selectivity of irradiated GI.
Figure 28:
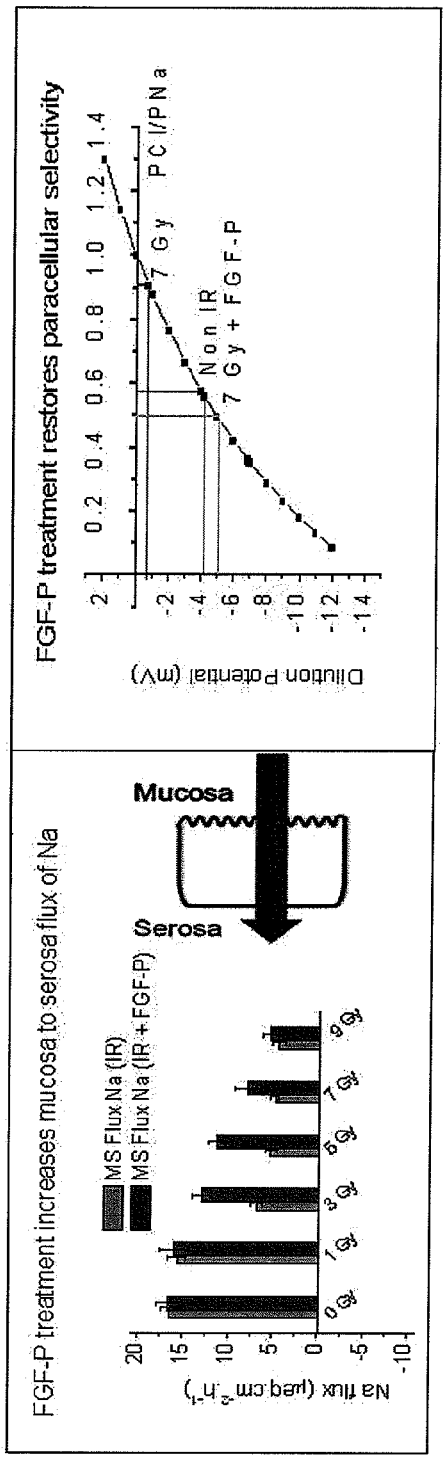
FIG. 28 shows that FGF-P treatment increases mucosa to serosa flux of Na. FGF-P treatment restores paracellular selectivity.

Peptides have important practical advantages including stability and ease of use. Therefore, some proprietary TPO peptides (TPO-P1 and TPO-P2 for two different binding sites) have been designed and synthesized based on the structure of the receptor-binding domain of human native TPO (Feese 2004). These proprietary peptides (100 ng/ml) were added to cultured BM stem cells, and the CyQUANT® assay was used to measure the number of regenerated cells 7 days later. The pilot data was very promising and indicated that TPO-P1 had a strong stimulatory effect (FIG. 23). The binding affinity (Kd) and specificity is currently being characterized using a Biacore two molecule interaction assay (Lin 2006, Lin and Pena 2006). FGF-P used in optimal conditions (dose, starting time and schedule) can be combined with TPO (both protein and TPO-P1 peptide).

Methods:
1) Preparation of TPO or TPO-P1: Native mouse full length TPO was purchased from PeproTech, Inc. (Rocky Hill, N.J.). TPO-P1 was synthesized by GeneMed Inc.

2) Use of animals: Similar to Aim 1, 5 Gy irradiated TBI BALB/c mice are randomly divided into groups (8/group) and used for determination of the optimal dose, starting time and schedule of different combinations of FGF-P and TPO/TPO-P1.

3) Platelet parameters for evaluating the combination effect: As described above, the whole panel of platelet parameters (serial platelet numbers, aggregation, megakaryocyte colony formation, platelet markers and bleeding time) is used for the following combination tests:

4) Combination of FGF-P with TPO/TPO-P1 at different doses: The optimal dose of FGF-P defined in Aim 1 is combined with different doses of native TPO (0, 0.5, 2.5, 10 and 50 ug/kg) or TPO-P1 peptide (0, 5, 10, 15, 20, 30 and 40 mg/kg). The dose for peptide is higher due to its rapid renal clearance. The effective dose range has been shown to be about 15-40 mg/kg in vivo. Doses are given for 14 days as the first test and readjusted according to the result of platelet indices. The most effective dose is used for PK of TPO study to provide information for schedule design.

5) Sequential combination: Three types of combinations are compared: a) optimal dose of FGF-P and TPO given at the same time daily for 12 days; b) optimal dose of FGF-P given for first 3 days followed by the optimal dose of TPO for up to 14 days; and c) TPO first followed by FGF-P.

6) Optimal schedule for combination: The optimal treatment duration is also. For this, the optimal dose and sequential combination (defined from above experiments) are used for different duration of treatment (daily for 1, 2, 3, 4, 5, 6, 7 up to 14 days) and then select the one with best reconstitution of platelets.

7) Statistical analysis: Since the panel of platelet parameters used is the same as above, the data is analyzed as described above using student t test or ANOVA as appropriate. The comparison is made among the different combination groups (different doses, timings and schedules).

Interpretation, potential problem and alternatives: The combination of FGF-P (broad effect) and TPO (specific effect) at optimal conditions can result in synergistic enhancement of megakaryocytopoiesis/thrombocytopoiesis. If TPO-P1 exerts an effect similar to native TPO, then it can also provides the advantages of a peptide (as FGF-P) and allows for the use of this critical factor for megakaryocytopoiesis in a convenient way. The results are useful in further understanding the basic mechanisms of megakaryocytopoiesis in addition to providing a practical drug.

Example 5

To Determine the Effect of FGF-P Alone or in Combination with TPO on Survival During ARS (Month 8-18)

The goal of the above optimization of FGF-P alone and in combination with TPO is to maximize the mitigation effect to reach DMF (dose modification factor)>1.2 or prolong the survival time>50%. So far, few agents can exert a mitigation effect when given after high-dose IR, therefore, this study promotes the development of FGF-P/TPO and provides the basis for the translation of pre-clinical anti-ARS studies into practical countermeasures to ameliorate ARS.

The optimal dose/time/schedule discussed above is applied to Balb/c mice given 7 Gy ($LD_{100/15}=1.2 \times LD_{50/30}$) TBI. The survival rate, the most critical criteria to evaluate the effect of anti-IR agent, is used as the major endpoint.

Methods:
1) Preparation of animals: BALB/c mice (6-8 weeks old) are randomly divided into groups (20 mice/group) to determine if the optimized conditions exert an improved mitigation effect. The focus is first on males (since the majority of warfighter and first-line responders are young men). Younger animals and females are to be evaluated at a later time. The mice are housed for 1 week to acclimate before each experiment.

2) TBI and treatments: The mice are given 7 Gy TBI and treated with: a) vehicle alone as control; b) optimal condition of FGF-P alone; c) optimal condition of FGF-P plus TPO; d)

TPO alone. The dose, timing and schedule are selected in Aim 1 and Aim 2 that use platelet-related parameters to determine the best treatment conditions.

3) Observation of mitigation effect: The effect of optimal conditions of administration (dosing, timing and schedule) is determined by the survival rate. The mice are closely observed for sickness including signs such as brain bleeding as shown in paralysis, DIC as shown in blue nose and swollen head. The number of mice with symptoms is recorded, but the survival rate and time are the principal endpoints.

4) Confirming the mitigation effect in other strains of mice: To determine if the mitigation effect achieved with BALB/c mice can be generalized, C57BL/6 and C3H/HeN mice are tested under the same conditions. Some pilot studies have been conducted with these two strains and their $LD_{50/30}$ are known under these study conditions. To test if FGF-P alone or with TPO has a mitigation effect on C57BL/6 and C3H/HeN mice exposed to lethal IR dose, a $LD_{100/30}$ ($=1.2\times LD_{50/30}$) dose are used, i.e. 10.8 Gy TBI for C57BL/6 and 9 Gy TBI for C3H/HeN. The IR mice are divided into 4 groups (20/group), treated and observed as above. Since the optimal conditions of using each agent differ, re-adjustment is needed.

5) Statistical analysis: Based on the previously measured coefficients of variance between control and IR animals, and assuming a 50% improvement using FGF-P, the group sizes of 20 animals are sufficient to detect those differences for most assays. This provides us a power of near 80% of detecting a difference even for the most challenging assays. The unpaired Student's t-test and Kaplan-Meier and Log-rank test for survival rate are used for statistical significance among the testing groups.

Interpretation, potential problem and alternatives: The optimal conditions determined by platelet related indices are expected to translate into an improved survival. This survival mouse model has been used in testing mitigation agents for years. It has been observed that ⅓ of mice die of obvious brain bleeding as shown in paralysis. Almost all of them have DIC ("blue" nose) and infection (swollen face, eye secretion, etc). If FGF-P alone or with TPO can rescue mice or prolong their survival, then it is likely that the agents directly or indirectly enhance the regeneration of platelet and WBC. Other mechanisms can relate to FGF-P protecting hematopoietic progenitors from IR-induced apoptosis.

Example 6

To Determine the Mechanism of Action by which FGF-P Exerts a Mitigation Effect on Megakaryocytopoiesis (Month 8-18)

FGF2 is a potent multi-functional factor. FGF2 and FGF receptors are expressed by almost all types of cells, including several hematopoietic cell lineages (Hartmann 1997, Kashiwakura 2005, Allouche 1995). The interaction of FGF2 with its receptors stimulates cell proliferation, differentiation, survival and motility, including those with different stem cells (Kardami 2007, Jiang 2002, Kashiwakura 2005, Allouche 1995). FGF2 has a demonstrated beneficial effect in several situations, including onset of ischemia due to acute and chronic cardiac dysfunction (Jiang 2002). Previous studies have demonstrated the prevention or mitigation effect of FGF2 on ARS (Ding 1997, Peña 2000, FIG. 10, 4, 11, 12). FGF-P utilizes the functional domain of FGF2 with its advantages of stability and cost effectiveness. Treatment FGF-P post-IR enhances the regeneration of platelets (FIG. 17) and recovery of platelet aggregation (FIG. 18) and reduces the bleeding time (FIG. 19). It also enhances the reconstitution of WBC (FIG. 17C) and reduces the plasma endotoxin (FIG. 22). The rescuing effect can be seen even 8 hours after a lethal TBI dose (FIG. 12). At the cellular level, these effects seem to relate to FGF-P reconstitution of BM after IR as evidenced by increased proliferation and number of BM cells (FIG. 13-15) and their cell surface markers of CD24 and CD34 (FIG. 16). At the molecular level, the effect relates to effects on gene expression and cytokine levels (FIG. 20, 21).

Methods:

1) Preparation of in vivo and in vitro samples: Samples are collected from: a) in vivo: Balb/c mice (5-8/group) receive 5 Gy TBI and then treatment at 8-24 hr after IR with vehicle (as control) or optimal dose of FGF-P±TPO-P1 or FGF2 10 ug/mice or TPO 50 ug/mice (as positive control, dose selected based on previous experience) for an optimal course (defined above). The timing of mouse sacrifice depends on the assay requirements. The night before sacrifice, BrdU (120 mg/kg) is i.p. injected for the BM cell proliferation assay. Blood is collected from the IVC, and BM cells are flushed out and directly used in various assays. The results reflect an overall effect after IR and treatment; and b) in vitro: BM cells from mice 8-24 hour after 5 Gy TBI are cultured in round-bottom 96-well plates with serum-free ultraDoma-PF media and then treated with different doses (0, 10, 100, 250 and 500 ng/ml) of FGF-P and/or TPO or FGF2 or TPO 10-30 ng/ml (as positive control) for different lengths of time (depending on assays: for phosphorylation 15 min; for gene expression 6 hr; for protein alteration 24-48 hr). These data reflect the responsiveness of BM cells to treatment at different levels in a dose-dependent manner.

2) Treatment effect on CD24, CD34, SCF, c-kit and Sca-1 on BM cells or in plasma and media: All of these markers are for BM cells and can be used as surrogates to determine the extent of regeneration. Freshly harvested or cultured BM cells are stained with FITC or PE conjugated antibodies against these markers, and analysis for the % of positive cells and the intensity of these markers are performed using flow cytometery (FCM). Another quantitative method is ELISA with the cell lysate or plasmas or culture media. The BM samples are collected at different time points to study the dynamic alteration of these markers during the course of FGF-P/TPO-P1 treatment.

3) Treatment effect on BM cell proliferation and apoptosis: FGF2 is a pleiotropic growth factor that promotes cell proliferation, migration and differentiation (Boilly 2000, Kinkl 2002, Curto 1998, Cailliau 2003, Xie 1999, Koga 1999, McKeehan 1998, Klint 1999, Lewis 1998). On other hand, FGF2 also protects BM cells from IR-induced apoptosis. Therefore, the extent of both proliferation and apoptosis are measured. For proliferation, the in vivo incorporated BrdU in BM cells are measured with FCM or ELISA. The in vitro incorporated $^3$H-TdR is harvested with automatic 96 well harvester and counted with a counter. For apoptosis, the freshly harvested or cultured BM cells are stained with Annexin V-FITC and analyzed by FCM. Caspase 3, 8, 9 and PARP are assessed with their activity assay kit (Mol Probe, Inc) or Western blot.

4) Treatment effect on gene expression, phosphorylation of Ras, ERK, MAPK, Stat 3, stat5, and Akt and TFs related to FGF2, radiation and stem cells: FGF-P and TPO signal for cell proliferation through different pathways and involve a cascade of protein phosphorylation, including Ras, ERK, MAPK, p38, Akt, Src 2 homology domains, Stat 3, stat5, etc (Feese 2004, Dorsch 1995, Chen 1995, Bacon 1995, Ezumi 1995, Ballmaier 1998, Luoh 2000, Tonelli 2000, Boilly 2000, Kinkl 2002, Curto 1998, Cailliau 2003, Xie 1999, Koga 1999, McKeehan 1998, Klint 1999, Lewis 1998). First, BM samples collected 15 min after treatment and analyzed using phosphorylation multi-analyte kits produced by Panomics using Luminex bead array technology. Second, the BM samples collected 1 hr after treatment are assayed for the active form of TFs (transcription factors), such as NFkb, P53, Myo D, Smad, C-myb, AP1, SP6, PPAR, HIF-1, IRF, STAT1, 3, 5, etc. Thirdly, BM samples collected in special mRNA protective homogenizing buffer (provided by Panomics Inc) 6 hr posttreatment are analyzed for the expression level of genes related to radiation, FGF2 and stem cells, such as cdc family, acute reaction proteins, cytokines, cell circle check point proteins and stem cell markers. The panel is designed by experts in Panomics using b-DNA technology, which can detect mRNA in one cell.

5) Treatment effect on cytokine pattern of plasma or conditioned media: BM samples collected 24-48 hr after treatment are analyzed for the protein level of growth factors, cytokines and chemokines using a Luminex bead array, which allows quantitative measurements of up to 45 analyses.

6) Statistical analysis: The mean and standard deviation from treatments are calculated and analyzed for statistical significance using student t test or ANOVA as appropriate. The differences between the vehicle control, treated and positive control are determined.

Interpretation, potential problem and alternatives: This study reveals the molecule network affected by FGF-P/TPO treatment. Since mouse data indicates that FGF-P has a mitigation effect, the results of the indices examined are different between the control and FGF-P treated groups. Because the data reflect an overall balance between the IR induced cell death and FGF-P/TPO promoted regeneration of BM megakaryocyte, the timing of testing is critical. The level of c-Mpl, TPO, P-selectin, PF4 (representing platelet) and CD24, CD34, CSF, C-kit and Sca-1 (representing BM cells) is higher in FGF-P/TPO treated groups and compared to the vehicle alone in IR mice or cells. Differences are seen in protein phosphorylation, TFs, expression level of genes that are related to radiation and stem cells and cytokine between the vehicle control and FGF-P/TPO treated group. The information obtained aids in better understanding the mechanism of action of FGF-P alone and in combination with TPO.

REFERENCES

2. Jerzy G. Maj, François Paris, Adriana Haimovitz-Friedman, Ennapadam Venkatraman, Richard Kolesnick and Zvi Fuks: Microvascular Function Regulates Intestinal Crypt Response to Radiation. Cancer Research 2003; 63, 4338-4341
6. U.S. Pat. No. 4,845,039
7. Whalen G F, Shing Y, Folkman J. The fate of intravenously administered bFGF and the effect of heparin. Growth Factors. 1989; 1(2):157-64
8. Zhang L; Kharbanda S; Hanfelt J; Kern F G: Both autocrine and paracrine effects of transfected acidic fibroblast growth factor are involved in the estrogen-independent and antiestrogen-resistant growth of MCF-7 breast cancer cells. Cancer Res 1998; 8(2):352-61.
10. Jalkanen S, Nash G S, De los Toyos J, MacDermott R P, Butcher E C. Human lamina propria lymphocytes bear homing receptors and bind selectively to mucosal lymphoid high endothelium. Eur J Immunol. 1989 January; 19(1):63-8.
11. Schmitz M, Nunez D, Butcher E C. Selective recognition of mucosal lymphoid high endothelium by gut intraepithelial leukocytes. Gastroenterology. 1988; 94(3):576-81
12. Whitehead R H, VanEeden P E, Noble M D, Ataliotis P, Jat P S. Establishment of conditionally immortalized epithelial cell lines from both colon and small intestine of adult H-2Kb-tsA58 transgenic mice. Proc Natl Acad Sci USA 1993; 90:587-91
14. Kruidenier L, MacDonald T T, Collins J E, Pender S L, Sanderson I R. Myofibroblast matrix metalloproteinases activate the neutrophil chemoattractant CXCL7 from intestinal epithelial cells. Gastroenterology. 2006; 130(1):127-36
15. Diebel L N, Liberati D M, Taub J S, Diglio C A, Brown W J. Intestinal epithelial cells modulate PMN activation and apoptosis following bacterial and hypoxic challenges. J Trauma. 2005; 58(6):1126-33
17. Lee H T, Kay E P. FGF-2 induced reorganization and disruption of actin cytoskeleton through PI 3-kinase, Rho, and Cdc42 in corneal endothelial cells. Mol Vis. 2003; 9:624-34
18. Gu X, Seong G J, Lee Y G, Kay E P. Fibroblast growth factor 2 uses distinct signaling pathways for cell proliferation and cell shape changes in corneal endothelial cells. Invest Ophthalmol Vis Sci. 1996; 37(11):2326-34
19. Boilly B, Vercoutter-Edouart A S, Hondermarck H, Nurcombe V, Le Bourhis X. FGF signals for cell proliferation and migration through different pathways. Cytokine Growth Factor Rev. 2000; 11 (4):295-302
20. Ibrahimi O A, Zhang F, Hrstka S C, Mohammadi M, Linhardt R J. Kinetic model for FGF, FGFR, and proteoglycan signal transduction complex assembly. Biochemistry. 2004; 43(16):4724-30
21. Friesel R E, Maciag T Molecular mechanisms of angiogenesis: fibroblast growth factor signal transduction. FASEB J. 1995 July; 9(10):919-25
22. Burgess W H, Maciag T. The heparin-binding (fibroblast) growth factor family of proteins. Annu Rev Biochem. 1989; 58:575-606
23. Maciag T, Burgess W H. Endothelial cell growth factor. Prog Clin Biol Res. 1986; 226:361-9.
24. Lin X, Takahashi K, Campion S L, Liu Y, Gustaysen G G, Pena L A, Zamora P O. Synthetic peptide F2A4-K-NS mimics fibroblast growth factor-2 in vitro and is angiogenic in vivo. Int J Mol Med. 2006 May; 17(5):833-9
25. Okunieff P, Wu T, Huang K, Ding I. Differential radioprotection of three mouse strains by basic or acidic fibroblast growth factor. Br J Cancer Suppl. 1996 July; 27:S105-8.
26. Ding I, Huang K, Wang X, Greig J R, Miller R W, Okunieff P. Radioprotection of hematopoietic tissue by fibroblast growth factors in fractionated radiation experiments. Acta Oncol. 1997; 36(3):337-40.
27. Okunieff P, Mester M, Wang J, Maddox T, Gong X, Tang D, Coffee M, Ding I. In vivo radioprotective effects of angiogenic growth factors on the small bowel of C3H mice. Radiat Res. 1998 August; 150(2):204-11.
28. Okunieff P, Li M, Liu W, Sun J, Fenton B, Zhang L, Ding I. Keratinocyte growth factors radioprotect bowel and bone marrow but not KHT sarcoma. Am J Clin Oncol. 2001 October; 24(5):491-5.
29. Maclachlan T, Narayanan B, Gerlach V L, Smithson G, Gerwien R W, Folkerts O, Fey E G, Watkins B, Seed T, Alvarez E. Human fibroblast growth factor 20 (FGF-20; CG53135-05): a novel cytoprotectant with radioprotective potential. Int J Radiat Biol. 2005 August; 81(8):567-79
31. Nordgaard I, Mortensen P B. Digestive processes in the human colon. Nutrition. 1995; 11(1):37-45
32. Drucker D J. The role of gut hormones in glucose homeostasis. J Clin Invest. 2007; 117(1):24-32

| SEQUENCES | |
|---|---|
| CYRSRKYSSWYVALKRC | SEQ ID NO: 1 |
| RFHSWDCIKTWASDTFVLVCYDDGSEA | SEQ ID NO: 2 |
| YRSRKYSSWYVALKR | SEQ ID NO: 3 |
| HSDGTFTSELSRLQDSARLQRLLQGLV | SEQ ID NO: 4 |

What is claimed is:

1. An isolated peptide comprising the amino acid sequence

CYRSRKYSSWYVALKRC        (SEQ ID NO: 1).

2. An isolated nucleic acid encoding the peptide of claim 1.

3. A pharmaceutical composition comprising the peptide of claim 1 or a pharmaceutically acceptable salt thereof.

4. An isolated peptide comprising the amino acid sequence

CYRSRKYSSWYVALKRC,       (SEQ ID NO: 1)

wherein one or more sites of proteolysis have been deleted or substituted, and wherein the one or more sites of proteolysis are arginine residues.

5. A method of preventing or treating a disorder affecting rapidly proliferating tissue wherein the disorder is due to radiation exposure comprising administering to a subject an effective amount of a composition comprising the peptide of claim 1, thereby preventing or treating the disorder affecting rapidly proliferating tissue or one or more symptoms thereof.

6. The method of claim 5, wherein the disorder is alimentary mucositis.

7. The method of claim 5, wherein the disorder is oral mucositis.

8. The method of claim 5, wherein the disorder is gastrointestinal mucositis.

9. The method of claim 5, wherein the disorder is a disorder of hematopoiesis.

10. The method of claim 5, wherein the disorder is anemia, leukopenia, thrombocytopenia, pancytopenia, or a clotting disorder.

11. The method of claim 5, wherein the disorder is bone marrow failure, graft-versus-host disease, radiation induced prostatitis, vaginitis, urethritis, or a cardiovascular/central nervous system syndrome.

12. The method of claim 5, wherein the radiation exposure results in diarrhea, skin burn, sores, fatigue, dehydration, inflammation, hair loss, ulceration of alimentary tract mucosa, xerostomia, bleeding, or a combination thereof.

13. The method of claim 5, wherein an effective amount of the composition is administered to a subject who is going to be exposed to radiation, or a subject who has been exposed to radiation but prior to the disorder or a symptom thereof developed in the subject.

14. The method of claim 5, wherein an effective amount of the composition is administered to a subject who has been exposed to radiation and who has developed a disorder or a symptom thereof.

15. The method of claim 5, wherein the effective amount of the composition is administered to the subject in a single dose.

16. The method of claim 15, wherein the single dose of the composition is administered to a subject no more than 24 hours before the subject's exposure to radiation.

17. The method of claim 15, wherein the single dose of the composition is administered to a subject no more than 48 hours before the subject's exposure to radiation.

18. The method of claim 5, wherein the effective amount of the composition is administered to the subject in two or more doses.

19. The method of claim 18, wherein the composition is administered to the subject both before the subject's exposure to radiation and after the subject's exposure to radiation.

20. The method of claim 5, wherein the composition is administered by parenteral route.

21. The method of claim 20, wherein the administration is by intravenous, intramuscular, subcutaneous, intradermal, or intranasal administration.

22. The method of claim 21, wherein the subject is a human.

23. The method of claim 5, wherein the subject is a mammal.

24. A method of promoting angiogenesis in a subject in need thereof, the method comprising administering to the subject an effective amount of a composition comprising the peptide of claim 1, thereby promoting angiogenesis in the subject.

25. The method of claim 24, wherein the angiogenesis takes place at the site of a wound.

26. A method for promoting wound healing in a subject in need of such treatment comprising administering to the subject a wound-healing effective amount of a composition comprising the peptide of claim 1, thereby promoting wound healing in the subject.

27. The method of claim 26, wherein the composition is delivered systemically.

28. The method of claim 26, wherein the composition is delivered topically.

29. The method of claim 26, wherein the composition is administered to tissue.

30. The method of claim 29, wherein the tissue is selected from the group consisting of epidermal, eye, skin, uro-genital, gastro-intestinal, cardiovascular, muscle, connective, and neural.

31. A method of stimulating hematopoietic stem cell proliferation comprising administering to a subject a composition comprising the peptide of claim 1, thereby stimulating hematopoietic stem cell proliferation.

32. A method of optimizing hematopoietic stem cell engraftment comprising administering to a subject a composition comprising the peptide of claim 1, thereby optimizing hematopoietic stem cell engraftment.

33. A method of stimulating gastrointestinal stem cell proliferation comprising administering to a subject a composition comprising the peptide of claim 1, thereby stimulating gastrointestinal stem cell proliferation.

34. A method to stimulate growth and proliferation of cells in a vertebrate animal comprising administering to a vertebrate subject in need of such treatment an effective amount of a composition comprising the peptide of claim 1, thereby stimulating growth and proliferation of cells in a vertebrate animal.

35. The method of claim 34, wherein the cells are crypt cells.

36. The method of claim 35, wherein the cells are in the gastrointestinal tract.

37. An isolated peptide comprising a dimer, wherein the dimer comprises SEQ ID NO: 1.

38. A method for treating an aneurysm in a vertebrate animal comprising introducing an embolus generating vaso-occlusive device into the aneurysm, wherein the vaso-occlusive device comprises an effective amount of a composition comprising the peptide of claim 1, thereby treating an aneurysm in a vertebrate animal.

39. A vaso-occlusive device, comprising an effective amount of a composition that augments fibroblast growth factor activity, which composition comprises the peptide of claim 1.

40. A method to treat ulcerative colitis in a vertebrate animal comprising administering to a vertebrate subject in need of such treatment an effective amount of a composition comprising the peptide of claim 1, thereby treating ulcerative colitis in a vertebrate animal.

41. A defined, isotonic culture medium comprising the peptide of claim 1, sufficient to support growth of substantially undifferentiated mammalian stem cells.

42. A culture medium according to claim 41, wherein the mammalian stem cells are primate stem cells.

43. A culture medium according to claim 42, wherein the primate stem cells are primate primordial stem cells.

44. A culture medium according to claim 43, wherein the primate primordial stem cells are human primordial stem cells.

45. A culture medium according to claim 44, wherein the human primordial stem cells are human embryonic stem cells.

* * * * *